(12) United States Patent
Yair et al.

(10) Patent No.: US 11,202,699 B2
(45) Date of Patent: Dec. 21, 2021

(54) SYSTEMS, METHODS AND DEVICES FOR EMBOLIC PROTECTION

(71) Applicant: Javelin Medical Ltd., Yokneam (IL)

(72) Inventors: Dan Yair, Moshav Kefar Kish (IL); Avi Neta, Gilon (IL); Guy Shinar, Ramat Gan (IL); Ofer Yodfat, Modi'in (IL); Eyal Kaufman, Ein Charod Meuhad (IL); Sagi Shitrit, Adi (IL); Sagit Broder, Gedera (IL)

(73) Assignee: JAVELIN MEDICAL LTD., Yokneam (IL)

( * ) Notice: Subject to any disclaimer, the term of this patent is extended or adjusted under 35 U.S.C. 154(b) by 0 days.

(21) Appl. No.: 16/066,860

(22) PCT Filed: Oct. 20, 2017

(86) PCT No.: PCT/IL2017/051157
§ 371 (c)(1),
(2) Date: Jun. 28, 2018

(87) PCT Pub. No.: WO2018/073830
PCT Pub. Date: Apr. 26, 2018

(65) Prior Publication Data
US 2019/0021836 A1  Jan. 24, 2019

Related U.S. Application Data

(60) Provisional application No. 62/471,676, filed on Mar. 15, 2017, provisional application No. 62/411,353, filed on Oct. 21, 2016.

(51) Int. Cl.
*A61F 2/01* (2006.01)
*A61B 17/00* (2006.01)
*A61B 17/12* (2006.01)

(52) U.S. Cl.
CPC .... *A61F 2/013* (2013.01); *A61B 2017/00017* (2013.01); *A61B 2017/00115* (2013.01);
(Continued)

(58) Field of Classification Search
CPC .......... A61F 2/01–2002/018; A61B 17/12145; A61B 17/1214–12154
See application file for complete search history.

(56) References Cited

U.S. PATENT DOCUMENTS 3,540,431 A   11/1970   Mobin-Uddin
4,425,908 A   1/1984    Simon
(Continued)

FOREIGN PATENT DOCUMENTS

CN   2601642       2/2004
CN   1911188 A     2/2007
(Continued)

OTHER PUBLICATIONS

Cogo et al. "Distribution of Thrombosis in Patients with Symptomatic Deep Vein Thrombosis" Arch Intern Med., 1993, vol. 153, p. 2777-2780.
(Continued)

*Primary Examiner* — Tan-Uyen T Ho
*Assistant Examiner* — Charles M Wei
(74) *Attorney, Agent, or Firm* — Cooley LLP

(57) ABSTRACT

Embodiments of the present disclosure are directed to systems, methods and devices for providing embolic protection in a patient, and implantation of devices (and systems thereof) for enabling such functionality. In some embodiments, a device is configured for implantation in a body vessel including fluid flow. The device may assume, or be constrained to assume, an un-deployed state and a deployed state. In the un-deployed state, the device or a portion thereof is configured to reside in the lumen of a thin needle
(Continued)

or cannula having a diameter of less than about 0.5 mm (for example). The needle may include a curved portion. In the deployed state, the device has an axis which, when implanted, is positioned approximately parallel to the fluid flow of the vessel. In some embodiments, the device comprises a thin filament body whereby in a deployed state, at least a portion of the filament takes on a helical shape. In some embodiments, at least one helix coil has height or pitch greater than the coil diameter. In some embodiments, the device has a monofilament filter portion including at least one coil whose center is off the helix axis. The device may be made of a super-elastic alloy so that the device can transition between the un-deployed and the deployed states without plastic deformation (in at least some embodiments). In some embodiments, the device is configured for trans-catheter delivery.

17 Claims, 63 Drawing Sheets

(52) U.S. Cl.
CPC ............ *A61B 2017/00398* (2013.01); *A61B 2017/00734* (2013.01); *A61B 2017/1205* (2013.01); *A61F 2/011* (2020.05); *A61F 2002/016* (2013.01)

(56) References Cited

U.S. PATENT DOCUMENTS

| | | | |
|---|---|---|---|
| 4,494,531 A | 1/1985 | Gianturco | |
| 4,722,350 A | 2/1988 | Armeniades et al. | |
| 5,059,205 A | 10/1991 | El-Nounou et al. | |
| 5,350,397 A * | 9/1994 | Palermo | A61B 17/12022 128/898 |
| 5,413,586 A * | 5/1995 | Dibie | A61F 2/01 128/899 |
| 5,634,942 A | 6/1997 | Chevillon et al. | |
| 5,649,949 A * | 7/1997 | Wallace | A61B 17/12022 600/200 |
| 5,733,329 A * | 3/1998 | Wallace | A61B 17/12022 606/158 |
| 5,800,454 A * | 9/1998 | Jacobsen | A61B 17/12022 606/191 |
| 5,868,754 A | 2/1999 | Levine et al. | |
| 5,957,940 A | 9/1999 | Tanner et al. | |
| 5,976,172 A | 11/1999 | Homsma et al. | |
| 6,007,558 A | 12/1999 | Ravenscroft et al. | |
| 6,059,825 A * | 5/2000 | Hobbs | A61F 2/01 623/1.18 |
| 6,074,341 A | 6/2000 | Anderson et al. | |
| 6,093,199 A | 7/2000 | Brown et al. | |
| 6,099,549 A | 8/2000 | Bosma et al. | |
| 6,123,715 A * | 9/2000 | Amplatz | A61B 17/0057 606/151 |
| 6,152,144 A | 11/2000 | Lesh et al. | |
| 6,214,025 B1 | 4/2001 | Thistle et al. | |
| 6,238,403 B1 | 5/2001 | Greene, Jr. et al. | |
| 6,344,052 B1 | 2/2002 | Greenan et al. | |
| 6,368,346 B1 | 4/2002 | Jadhav et al. | |
| 6,375,671 B1 | 4/2002 | Kobayashi et al. | |
| 6,395,017 B1 | 5/2002 | Dwyer et al. | |
| 6,652,558 B2 | 11/2003 | Patel et al. | |
| 6,669,707 B1 | 12/2003 | Swanstrom et al. | |
| 6,673,089 B1 | 1/2004 | Yassour et al. | |
| 6,730,108 B2 | 5/2004 | Van Tassel et al. | |
| 7,128,073 B1 | 10/2006 | Van der Burg et al. | |
| 7,144,363 B2 | 12/2006 | Pai et al. | |
| 7,261,731 B2 | 8/2007 | Patel et al. | |
| 7,306,624 B2 | 12/2007 | Yodfat et al. | |
| 7,572,273 B2 | 8/2009 | Mazzocchi et al. | |
| 7,704,267 B2 | 4/2010 | Tessmer | |
| 7,716,801 B2 | 5/2010 | Douk et al. | |
| 7,740,644 B2 | 6/2010 | Beulke et al. | |
| 7,794,494 B2 | 9/2010 | Sahatjian | |
| 8,057,507 B2 | 11/2011 | Horan et al. | |
| 8,118,858 B2 | 2/2012 | Tseng et al. | |
| 8,137,396 B2 | 3/2012 | Busold et al. | |
| 8,206,412 B2 | 6/2012 | Galdonik et al. | |
| 8,221,446 B2 | 7/2012 | Pal et al. | |
| 8,236,009 B2 | 8/2012 | Saadat et al. | |
| 9,220,588 B2 * | 12/2015 | Shinar | A61B 17/0487 |
| 9,592,110 B1 | 3/2017 | Dan et al. | |
| 10,028,819 B2 | 10/2018 | Shinar et al. | |
| 10,226,321 B2 | 3/2019 | Shinar et al. | |
| 10,507,023 B2 | 12/2019 | Poulsen | |
| 10,531,943 B1 | 1/2020 | Dan et al. | |
| 2001/0007946 A1 | 7/2001 | Lenker et al. | |
| 2002/0010481 A1 * | 1/2002 | Jayaraman | A61B 17/0057 606/151 |
| 2002/0188170 A1 | 12/2002 | Santamore et al. | |
| 2003/0100939 A1 | 5/2003 | Yodfat et al. | |
| 2004/0082962 A1 | 4/2004 | Demarais et al. | |
| 2005/0004575 A1 | 1/2005 | Sgro et al. | |
| 2005/0177181 A1 | 8/2005 | Kagan et al. | |
| 2006/0167489 A1 | 7/2006 | Satake et al. | |
| 2006/0212047 A1 | 9/2006 | Abbott et al. | |
| 2007/0010857 A1 | 1/2007 | Sugimoto et al. | |
| 2007/0066863 A1 | 3/2007 | Rafiee et al. | |
| 2007/0156123 A1 | 7/2007 | Moll et al. | |
| 2008/0108933 A1 | 5/2008 | Yu et al. | |
| 2008/0147111 A1 | 6/2008 | Johnson et al. | |
| 2008/0183206 A1 * | 7/2008 | Batiste | A61F 2/01 606/200 |
| 2008/0221600 A1 * | 9/2008 | Dieck | A61B 17/12022 606/157 |
| 2008/0269789 A1 | 10/2008 | Eli | |
| 2009/0054905 A1 | 2/2009 | Levy | |
| 2009/0099591 A1 | 4/2009 | Nardone et al. | |
| 2009/0138066 A1 | 5/2009 | Leopold et al. | |
| 2009/0187211 A1 | 7/2009 | Mackiewicz | |
| 2009/0228020 A1 | 9/2009 | Wallace et al. | |
| 2010/0016881 A1 | 1/2010 | Fleck et al. | |
| 2010/0023024 A1 | 1/2010 | Zeiner et al. | |
| 2010/0234852 A1 | 9/2010 | Shinohara et al. | |
| 2010/0268204 A1 | 10/2010 | Tien et al. | |
| 2010/0280522 A1 | 11/2010 | Barry et al. | |
| 2011/0021984 A1 | 1/2011 | Kirschenman et al. | |
| 2011/0022149 A1 | 1/2011 | Cox et al. | |
| 2011/0137394 A1 | 6/2011 | Lunsford et al. | |
| 2011/0226379 A2 | 9/2011 | Johnson | |
| 2012/0165919 A1 | 6/2012 | Cox et al. | |
| 2012/0172921 A1 | 7/2012 | Yamanaka et al. | |
| 2012/0197379 A1 | 8/2012 | Laske et al. | |
| 2012/0245614 A1 | 9/2012 | Drasler | |
| 2012/0289988 A1 | 11/2012 | Riina et al. | |
| 2012/0316597 A1 | 12/2012 | Fitz et al. | |
| 2013/0184658 A1 * | 7/2013 | Duncan | A61B 17/1214 604/264 |
| 2014/0004503 A1 * | 1/2014 | Cima | A61F 2/01 435/5 |
| 2014/0114337 A1 | 4/2014 | Fung et al. | |
| 2014/0135799 A1 | 5/2014 | Henderson | |
| 2014/0277097 A1 | 9/2014 | Castleberry et al. | |
| 2015/0148837 A1 * | 5/2015 | Shinar | A61B 17/12109 606/200 |
| 2015/0196301 A1 | 7/2015 | Bodewadt et al. | |
| 2015/0297241 A1 * | 10/2015 | Yodfat | A61B 17/0401 606/194 |
| 2017/0367808 A1 | 12/2017 | Shinar et al. | |
| 2018/0103960 A1 * | 4/2018 | Poulsen | A61B 17/12109 |
| 2019/0167404 A1 | 6/2019 | Shinar et al. | |
| 2019/0269413 A1 * | 9/2019 | Yodfat | A61F 2/01 |
| 2019/0343612 A1 * | 11/2019 | Shinar | A61F 2/01 |

FOREIGN PATENT DOCUMENTS

| | | |
|---|---|---|
| CN | 2017/68049 U | 3/2011 |
| CN | 103313751 A | 9/2013 |

(56) References Cited

FOREIGN PATENT DOCUMENTS

| | | |
|---|---|---|
| DE | 10 2005 010222 A1 | 9/2006 |
| EP | 0121447 | 10/1984 |
| EP | 0865772 A1 | 9/1998 |
| WO | WO 91/04716 | 4/1991 |
| WO | WO 1998/034546 | 8/1998 |
| WO | WO 2004/098420 | 11/2004 |
| WO | WO 2005/051235 | 6/2005 |
| WO | WO 2005/117750 A1 | 12/2005 |
| WO | WO 2006/055443 | 5/2006 |
| WO | WO 2006/084156 | 8/2006 |
| WO | WO 2008/042266 | 4/2008 |
| WO | WO 2008/127328 A1 | 10/2008 |
| WO | WO 2010/134914 A1 | 11/2010 |
| WO | WO 2011/014703 | 2/2011 |
| WO | WO 2012/094251 | 7/2012 |
| WO | WO 2013/179137 | 12/2013 |
| WO | WO 2014/102767 | 7/2014 |
| WO | WO 2014/111911 | 7/2014 |

OTHER PUBLICATIONS

Cousin et al. "Incidence et distribution des thromboses veineusesdes des membres inférieurs diagnostiquées par écho-doppler au décours de prothèses de hanche, de genou et de fractures de hanche. Résultats portant sur 5981 explorations et 2123 thromboses en dix ans" Journal des Maladies Vasculaires, 2011, vol. 36, No. 4, p. 243-253 (English summary).

Decousus et al. "A Clinical Trial of Vena Caval Filters in the Prevention of Pulmonary Embolism in Patients with Proximal Deep-Vein Thrombosis", The New England Journal of Medicine, 1998, vol. 338, No. 7, p. 409-415.

Ouriel et al. "The anatomy of deep venous thrombosis of the lower extremity", Journal of Vascular Surgery, 2000, vol. 31, p. 895-900.

International Search Report and Written Opinion for International Application No. PCT/IB2013/001336 dated Jan. 24, 2014.

International Search Report for International Application No. PCT/IL13/50979 dated Jun. 23, 2014.

International Search Report for International Application No. PCT/IL13/50981 dated Jun. 23, 2014.

Supplementary European Search Report and European Search Opinion, dated Jan. 12, 2016, for European Application No. 13797107.3.

Supplementary European Search Report for European Application No. 13871655.0 dated Oct. 13, 2016.

International Search Report for International Application No. PCT/IL2016/050016 dated Jun. 9, 2016.

International Search Report for International Application No. PCT/IL20 U.S. Appl. No. 17/051,157 dated May 7, 2018.

International Search Report and Written Opinion for International Application No. PCT/IL2017/051157, dated Apr. 6, 2018.

Thors et al. "Resorbable Inferior Vena Cava Filters: Trial in an In-vivo Porcine Model" J Vasc Interv Radiol 2011, vol. 22, No. 3, Mar. 2011, 330-335.

Supplementary European Search Report issued for EP 17862315, dated Mar. 25, 2020.

* cited by examiner

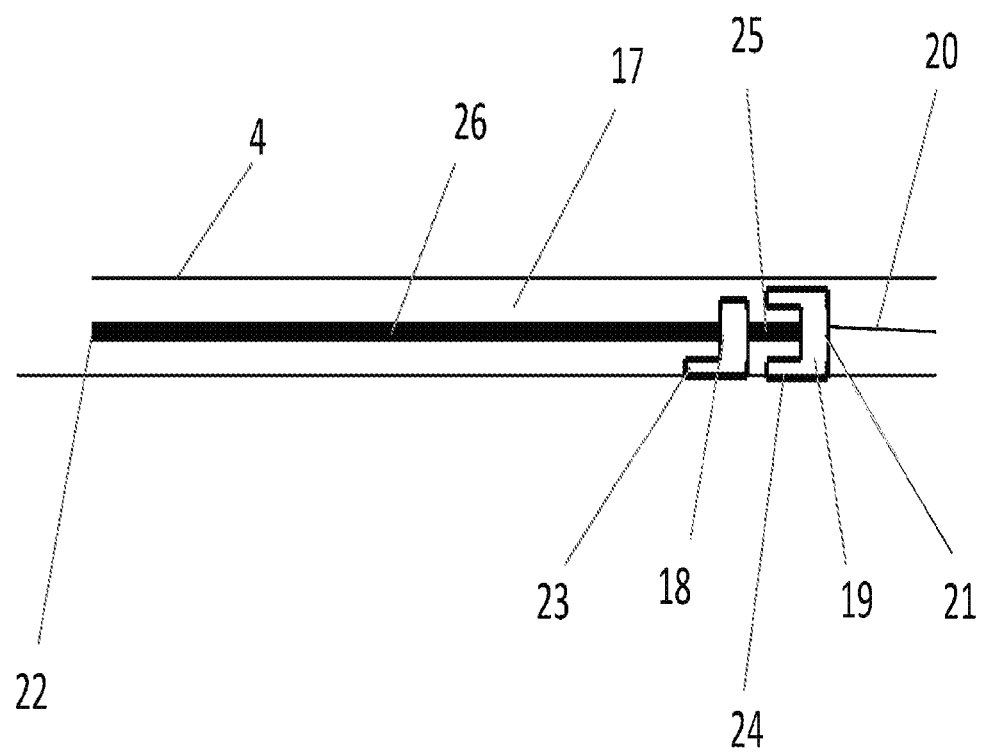

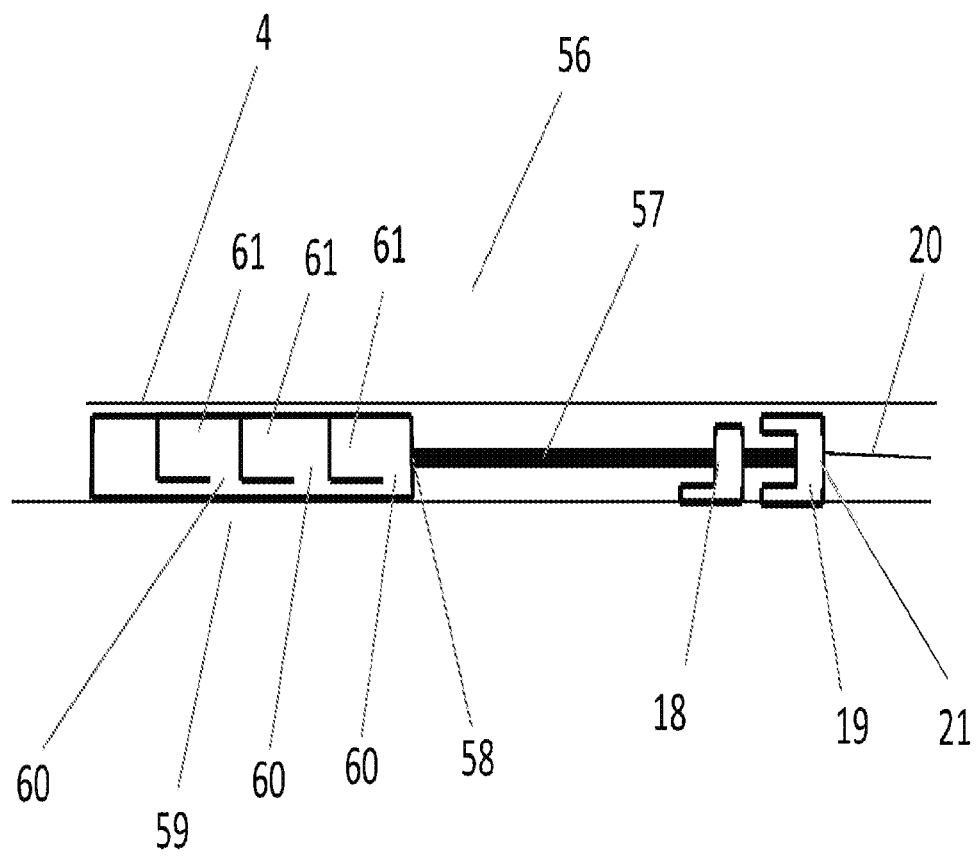

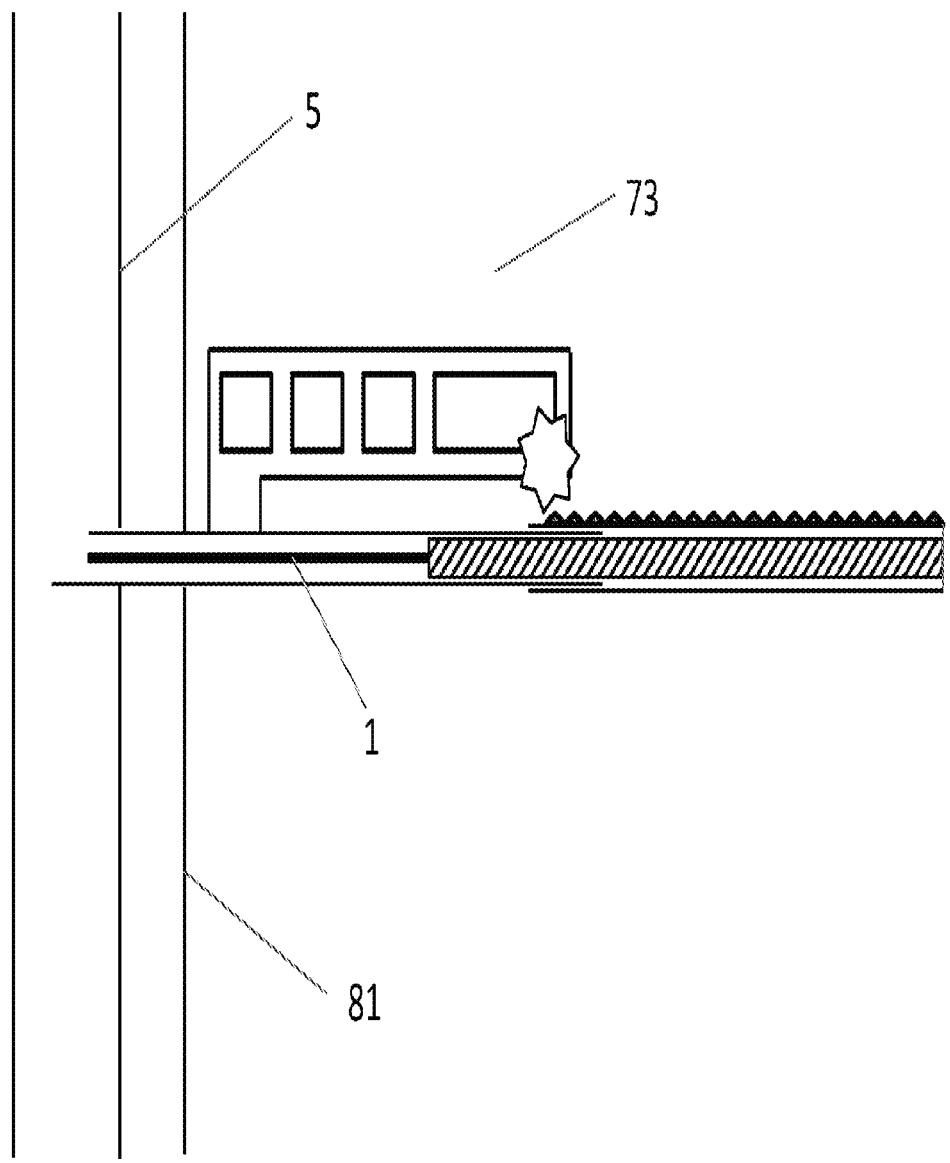

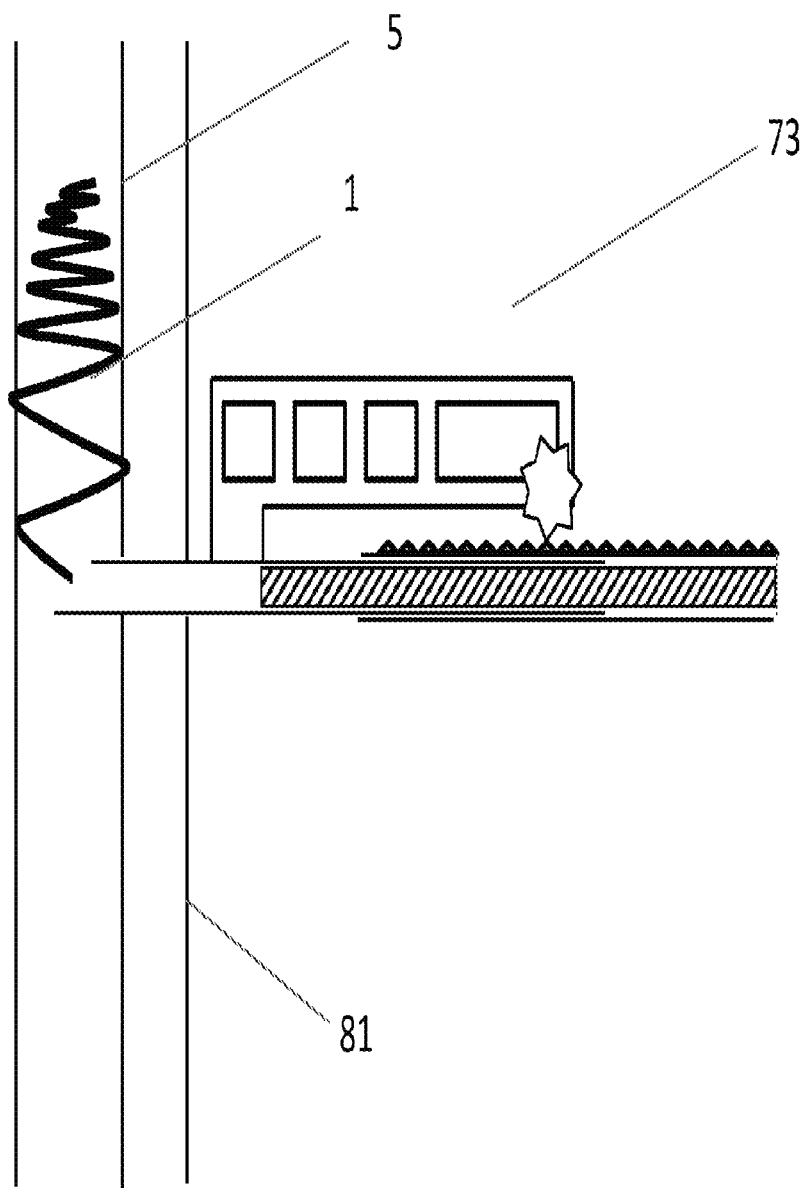

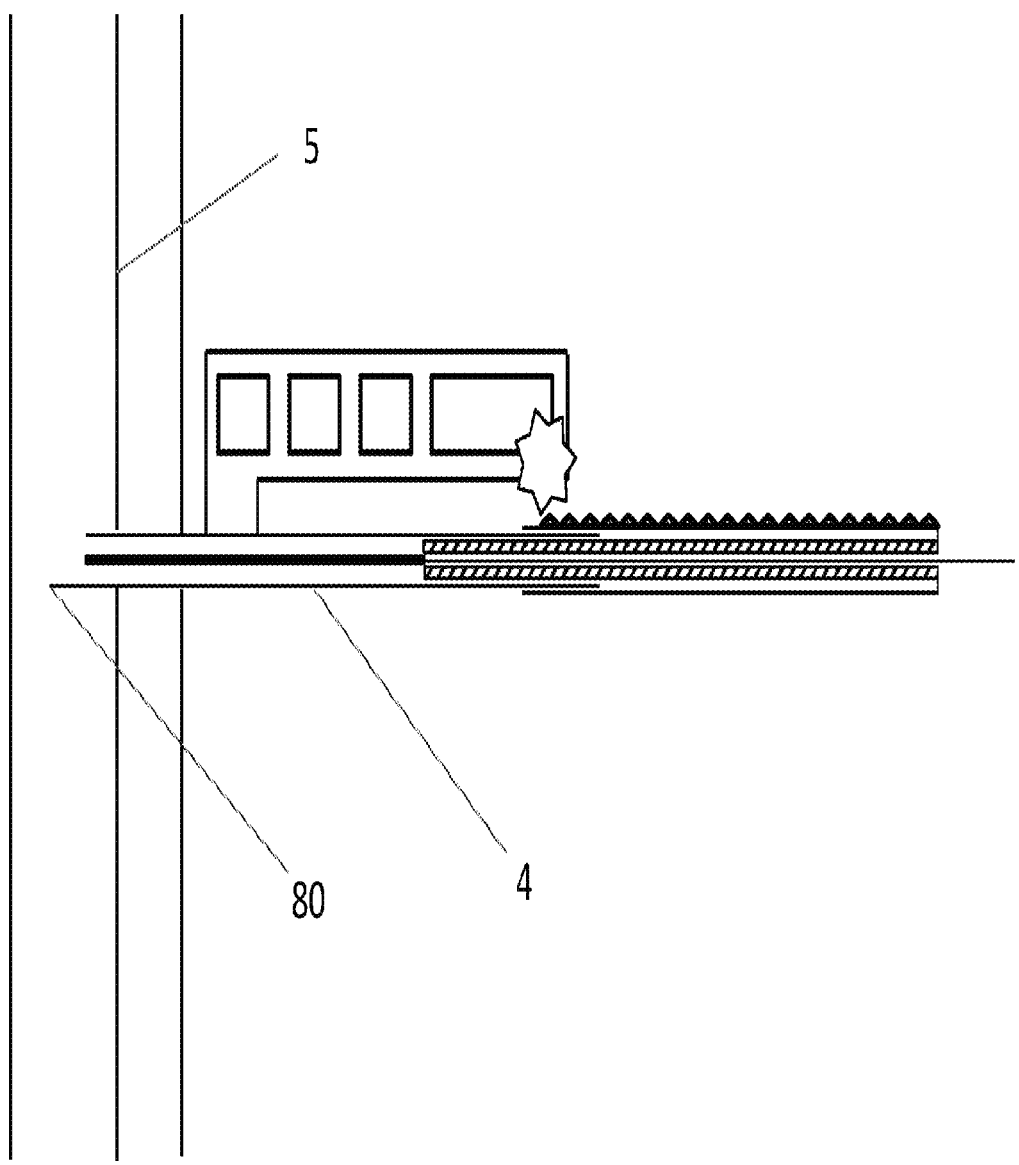

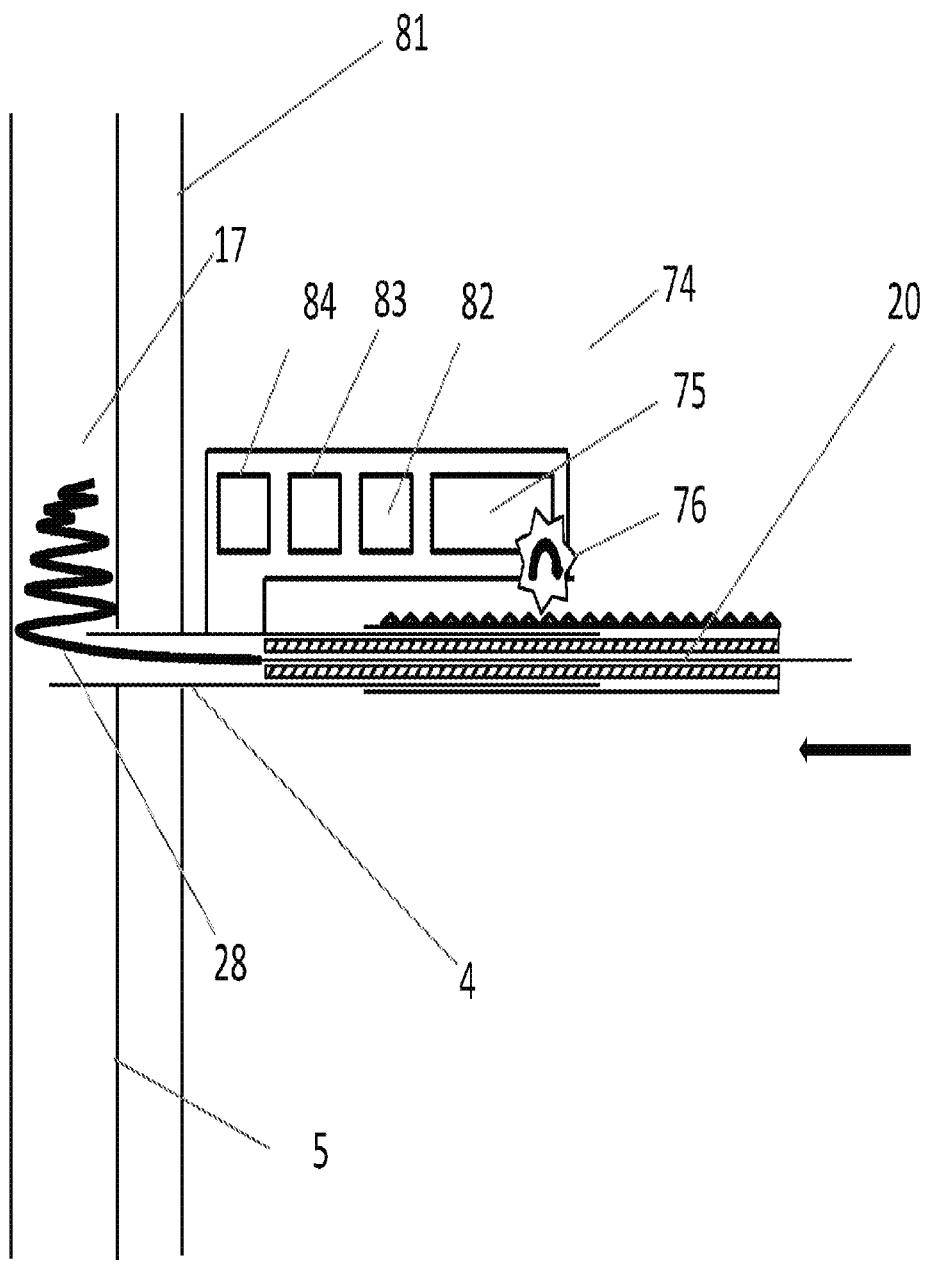

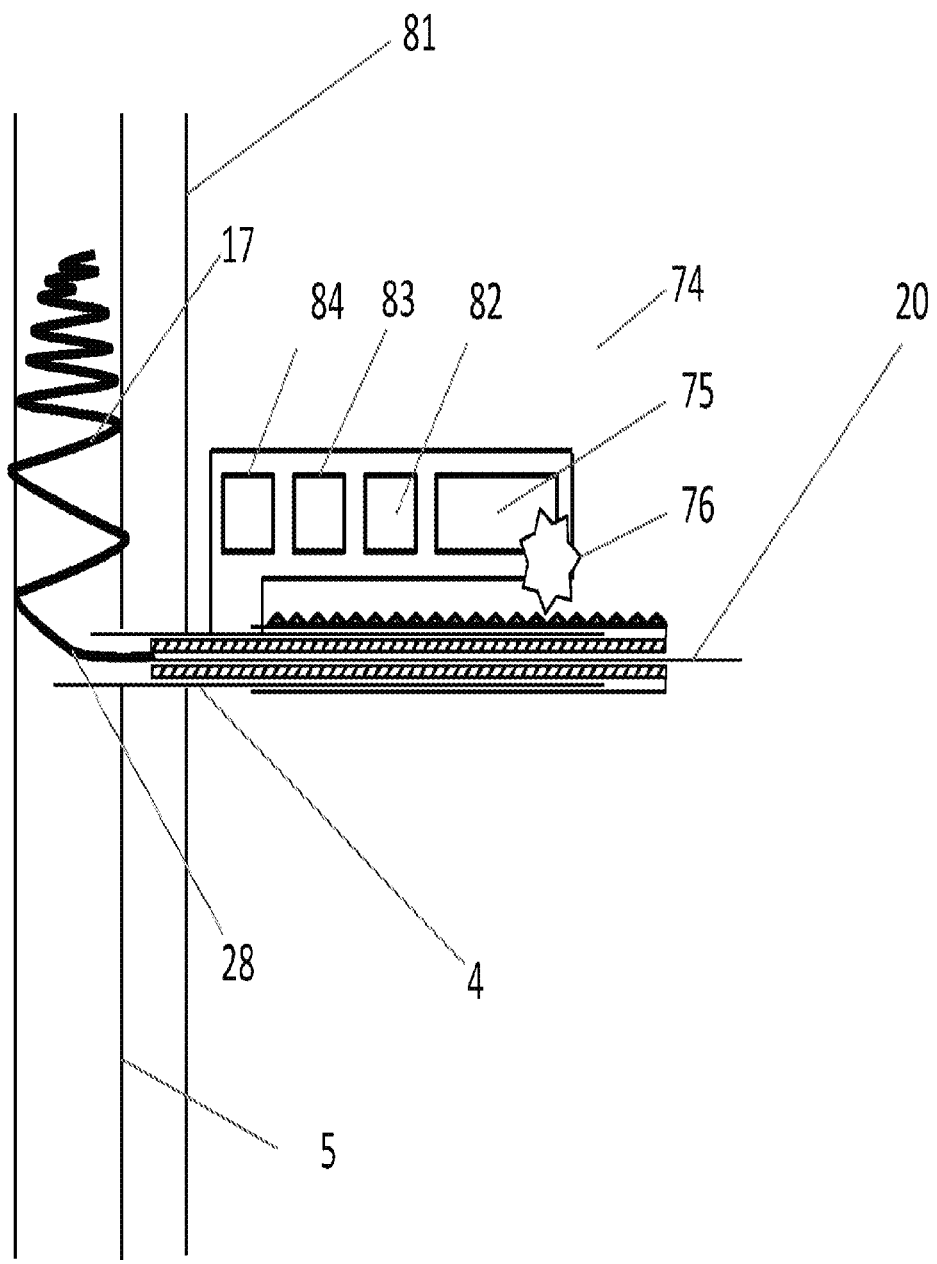

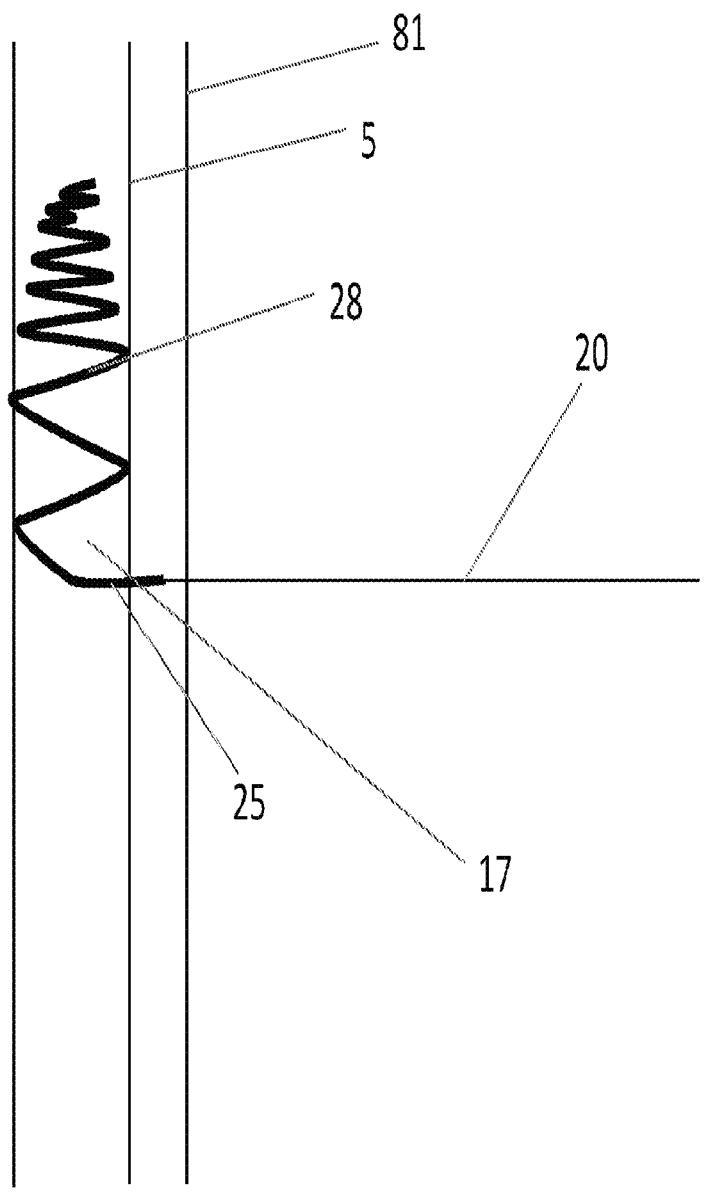

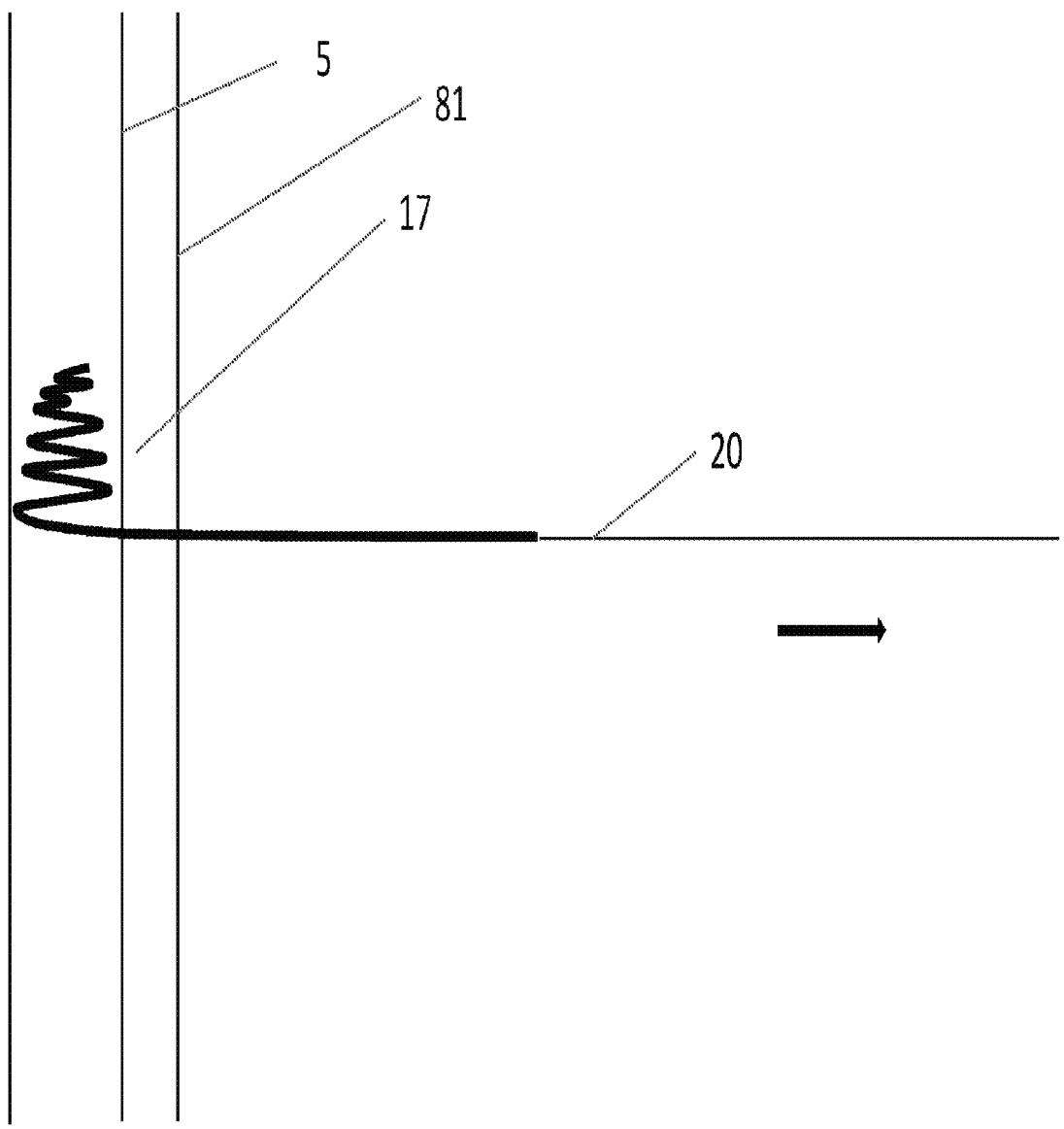

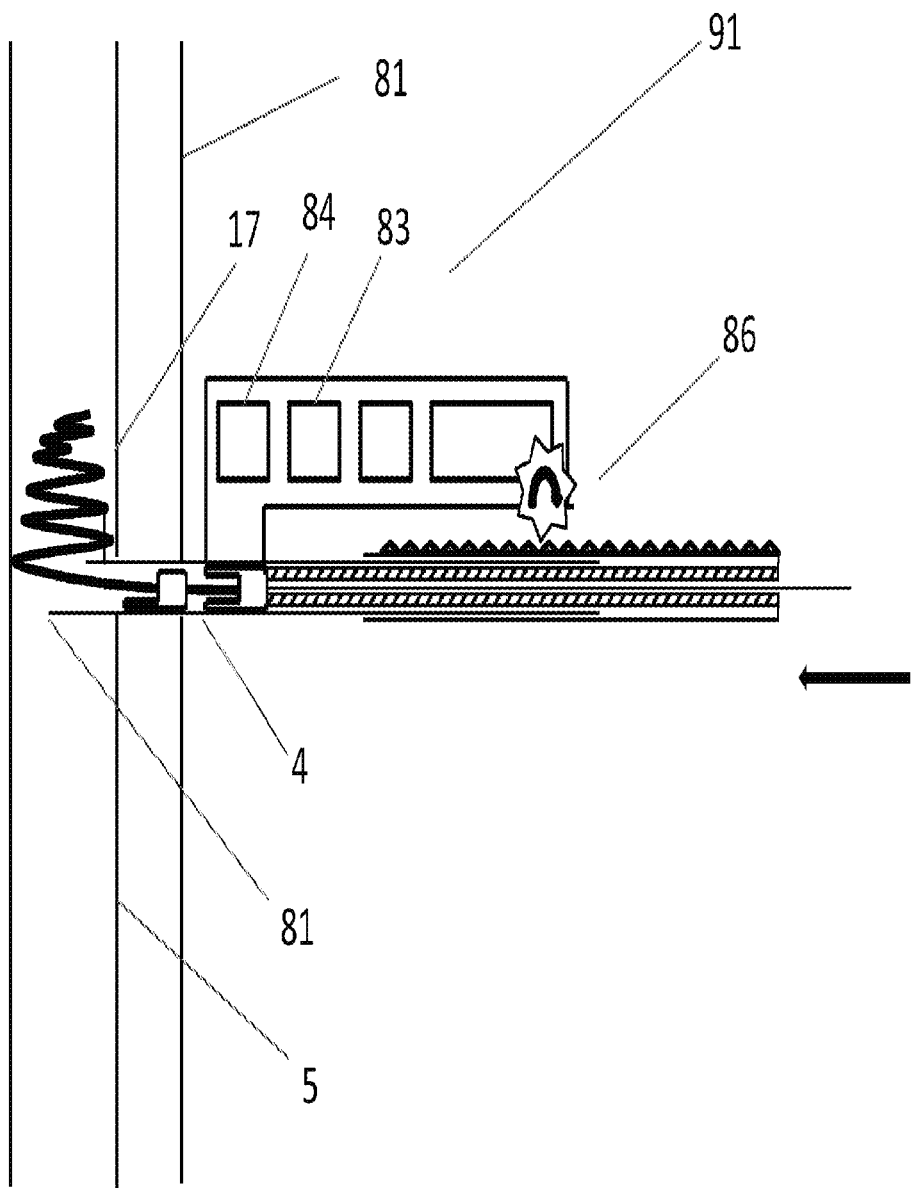

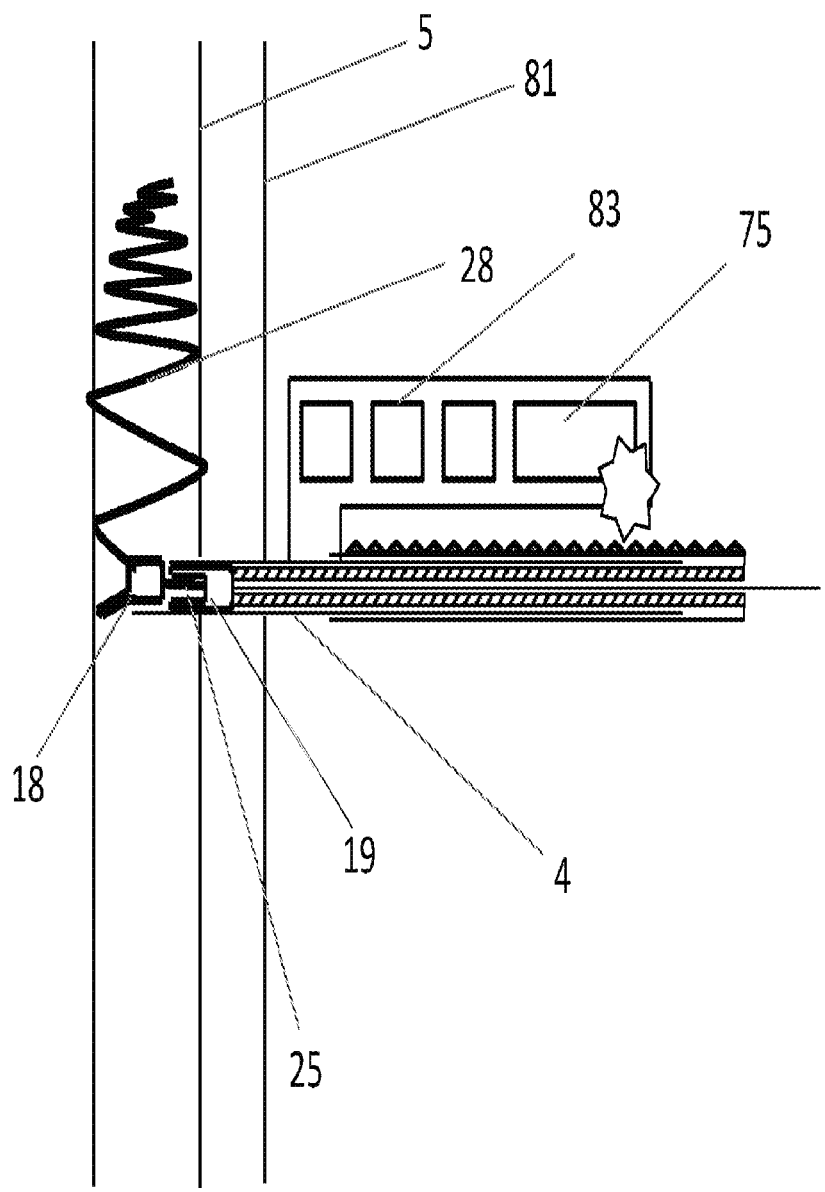

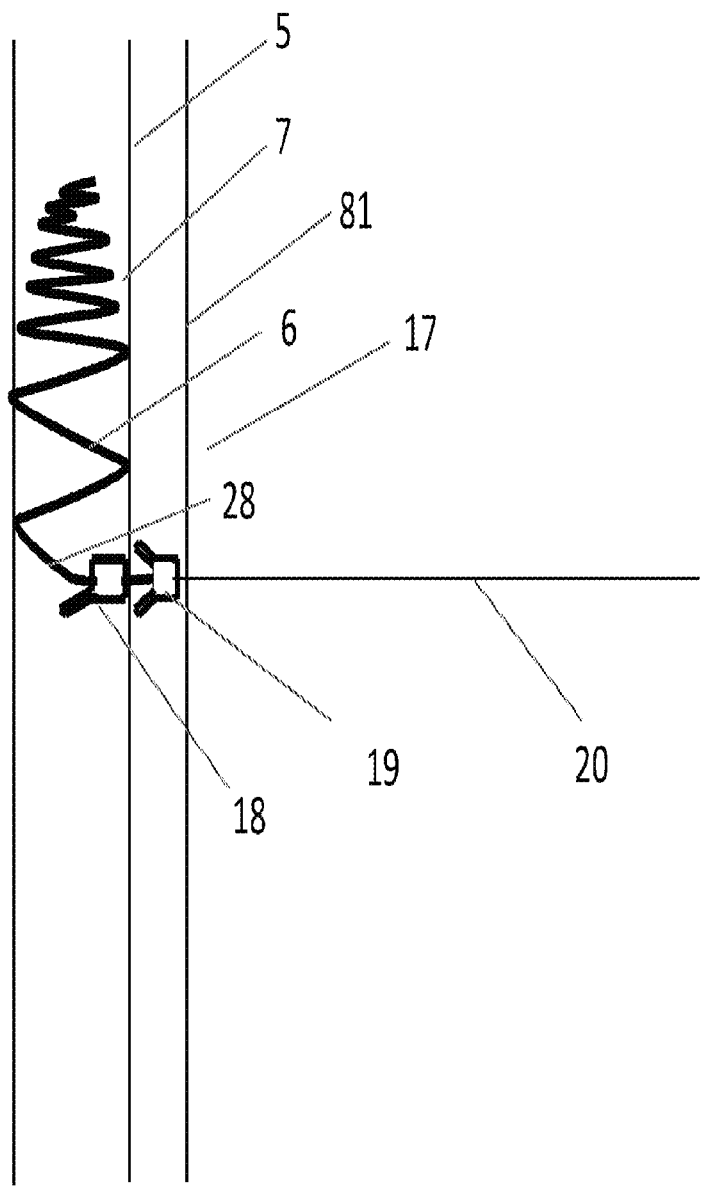

FIG 18A
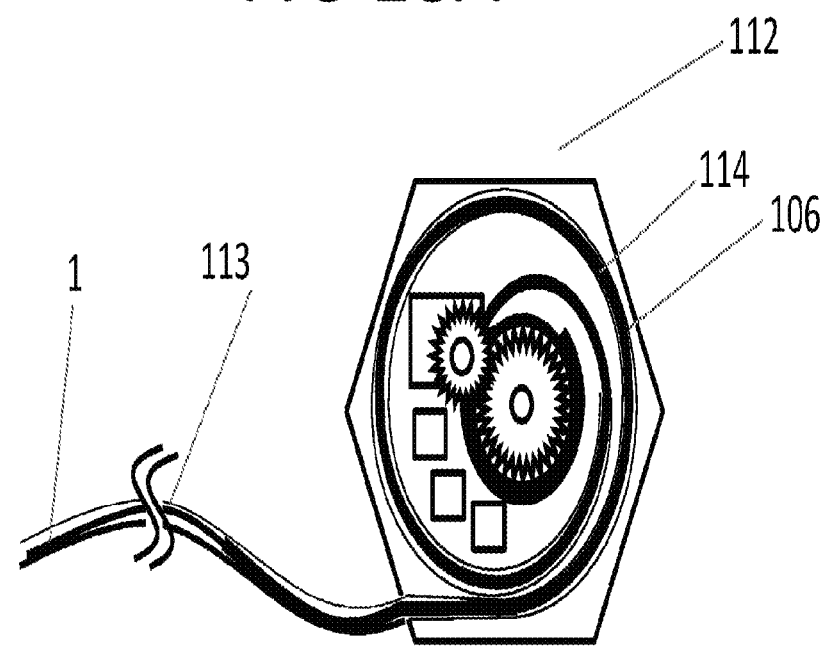
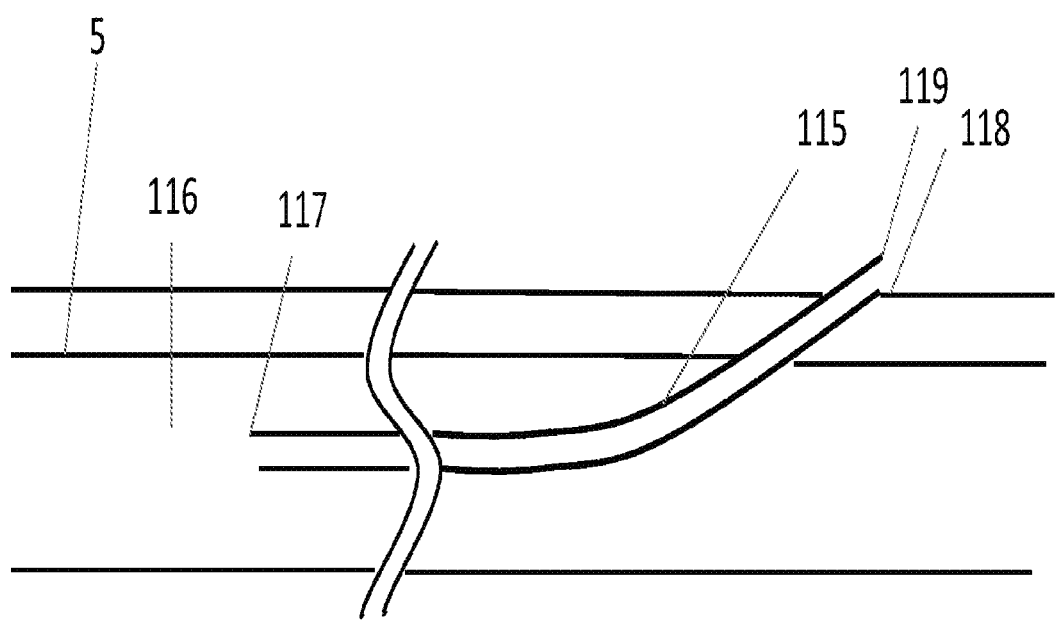

SYSTEMS, METHODS AND DEVICES FOR EMBOLIC PROTECTION

This application is a national stage entry of, and claims priority to, International Patent Application No. PCT/IL2017/051157, filed Oct. 20, 2017, entitled "System and Method for Embolic Protection," which in turn claims priority benefit of U.S. provisional patent application nos. 62/411,353, filed Oct. 21, 2016, and 62/471,676, filed Mar. 15, 2017, and is also related to PCT application nos. PCT/IB2013/001336, filed 30 May 2013, PCT/IL2013/050979, filed 27 Nov. 2013, PCT/IL2013/050981, filed 27 Nov. 2013, and PCT/IL2016/050016, filed 6 Jan. 2016, and U.S. patent application Ser. No. 14/563,513, filed Dec. 8, 2014. Each of these noted disclosures, in its entirety, is herein incorporated by reference.

RELATED APPLICATIONS

This application claims priority benefit of U.S. provisional patent application No. 62/411,353, filed Oct. 21, 2016, and 62/471,676, filed Mar. 15, 2017, and is also related to PCT application nos. PCT/IB2013/001336, filed 30 May 2013, PCT/IL2013/050979, filed 27 Nov. 2013, PCT/IL2013/050981, filed 27 Nov. 2013, and PCT/IL2016/050016, filed 6 Jan. 2016, and U.S. patent application Ser. No. 14/563,513, filed Dec. 8, 2014. Each of these noted disclosures, in its entirety, is herein incorporated by reference.

FIELD OF THE DISCLOSURE

The field of the present disclosure is embolic protection devices. More specifically, the field of the present disclosure is embolic protection for the prevention of brain stoke and/or pulmonary embolism.

BACKGROUND

Embolism is the event of lodging of an embolus (a detached intravascular mass) into a narrow vessel, which causes a blockage in a distant part of the body. Embolism can be classified as to whether it enters the circulation in arteries or veins. Arterial embolism can start in the heart or in large arteries, and can cause occlusion and/or infarction in any part of the body. Embolus lodging in the brain from either the heart or the carotid arteries can cause an ischemic stroke. Venous embolism, which forms in systemic veins, can lodge in the lungs after passing through the right side of the heart. This deleterious condition is known as pulmonary embolism.

Distal embolization can occur spontaneously or be induced by manipulation of the heart, large arteries, or veins, either in the setting of open surgery, or in the setting of endovascular manipulation such as balloon angioplasty or stenting.

SUMMARY OF SOME OF THE EMBODIMENTS OF THE DISCLOSURE

Accordingly, embodiments of the present disclosure may be used to address embolism events in blood vessels of the body.

In some embodiments, an embolic protection device ("EPD", "device" or "filtering device") is provided which includes a proximal end and a distal end, as well as an un-deployed state and a deployed state.

In some embodiments, an EPD is provided and comprises a wire or a filament, which may be made of a super-elastic alloy (e.g., nitinol). The device, which has a proximal and a distal end, may assume two states—a constrained, un-deployed state (which may be linear, substantially linear, non-linear, or a combination), and an expanded, deployed state, in which the filament may be wound or coiled (such terms may be used interchangeably). The coiled deployed shape may include a support portion, which is shaped as a helix, and a filter portion.

In some embodiments, the support portion may include at least one elongated coil whose height, or pitch, is greater than the coil diameter. Such an elongated coil is configured to resist axial compression of the support portion: as the elongated coil is compressed, its diameter grows, and support from the vessel walls, which opposes further compression, is therefore generated. In some embodiments at least one coil of the support portion may be oversized by 0.1-2.0 mm compared to the target vessel diameter.

The filter portion may include a portion shaped as a funnel (e.g., coils of the helix which taper) and a reducing element configured to reduce the aperture of the largest opening in the funnel portion (which is the smallest coil in the funnel). In some embodiments, the reducing element may be integral with the filament. In some embodiments, the reducing element may include at least one coil that is off the axis of the helical support portion. In some embodiments the reducing element may be shaped as a rod, a zig-zag, a curve, or a ring with inward protrusions.

In some embodiments, the deployed shape of the filament may include a stem portion at the proximal end. The stem portion, which may be linear, may be configured to traverse the vessel wall.

In some embodiments, the device may include a stopper attached near the proximal filament end. The stopper may prevent movement of the filament from within the vessel lumen outwards. In some embodiments, the device may include an anchor configured to engage tissue externally to the vessel lumen. In some embodiments the anchor may be rotatable around the stem.

In some embodiments, the device may include a pull wire configured to extend outside the patient's skin following device deployment. The pull wire may be used to retrieve the device through the vessel wall. In some embodiments, the pull wire may be configured with a bearing.

In some embodiments, the device may be implanted within a blood vessel using a delivery system comprising a rigid needle (which in some embodiments may be referred to also as a "tube", or a "cannula" both terms being used interchangeably, at least with respect to some embodiments, throughout) having an outer diameter of less than about 0.5 mm (about 1.5 French, 0.02") and a sharp distal end. The device may be preassembled within the needle and positioned at the distal end, where it may be constrained to assume its un-deployed. A pusher, in a form of an elongated rod, may also be preassembled within the needle, extending from the proximal end of the needle to the proximal end of the device. The implantation of the device may be performed by piercing the skin and underlying tissues and advancing the needle into a vessel under ultrasound guidance. Within in the vessel the device may be exteriorized from the needle by pushing the pusher. After exteriorization of the device from the needle, the device may assume the expanded deployed state such that the distal end resides within the vessel lumen and the proximal end resides within or outside the vessel wall. In some embodiments, the axis of the helical support portion is arranged approximately parallel to the fluid flow within the vessel.

In some embodiments, the pusher may be driven using an electromechanical system comprising a driving mechanism, a controller, a power supply, and an input/output device. The driving mechanism may include a motor, a gear and a rack. An operator may cause the device to be exteriorized from the needle by providing a suitable input to the input/output device. Upon receipt of the input signal, the controller may direct power from the power supply to the driving mechanism, thereby causing the pusher to push the device out of the needle.

In some embodiments, the pusher may be driven using an electromechanical system comprising a driving mechanism, a drum, a controller, a power supply, and an input/output device. The driving mechanism may include a motor, a pinion and a spur. The spur may be rigidly connected to the drum, and the proximal end of the pusher may be connected to the drum. An operator may cause the device to be exteriorized from the needle by providing a suitable input to the input/output device. Upon receipt of the input signal, the controller may direct power from the power supply to the driving mechanism, thereby causing the pinion to rotate in one direction, the spur and the drum to rotate in the opposite direction, the pusher to push the device out of the needle.

In some embodiments, the needle or a portion thereof may be interchanged for a flexible tube configured to be delivered to the implantation site in transcatheter fashion. In some embodiments, the pusher may be hollow and configured to receive the pull wire in its lumen.

In some embodiments, an embolic protection device (EPD) is provided which is configured for arrangement within a blood vessel. The EPD include a filament configured to have an un-deployed state including a portion configured to fit within a lumen of a needle or a tube, and a deployed state, where the filament automatically forms a helix comprising a support portion and a filter portion. The support portion may include a first portion of the helix having an axis, which comprises an elongated coil having a height which exceeds a diameter thereof. The filter portion includes a funnel configured to taper in a first direction, and the funnel also includes at least one reducing coil having a center which is off the axis. The support portion is configured to at least one of orientate the filter portion within a blood vessel and secure the EPD relative to the blood. At least a portion of the elongated coil may be configured to resist axial compression of the support portion, and the reducing coil may be configured to capture emboli greater than a predetermined size. Such embodiments (as well as other embodiments), may also include one and/or another of the following features, functionality, and/or clarification, yielding yet other further embodiments of the present disclosure:
  the deployed shape further comprises a stem configured to traverse the vessel wall;
  a pull wire configured traverse a patient's skin and enable retraction of the device by pulling the device out of the vessel;
  a stopper configured to prevent the filament from moving from the vessel lumen outwards through a puncture in the vessel;
  an anchor configured to engage tissue externally to the vessel lumen;
  a second support portion whereby the filter portion is interposed between the support portion and the second support portion;

a second reducing coil whose center is off the axis;
  a line segment connecting the centers of the reducing coil and the second reducing coil intersects the axis;
  the filament is made from nitinol; and/or
  the filament cross section is round, and the diameter of the cross section is in the range of 0.05 and 0.3 mm.

In some embodiments, a system for providing embolic protection in a patient is provided and includes an embolic protection device (EPD), a needle, a pusher, a driving mechanism, a control unit, a power supply, and an input/output device. A proximal end of the EPD may be initially arranged within the lumen of the needle, a distal end of the pusher may be initially arranged within the lumen of the needle and proximally to the proximal end of the EPD, upon an operator instruction through the input/output EPD, the controller can be configured to cause the pusher to push at least a portion of the EPD out of the needle lumen by means of the power supply and the driving mechanism. The EPD may comprise any of the EPD embodiments disclosed in the present application.

In some embodiments, a system for providing embolic protection in a patient is provided, where the system includes an embolic protection device (EPD), a needle, a pusher having a hollow lumen, a driving mechanism, a control unit, a power supply, and an input/output device. A proximal end of a filament of the EPD may be initially arranged within the lumen of the needle, the distal end of the pusher may be initially arranged within the lumen of the needle and proximally to the proximal end of the EPD, at least a portion of a pull wire of the EPD may be arranged within the lumen of the pusher, and upon an operator instruction through the input/output EPD, the controller may be configured to cause the pusher to push at least a portion of the EPD out of the needle lumen by means of the power supply and the driving mechanism. The EPD may comprise any of the EPD embodiments disclosed in the present application.

In some embodiments, an embolus capturing method is provided and includes puncturing a wall of a blood vessel transcutaneously with an end of a needle, where the needle including a lumen housing at least a portion of an embolic protection device (EPD). The EPD may comprise a filament configured to include an un-deployed state having a portion configured to fit within a lumen of a needle or a tube, and a deployed state whereby the filament automatically forms a helix comprising a support portion and a filter portion. The support portion may include a first portion of the helix which includes an axis, and may comprise an elongated coil having a height which exceeds a diameter thereof. The filter portion may include a funnel configured to taper in a first direction, the funnel also including at least one reducing coil having a center which is off the axis. The method may further include directing the distal tip through the skin and into a blood vessel and deploying the filament from the needle. The filament thereby forms the deployed state, and the axis preferably aligns at least approximately with the direction of the flow of blood in the vessel. The method may further include removing the distal tip from the blood vessel and skin. The EPD of such embodiments may include a stem, and the method may further include arranging the stem to lie within or traverse the vessel wall. Moreover, in some embodiments, the method may also include arranging at least one of an anchor, a pull wire, and a stopper with the filament during or after deployment.

In some embodiments, an embolic protection system for providing embolic protection in a patient is provided and includes a needle (which may include a curved portion), an EPD including a monofilament, where the EPD includes an un-deployed shape whereby a portion of the monofilament is configured to fit within the lumen of the needle, and a deployed shape whereby the monofilament has at least one curve. The system may further include a pusher, a driving mechanism, a control unit, a power supply, and an input/output device. In some such embodiments, the proximal end of the EPD may be initially arranged within the lumen of the needle and the distal end of the pusher may be initially arranged within the lumen of the needle and proximally to the proximal end of the EPD. Upon an operator instruction through the input/output device, the controller may be configured to cause the pusher to push at least a portion of the EPD out of the needle lumen by means of the power supply and the driving mechanism. The speed with which the EPD is pushed out of the needle, in some embodiments, is less than about 2 cm/sec.

In some embodiments, an embolic protection device (EPD) configured for arrangement within a blood vessel is provided and includes a filament having an un-deployed state comprising a portion configured to fit within a lumen of a needle or a tube, and a deployed state comprising a support portion and a filter portion. The support portion may be shaped as a helix having an axis, where the helix includes at least a portion of a coil of the helix whose height exceeds its diameter. At least one coil of the helix can include a diameter which exceeds the diameter of the vessel for which the EPD is placed. The filter portion can comprise a plurality of coils having diameters which decrease in the direction towards the proximal or the distal end of the EPD. The EPD can also include a reducing element comprising at least one reducing coil of the helix whose center is off the helix axis. The diameters of the plurality of tapering coils and the at least one reducing coil, in some embodiments, is smaller than the diameter of the artery.

In some embodiments, an embolic protection implantation system for implanting an embolic protection device (EPD) within a vessel of the body is provided and includes a housing, and a needle having a lumen. The needle may be configured to at least one of house, at least partially, and guide an EPD into a vessel of the body of a patient. The system may further include a pusher configured to push or otherwise move at least the EPD relative to the needle, and a driving mechanism configured to move at least one of the pusher and the EPD so as to deploy the EPD into the vessel. Such embodiments (as well as other embodiments), may also include one and/or another of the following features, functionality, and/or clarification, yielding yet other further embodiments of the present disclosure:

- an EPD configured to assume an un-deployed shape including a curved portion;
- the driving mechanism comprises at least one of a motor, a pinion, a spur, and a planetary gear;
- the needle is connected to the housing;
- the needle includes a straight portion and a curved portion;
- at least part of the straight portion of the needle may be arranged externally to the housing, and/or at least part of the curved portion may be arranged within the housing;
- the curved portion of the EPD may include one or more coils or turns;
- a drum;
- an axle configured to enable the drum (see above) to rotate thereon, where the axle may be connected to the housing;
- a spur which may be connected to the drum (see above);
- the un-deployed state of the EPD is inherited from the configuration of the needle;
- the EPD is at least partially housed within the lumen of the needle;
- at least one of: a power supply, a controller, and an input and/or output device;
- at least part of the pusher may be housed within the lumen of the needle;
- the pusher may be configured to initially reside external to the lumen of the needle;
- a distal end of the pusher may be arranged proximally to a proximal end of the EPD;
- a proximal end of the pusher may be connected to the drum (see above);
- the pusher may configured to extend towards a proximal end of the needle through guides or channels;
- the pusher may include a lumen or may be solid;
- the pusher may include a lumen, and a pull wire of the EPD may be arranged within the lumen of the pusher;
- a proximal end of a pull wire may protrude proximally from a proximal end of the pusher;
- rotation of the driving mechanism in a first direction may effect rotation of the drum in a second direction;
- the input/output device may comprise at least a button for operating the system;
- the system may include a first part configured to be disposable and a second part configured to be reusable, whereby the reusable part includes one or more of the housing, an input/output device, a controller, a power supply, and all or portions of the driving mechanism, the disposable part may include one or more of the needle, the embolic protection device, and at least a portion of the driving mechanism; and the reusable and disposable parts may be reversibly connected with each other;
- at least one of an LED or audio output device, whereby one and/or another may be configured to indicate that the EPD is fully exteriorized from the needle;
    fully exteriorized does not, in some embodiments, include exteriorization of one or more of a stem, an anchor, and a pull wire of the EPD;
- at least a portion of the needle comprises a flexible tube;
- the flexible tube may comprise at least one of nitinol and polymer, whereby the distal portion of the needle may comprise the flexible tube, such that the tip of the needle may be flexible;
- a catheter configured to provide transcutaneous access to the lumen of a blood vessel proximate an entry site on the skin of a patient; and/or
- the flexible tube (see above) may be configured with a curved portion and a distal end configured to puncture the wall of the vessel such that the distal end can optionally pierce the vessel from inside to outside;

In some embodiments, an embolic protection device (EPD) implanting system for implanting an embolic protection device (EPD) within a vessel of the body is provided, which includes a housing, a flexible tube having a lumen, where the flexible tube may be configured to at least one of house, at least partially, and guide an EPD into a vessel of the body of a patient, a pusher configured to push or otherwise move at least the EPD relative to the flexible tube, a drum, and a driving mechanism configured to move at least one of the pusher, the drum, the flexible tube and the EPD so as deploy the EPD into the vessel.

In some embodiments, an embolic protection device (EPD) implanting method for implanting an embolic protection device (EPD) into a vessel is provided which includes providing an EPD implanting system, whereby at least a portion of a needle configured to aid in the implantation of an EPD comprises a flexible tube, providing a catheter, piercing the skin of a patient at an entry site, the entry site being proximate a blood vessel of a patient, and arranging the catheter relative to the patient such that a distal end thereof is placed adjacent an implantation site within the lumen of the blood vessel and a proximal end thereof protruding outside the skin at the entry site. The method may also include guiding the flexible tube into the lumen of the catheter through the proximal end thereof until a distal end of the flexible tube is arranged at or near the implantation site within the blood vessel, deploying the EPD at or near the implantation site, withdrawing the flexible tube and leaving the EPD at the implantation site, and/or withdrawing the catheter. In such method embodiments, the EPD implanting system may be that according to any of the EPD implanting systems disclosed herein.

In some embodiments, a embolic protection device (EPD) implanting method for implanting an embolic protection device (EPD) is provided which includes providing an EPD implanting system, providing a catheter, piercing the skin of a patient at an entry site, the entry site being proximate a blood vessel of a patient, arranging the catheter relative to the patient such that a distal end thereof is placed adjacent an implantation site within the lumen of the blood vessel and a proximal end thereof protruding outside the skin at the entry site, guiding the flexible tube into the lumen of the catheter through the proximal end thereof until a distal end of the flexible tube is arranged at or near the implantation site within the blood vessel, deploying the EPD at or near the implantation site, withdrawing the flexible tube and leaving the EPD at the implantation site, and/or withdrawing the catheter.

The term "substantially," according to some embodiments, may be defined as near or proximate or about equal to, for example, a total amount, boundary or structure (and the like). In some embodiments, the term "substantially" may be defined as "essentially" (for example).

In some embodiments, a vascular embolic protection device for deployment at an implantation site within a blood vessel is provided and may include a filament having a length, proximal and distal ends and a diameter between about 0.025 mm and about 1 mm (and in some embodiments, between about 0.05 and 0.3 mm, for example), and is configured to include an un-deployed state and a deployed state. In the un-deployed state, at least a portion of the device is configured to fit within the lumen of a delivery tube or needle, and in the deployed state, the device includes an axis which is approximately parallel to the fluid flow in a blood vessel

BRIEF DESCRIPTIONS OF THE FIGURES

A detailed description of some embodiments may be better understood by reference to the following figures.

Figure 2A:
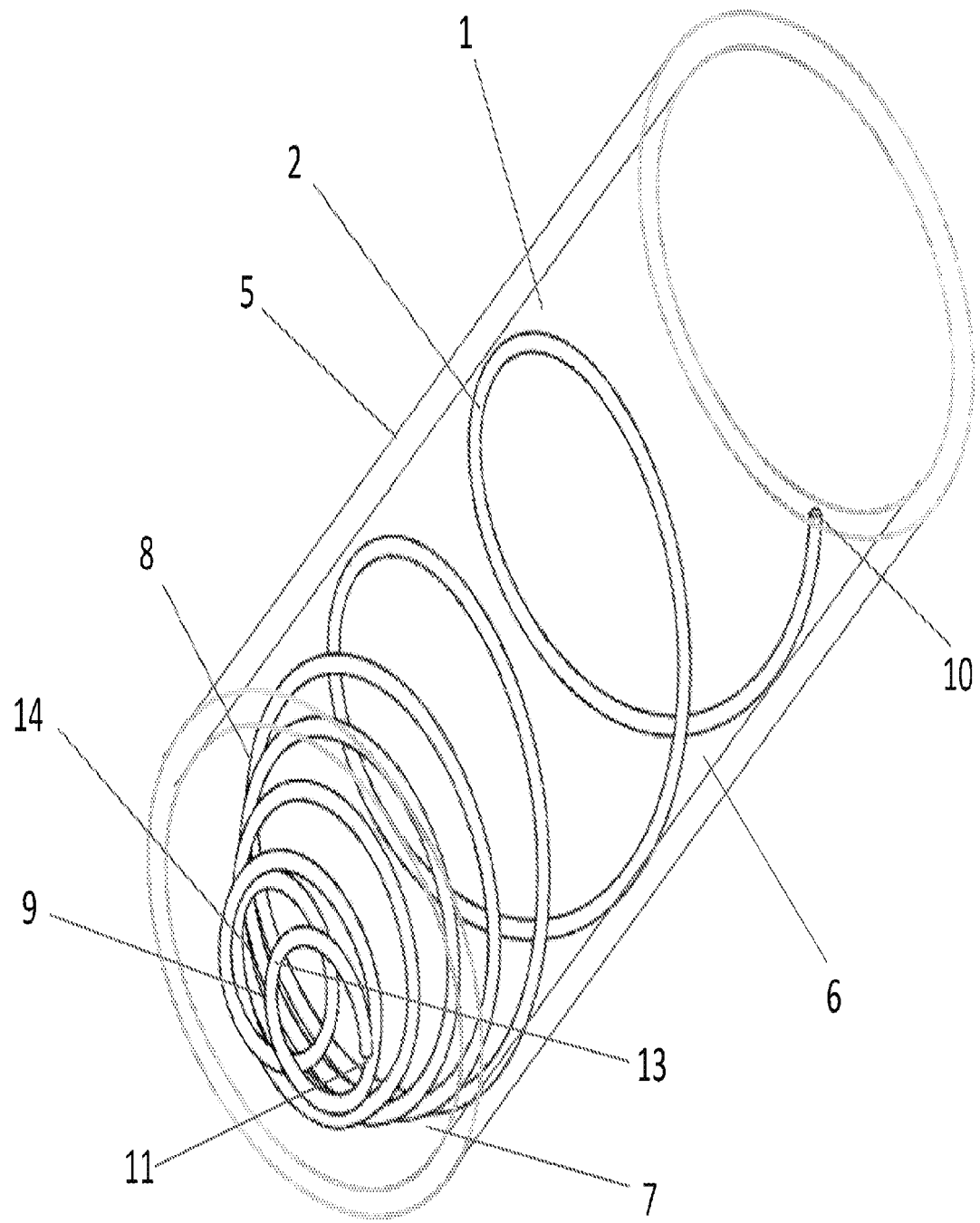
Figure 2B:
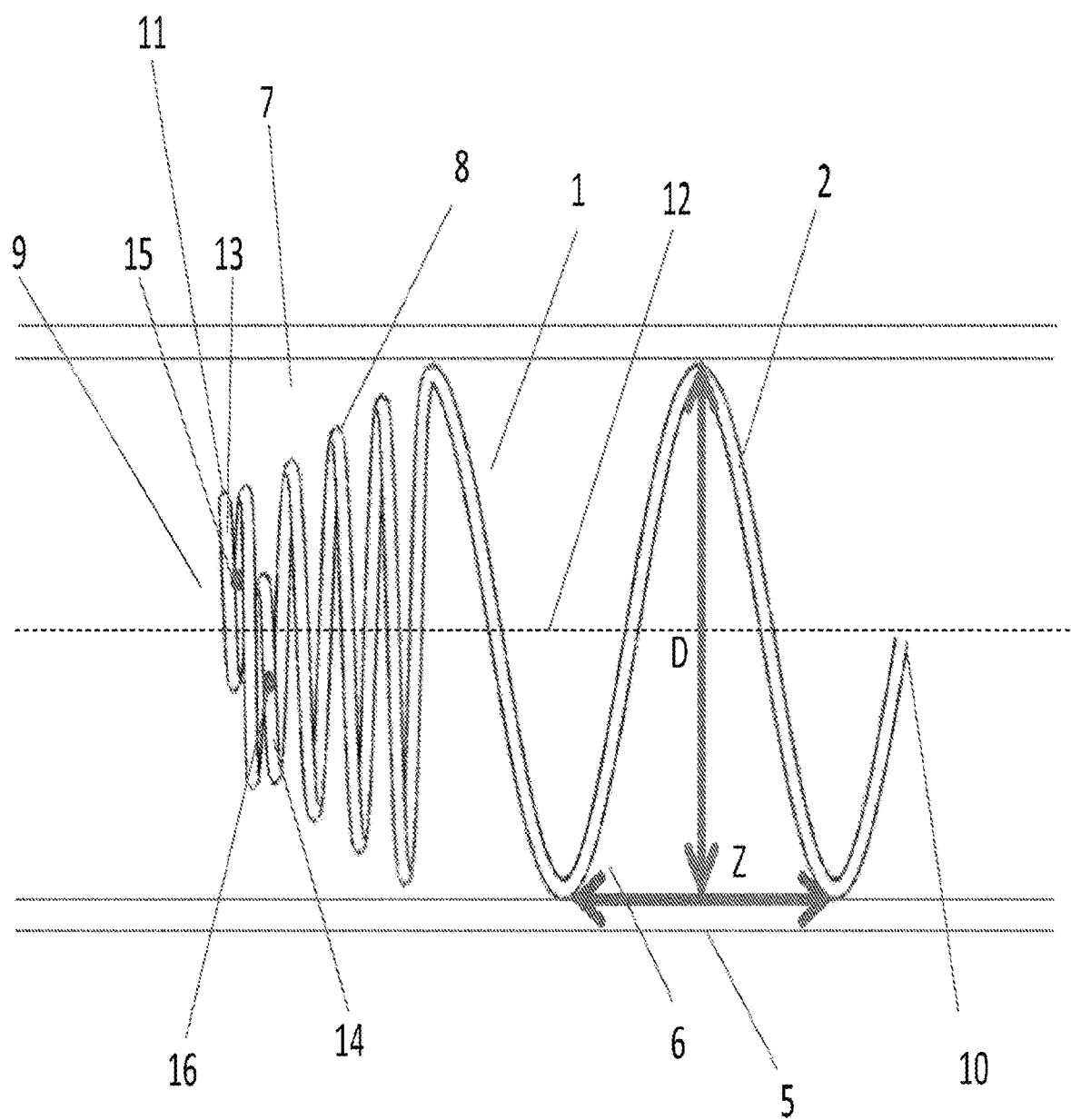
Figure 2C:
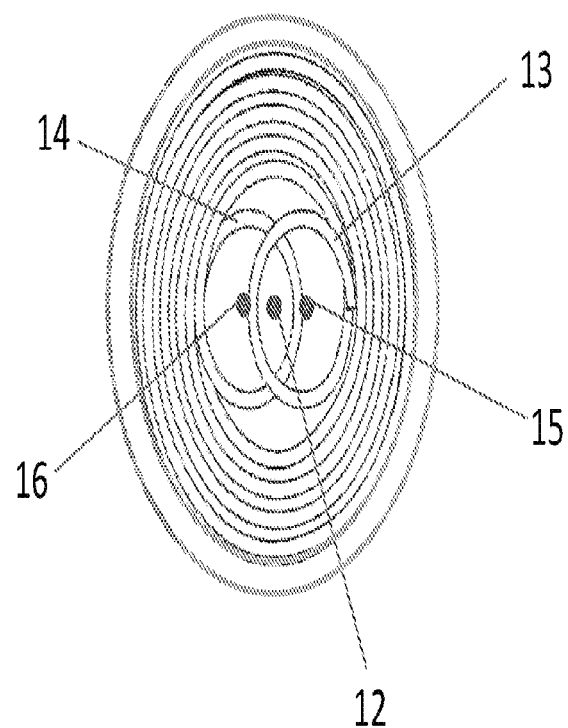

FIGS. 2A-C depict isometric, side, and front views of the deployed state of an embolic protection device including (e.g.) two off-axis reducing coils according to some embodiments.

FIG. 3 depicts an un-deployed state of an embolic protection device including two off-axis reducing coils, a stem, a stopper, an anchor, and a pull wire according to some embodiments.

Figure 4A:
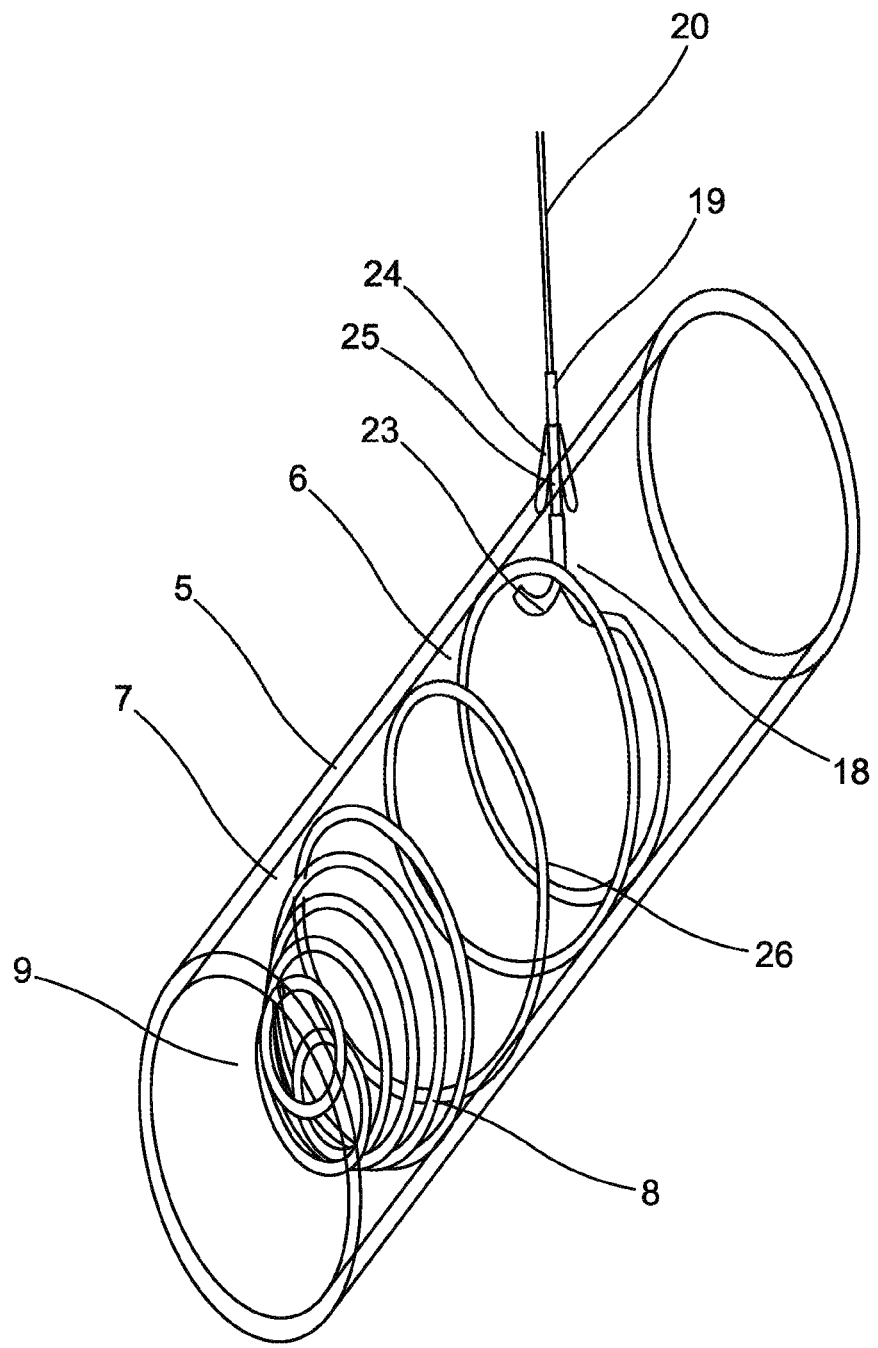
Figure 4B:
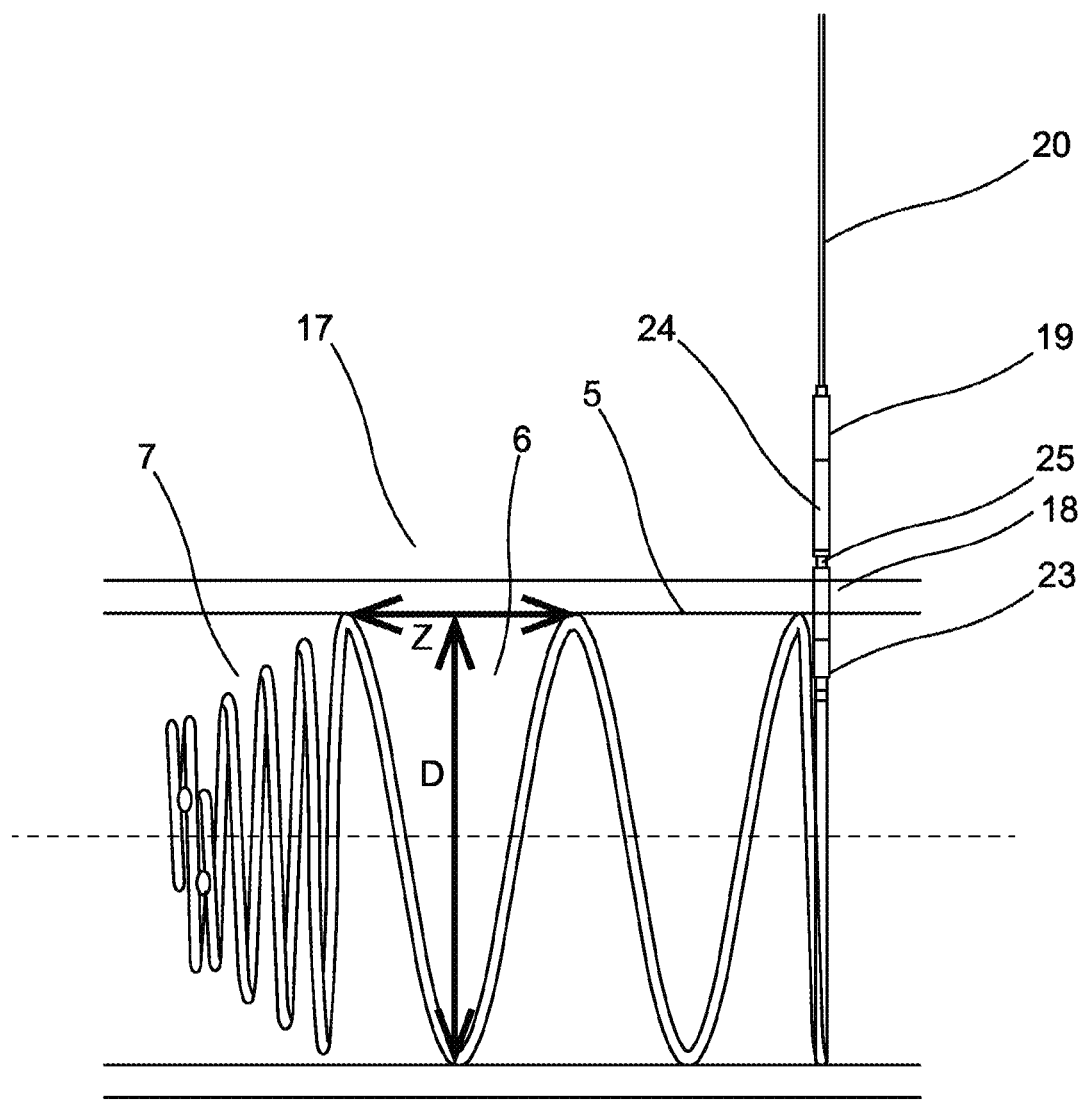
Figure 4C:
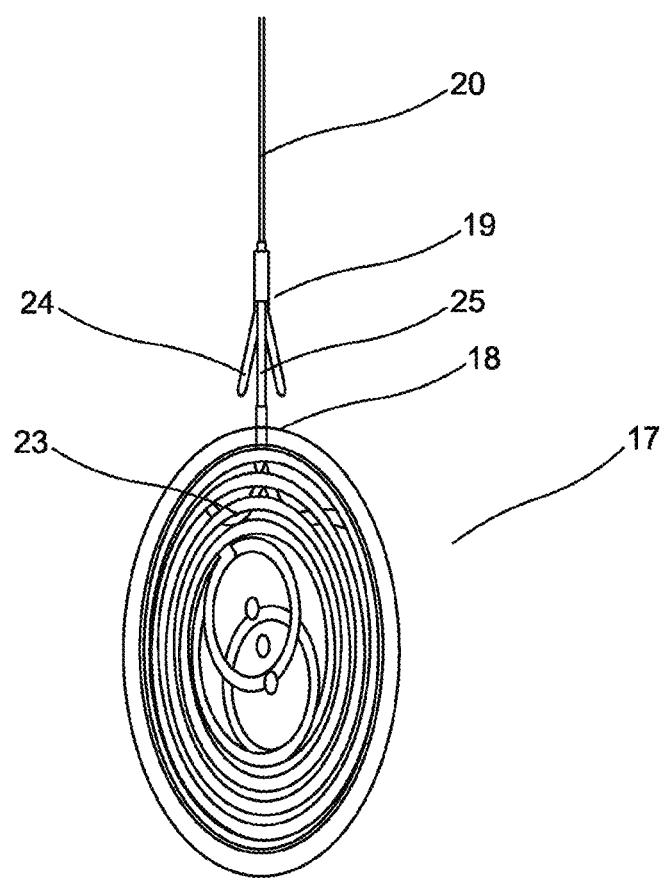

FIGS. 4A-C depict isometric, side, and front views of the deployed state of an embolic protection device including two off-axis reducing coils, a stem, a stopper, an anchor, and a pull wire according to some embodiments.

Figure 5:
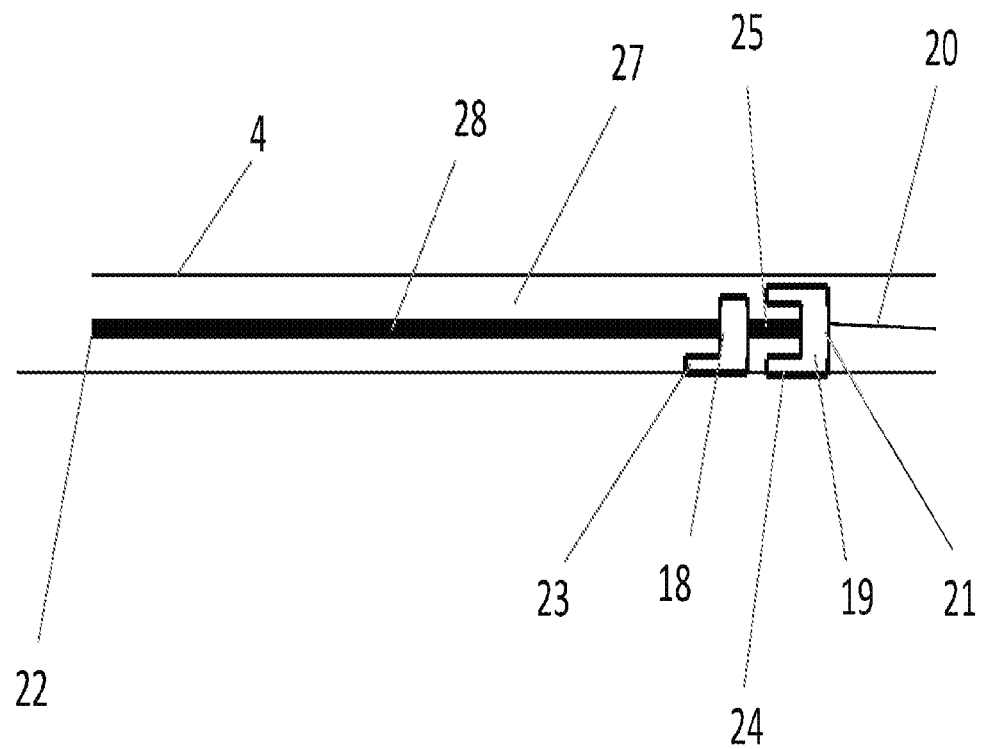
Figure 6A:
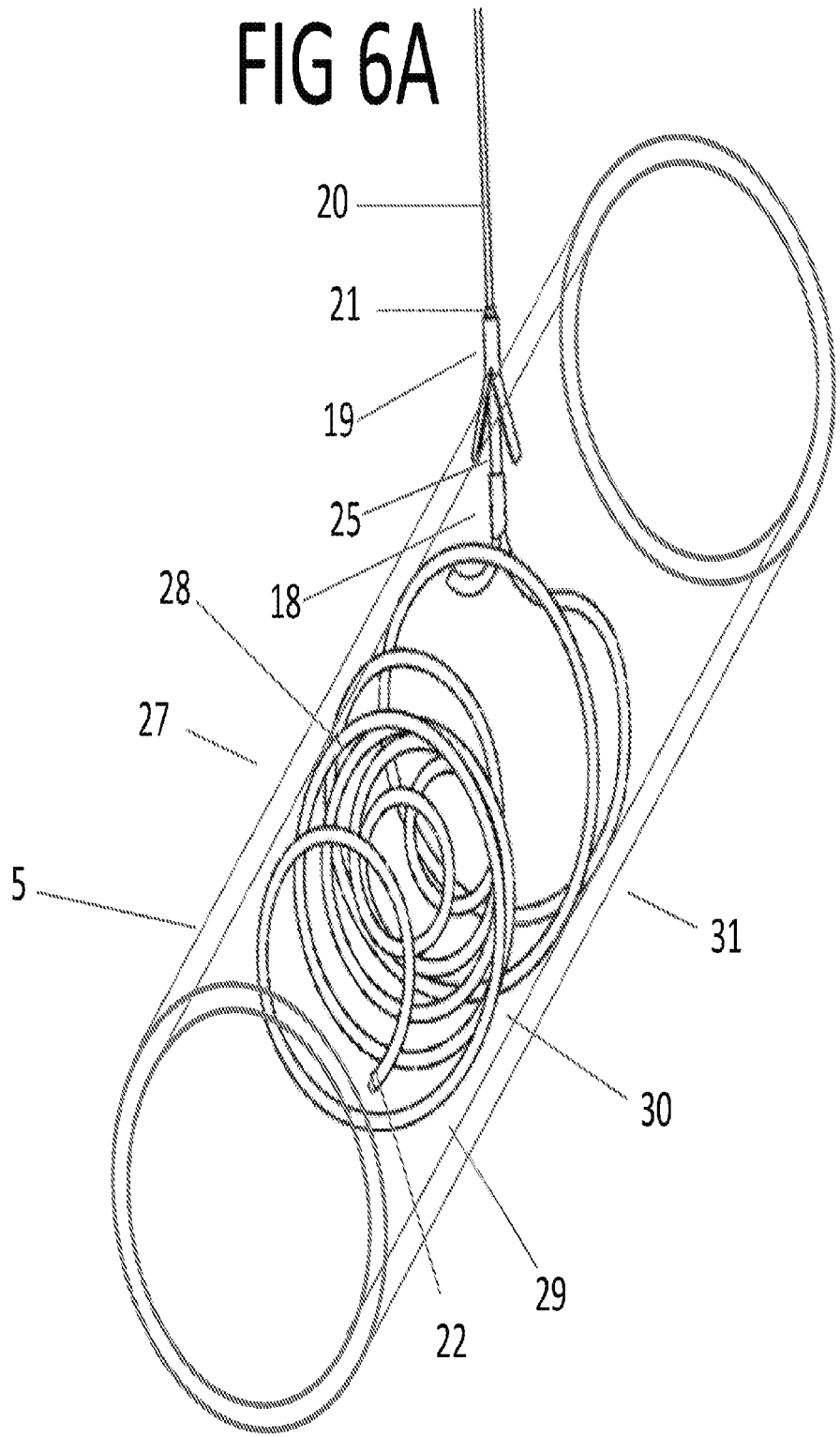
Figure 6B:
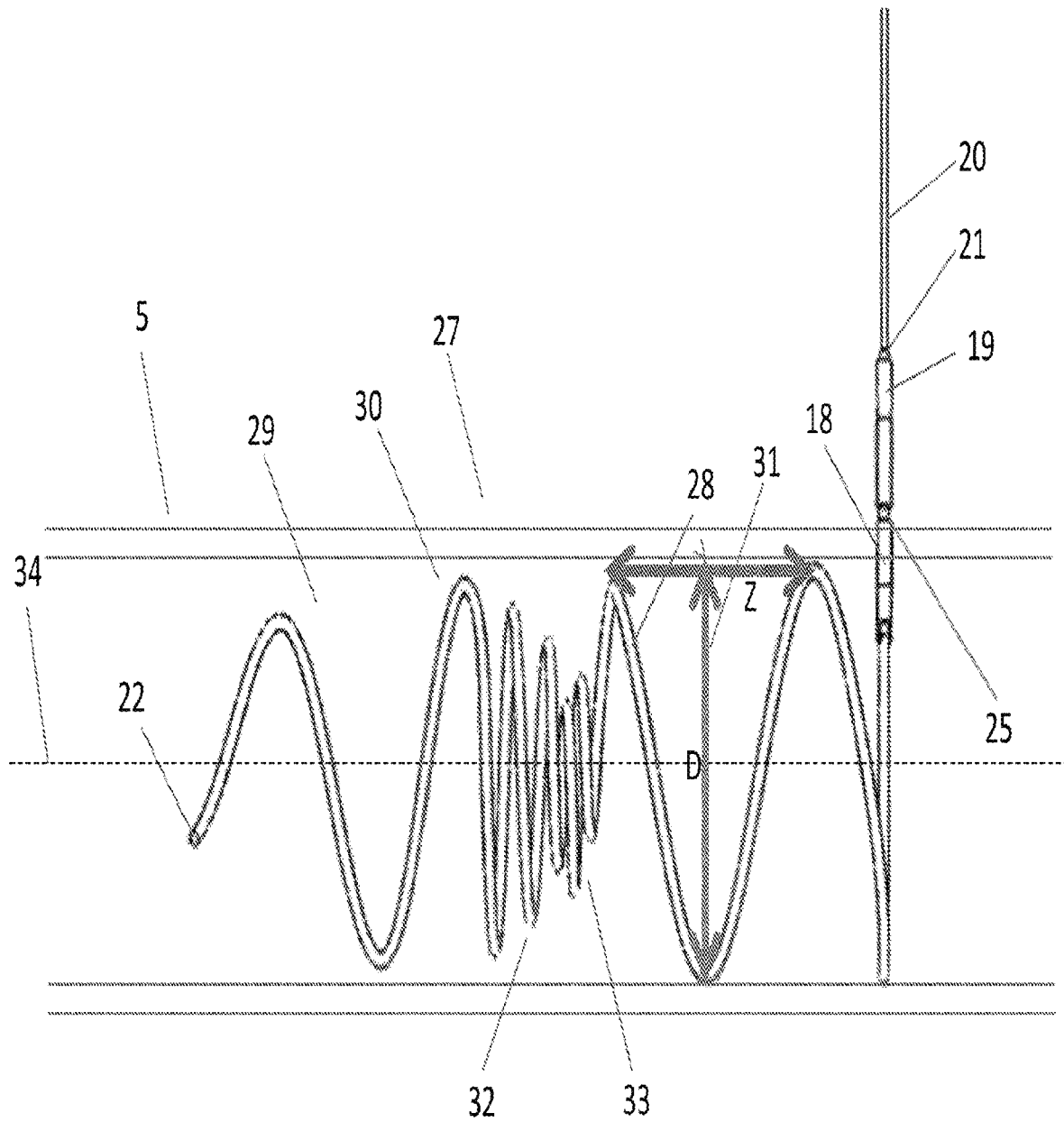
Figure 6C:
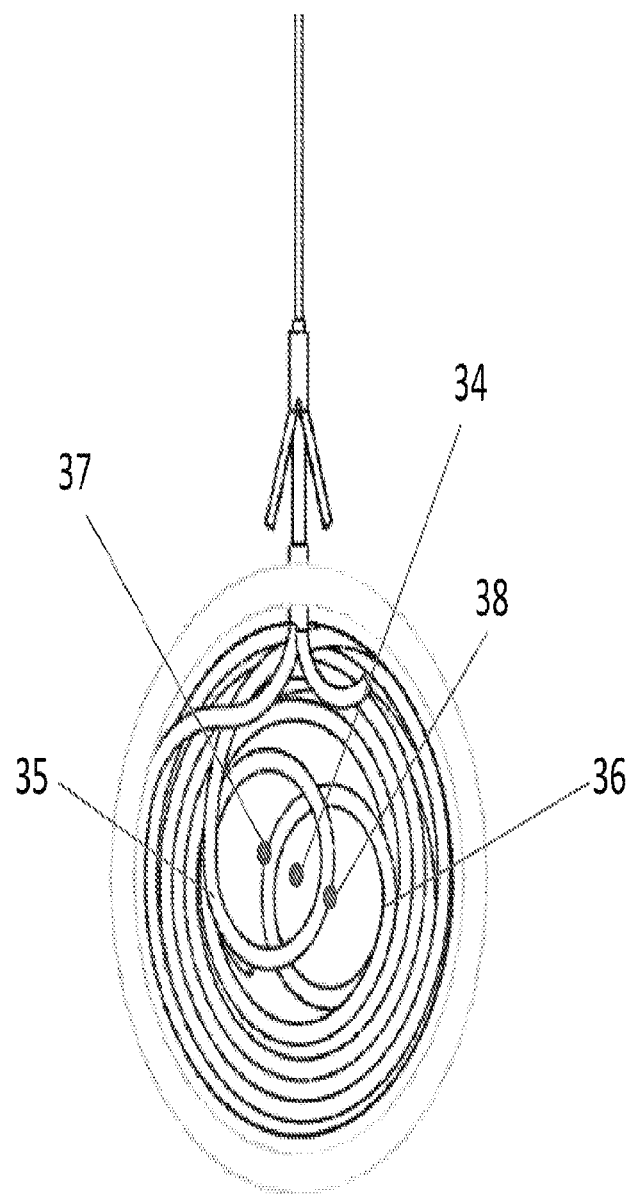
Figure 6D:
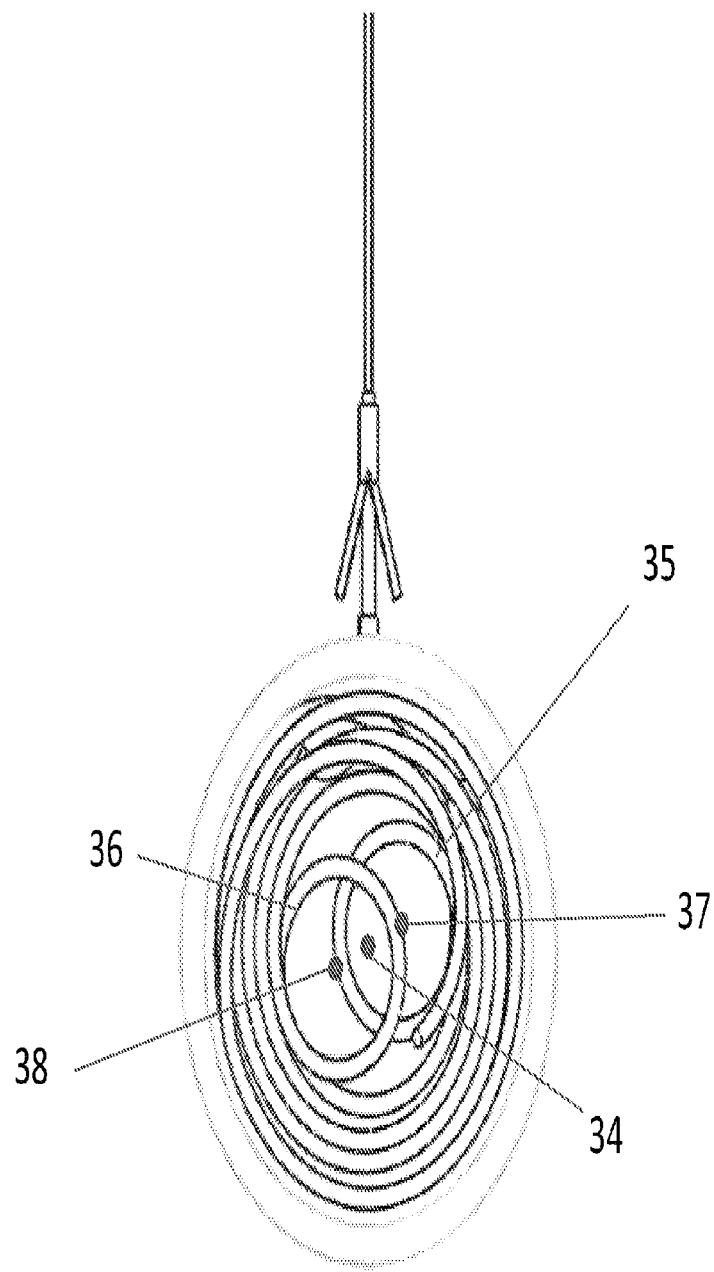

FIG. 5 depicts an un-deployed state of an embolic protection device including a filter portion interposed between two sets of support portions according to some embodiments.

FIGS. 6A-D depict isometric, side, back, and front views of the deployed state of an embolic protection device including a filter portion interposed between two sets of support portions according to some embodiments.

Figure 7A:
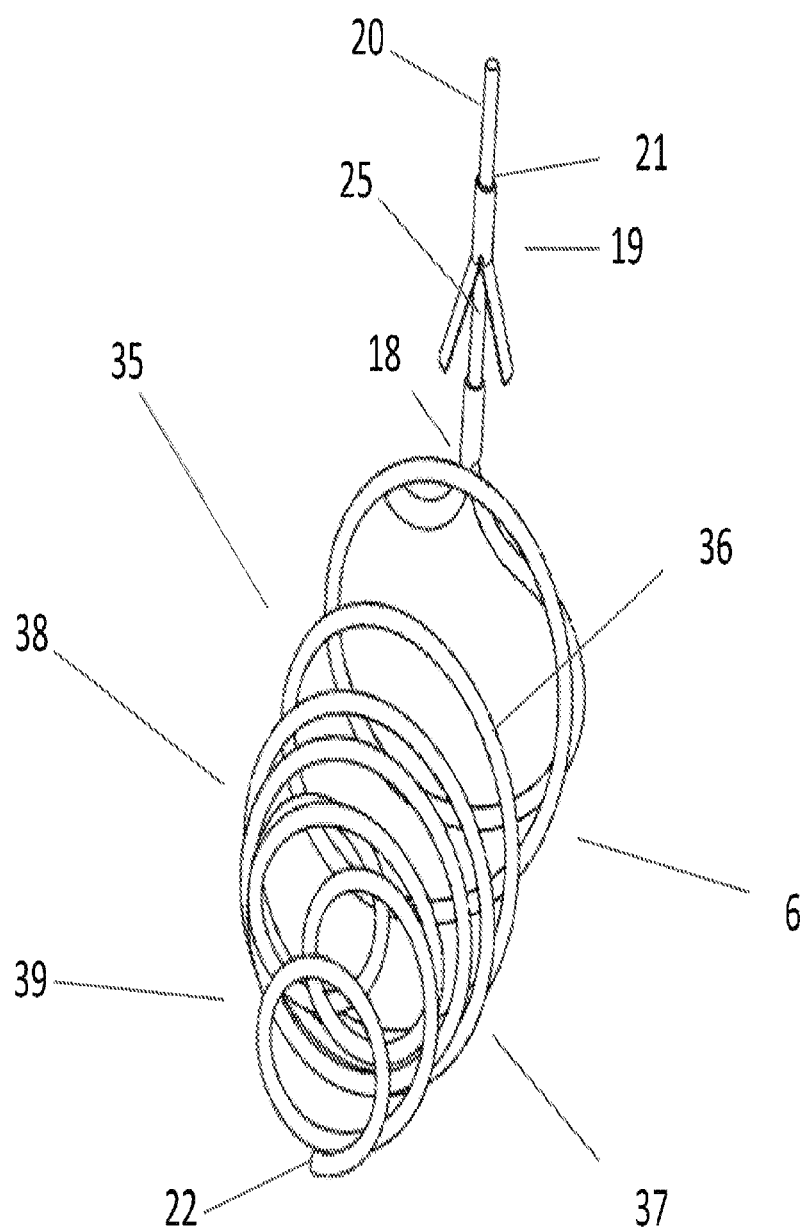
Figure 7B:
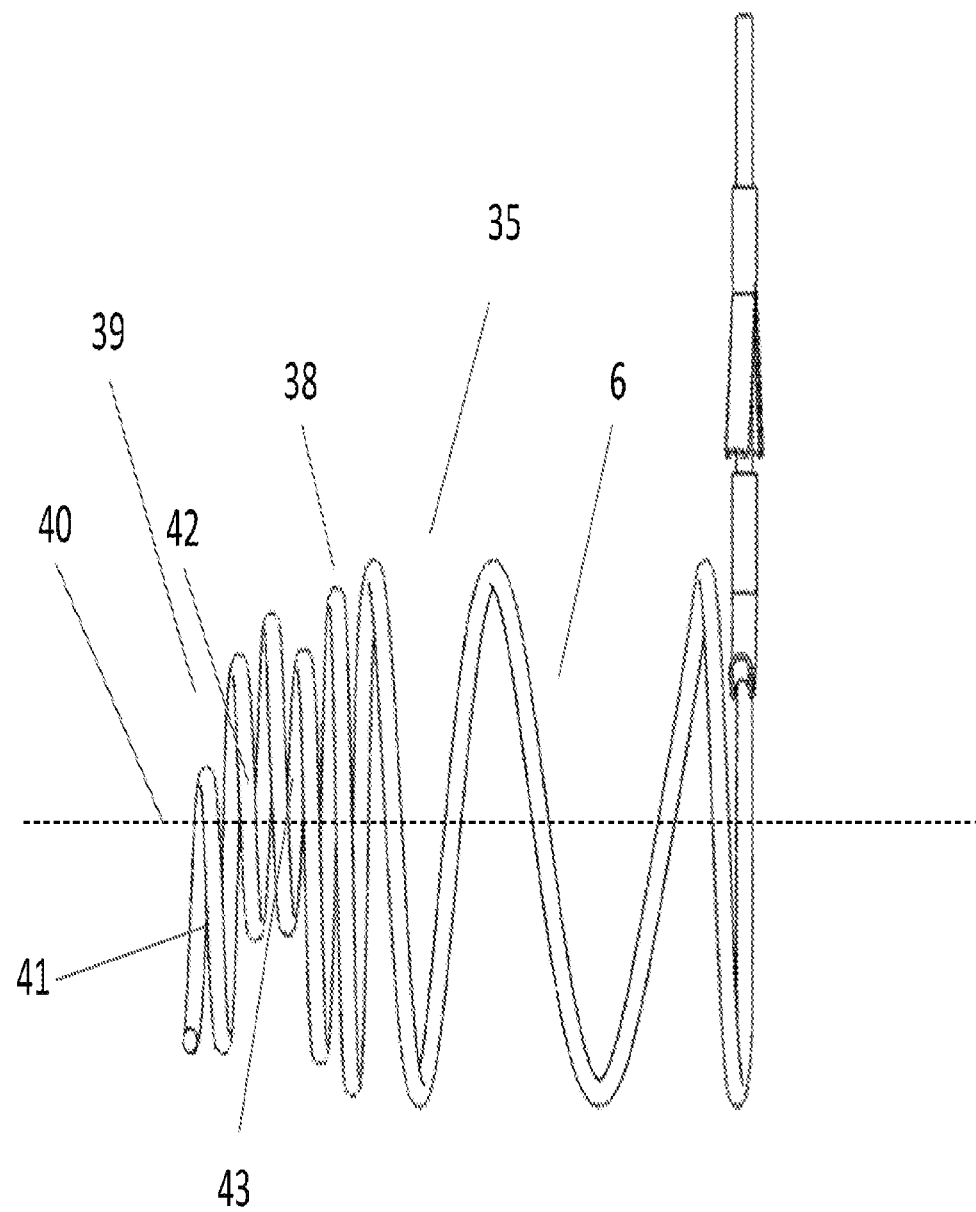
Figure 7C:
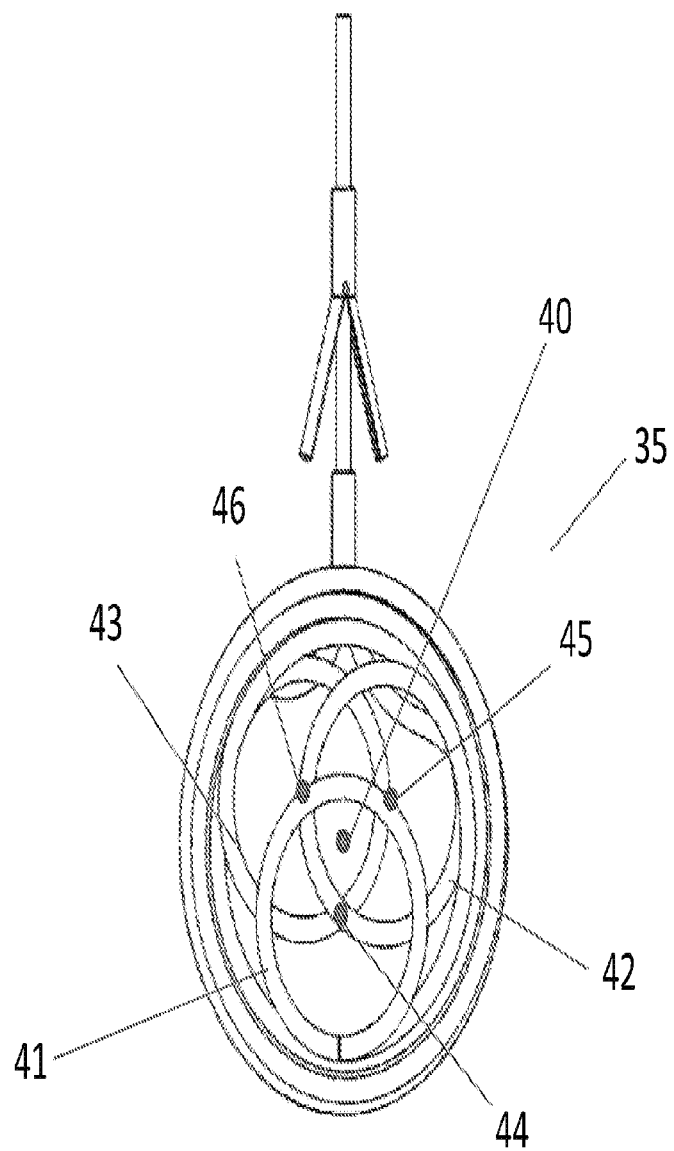

FIGS. 7A-C depict isometric, side, and front views of the deployed state of an embolic protection device including three off-axis reducing coils according to some embodiments.

Figure 8:
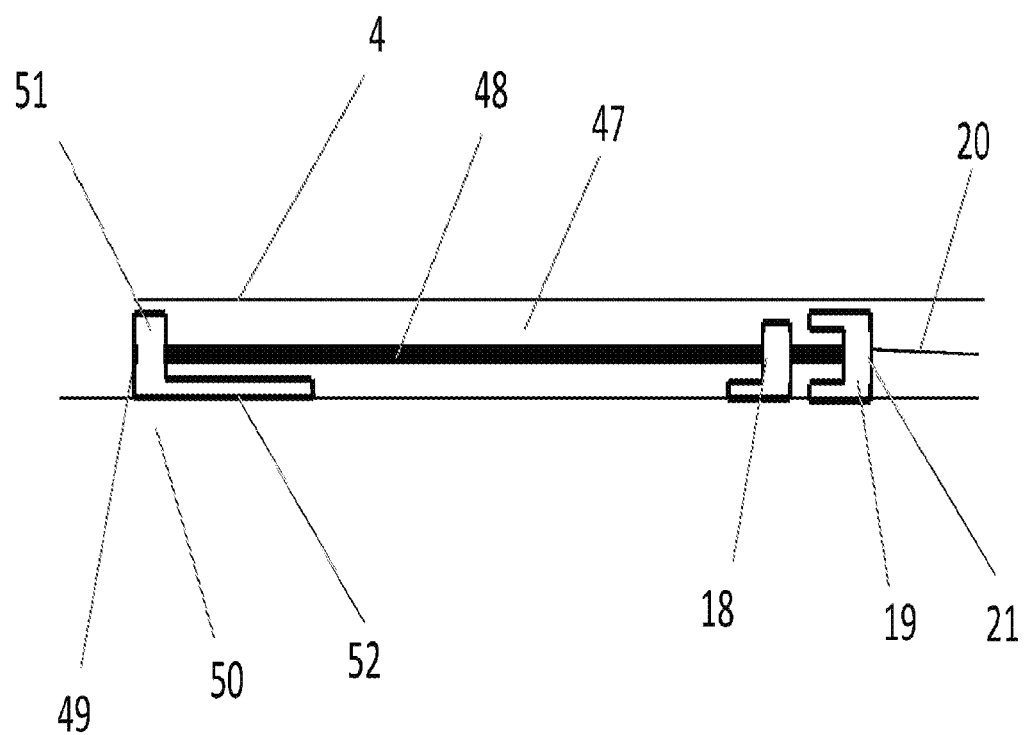

FIG. 8 depicts an un-deployed state of an embolic protection device including a reducing element according to some embodiments.

Figure 9A:
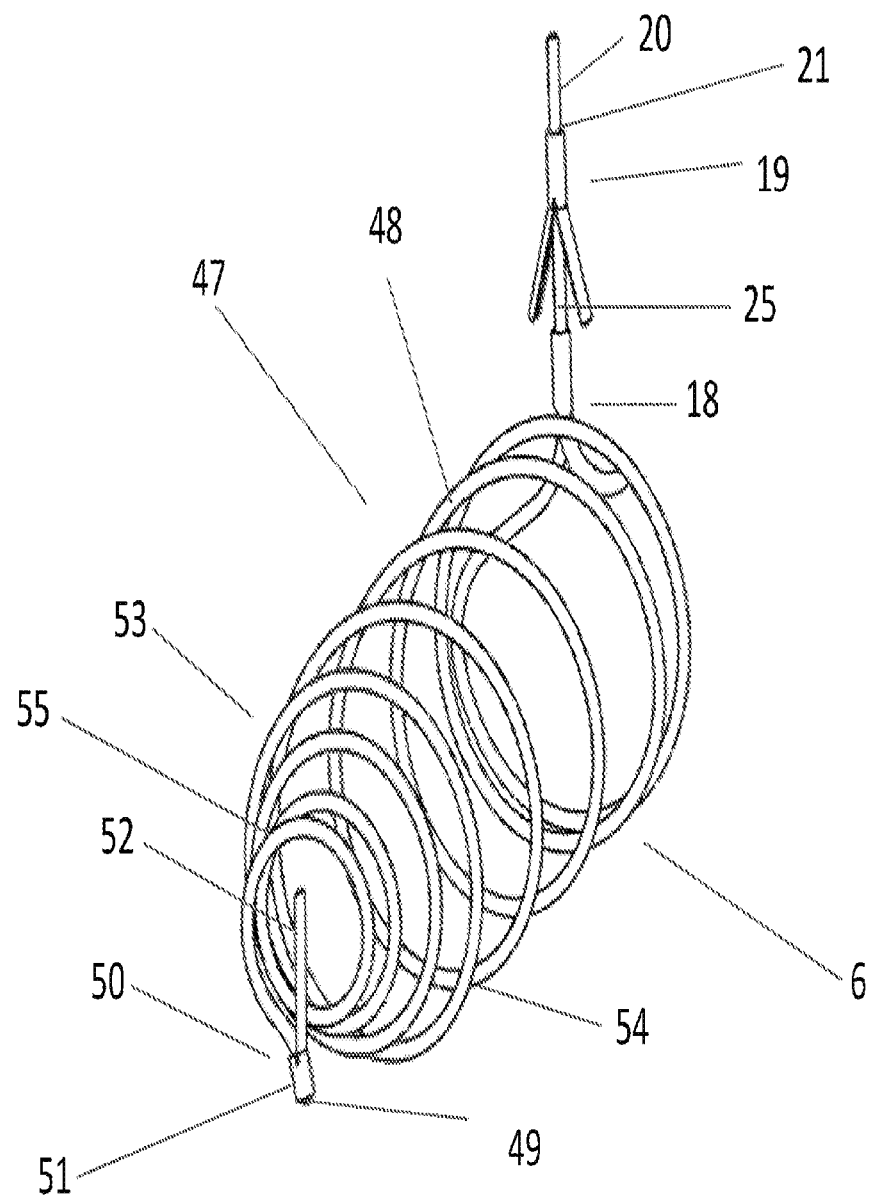
Figure 9B:
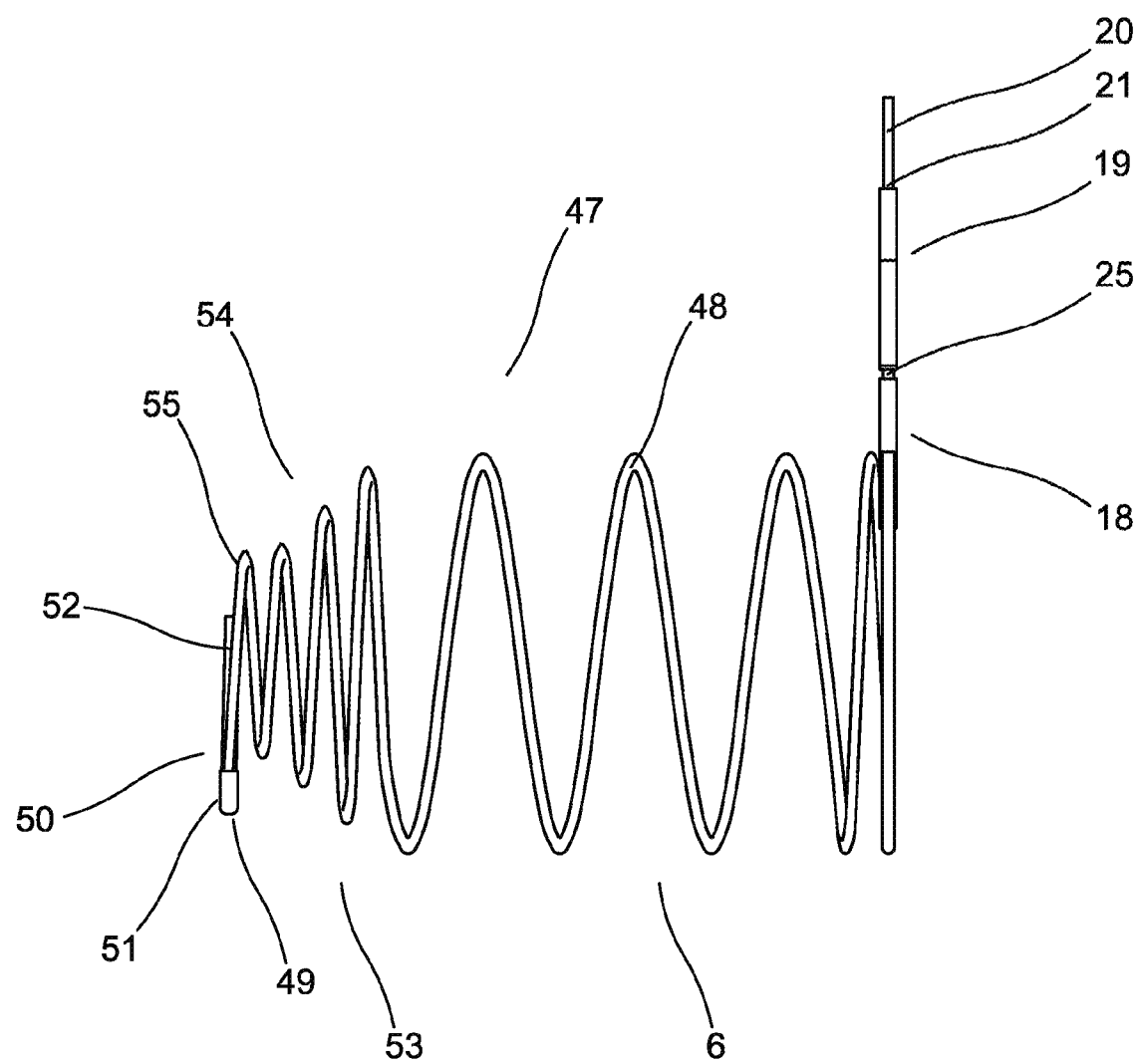
Figure 9C:
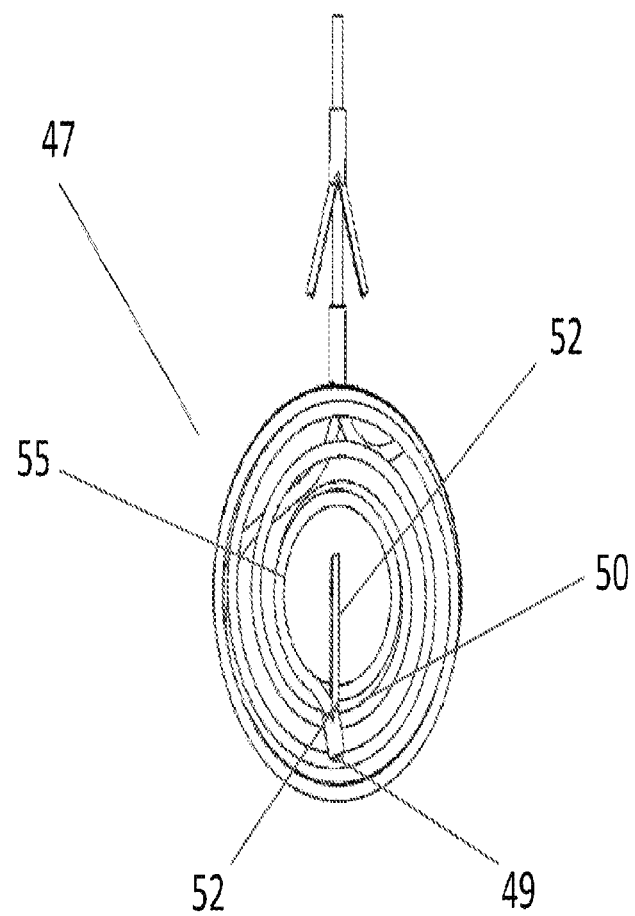

FIGS. 9A-C depict isometric, side, and front views of the deployed state of an embolic protection device including a reducing element according to some embodiments.

FIG. 10 depicts an un-deployed state of an embolic protection device including a ring-like reducing element according to some embodiments.

Figure 11A:
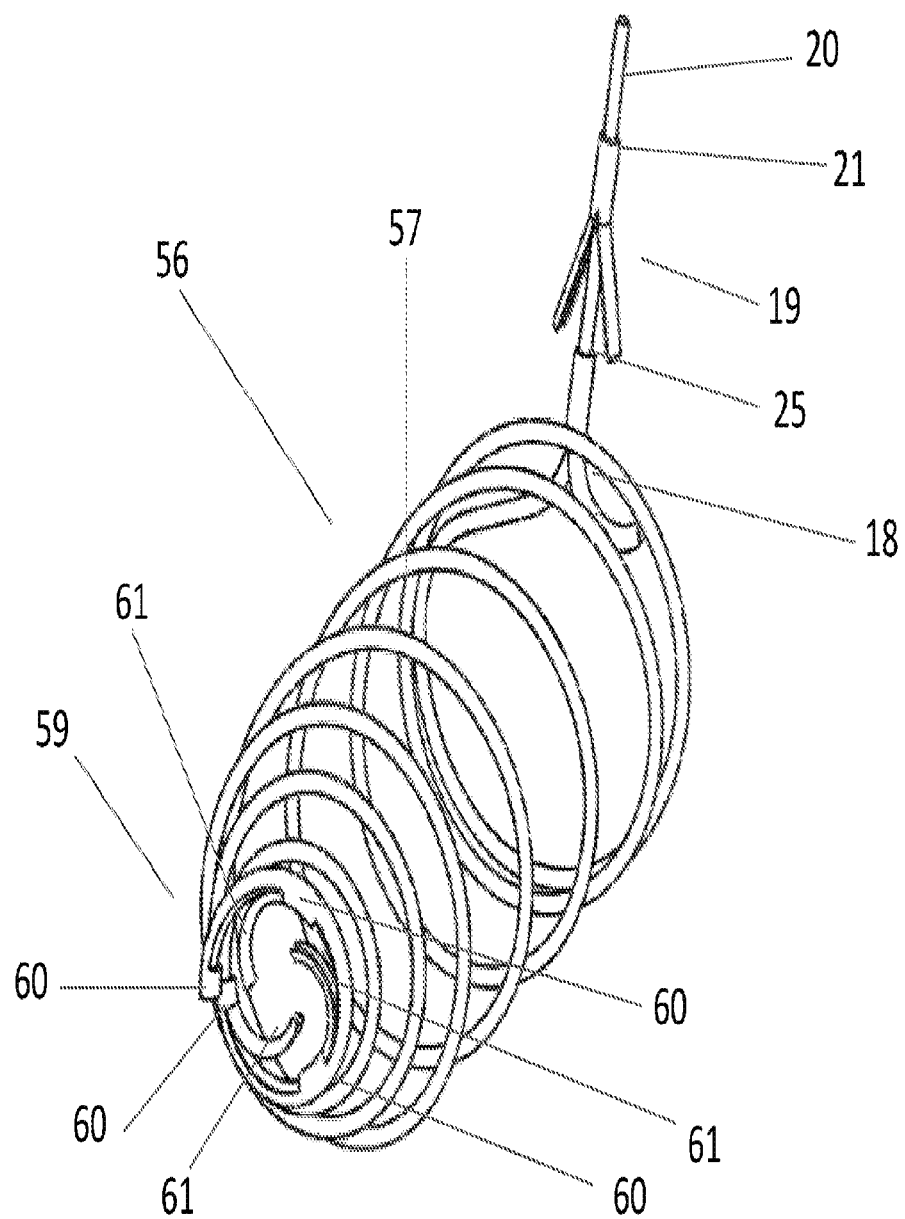
Figure 11B:
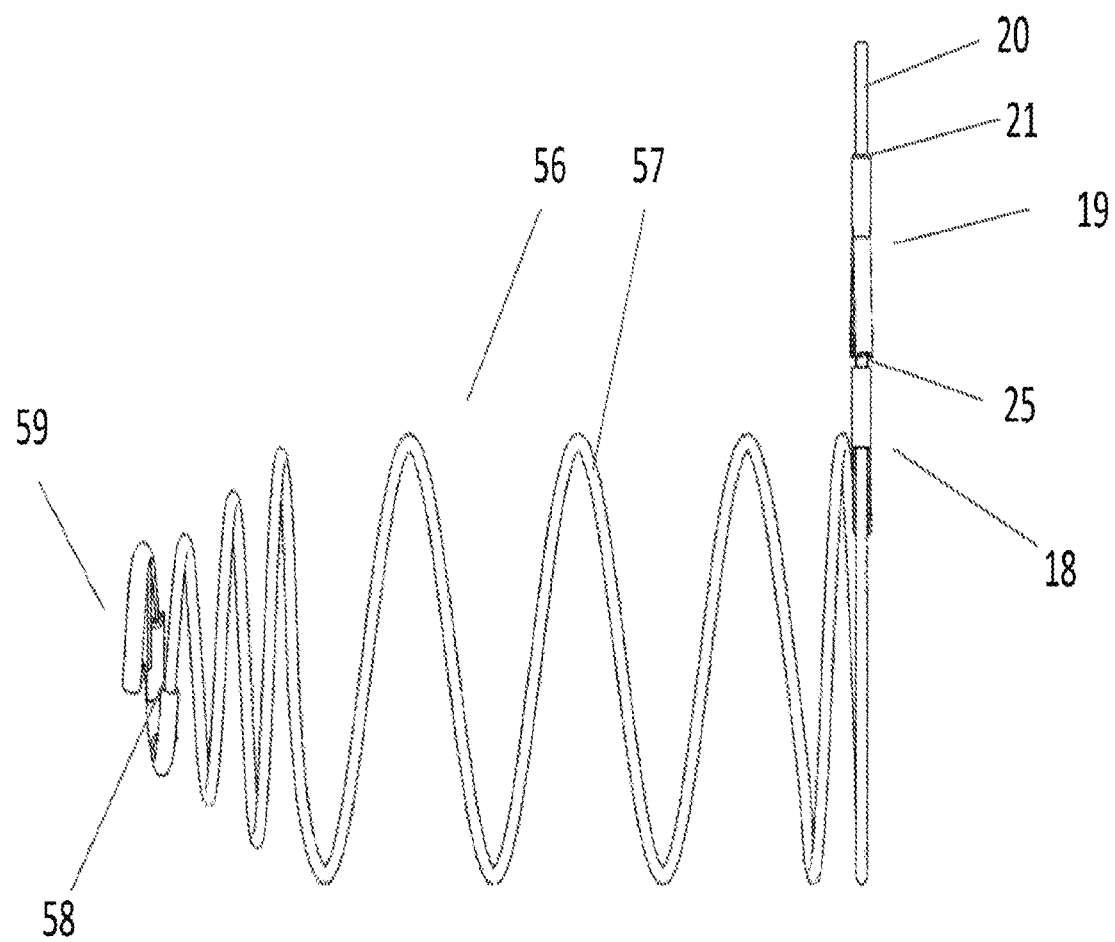
Figure 11C:
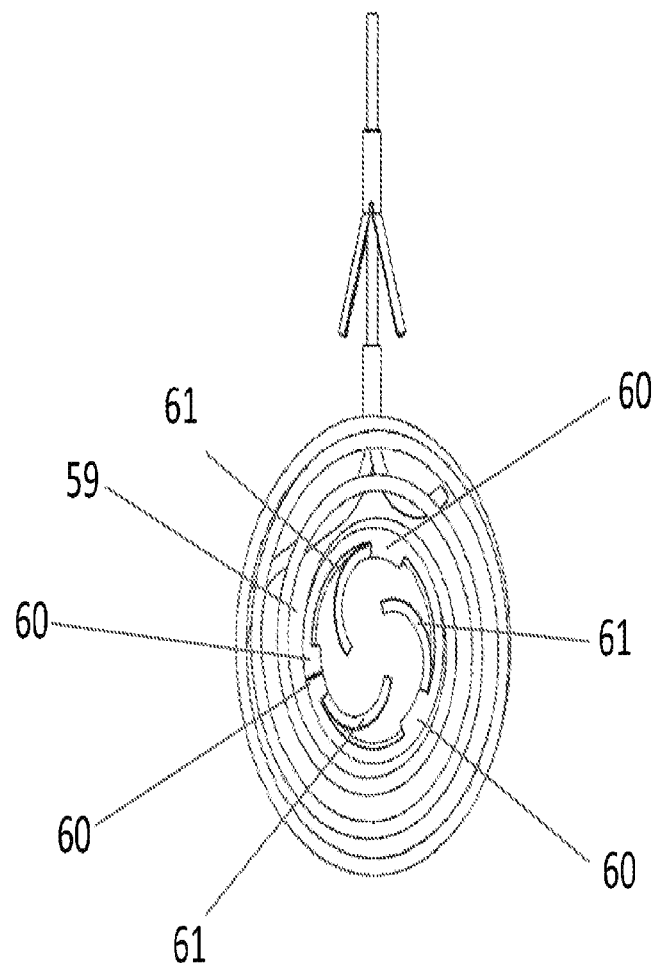

FIGS. 11A-C depict isometric, side, and front views of the deployed state of an embolic protection device including a ring-like reducing element according to some embodiments.

Figure 12:
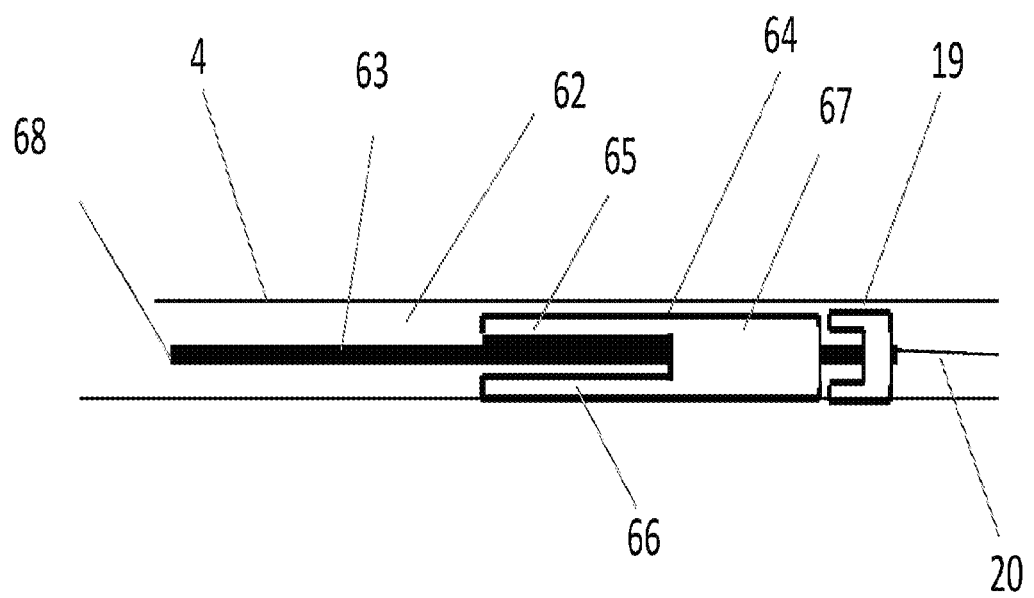

FIG. 12 depicts an un-deployed state of an embolic protection device including a stem and a reducing element collinear with the stem according to some embodiments.

Figure 13A:
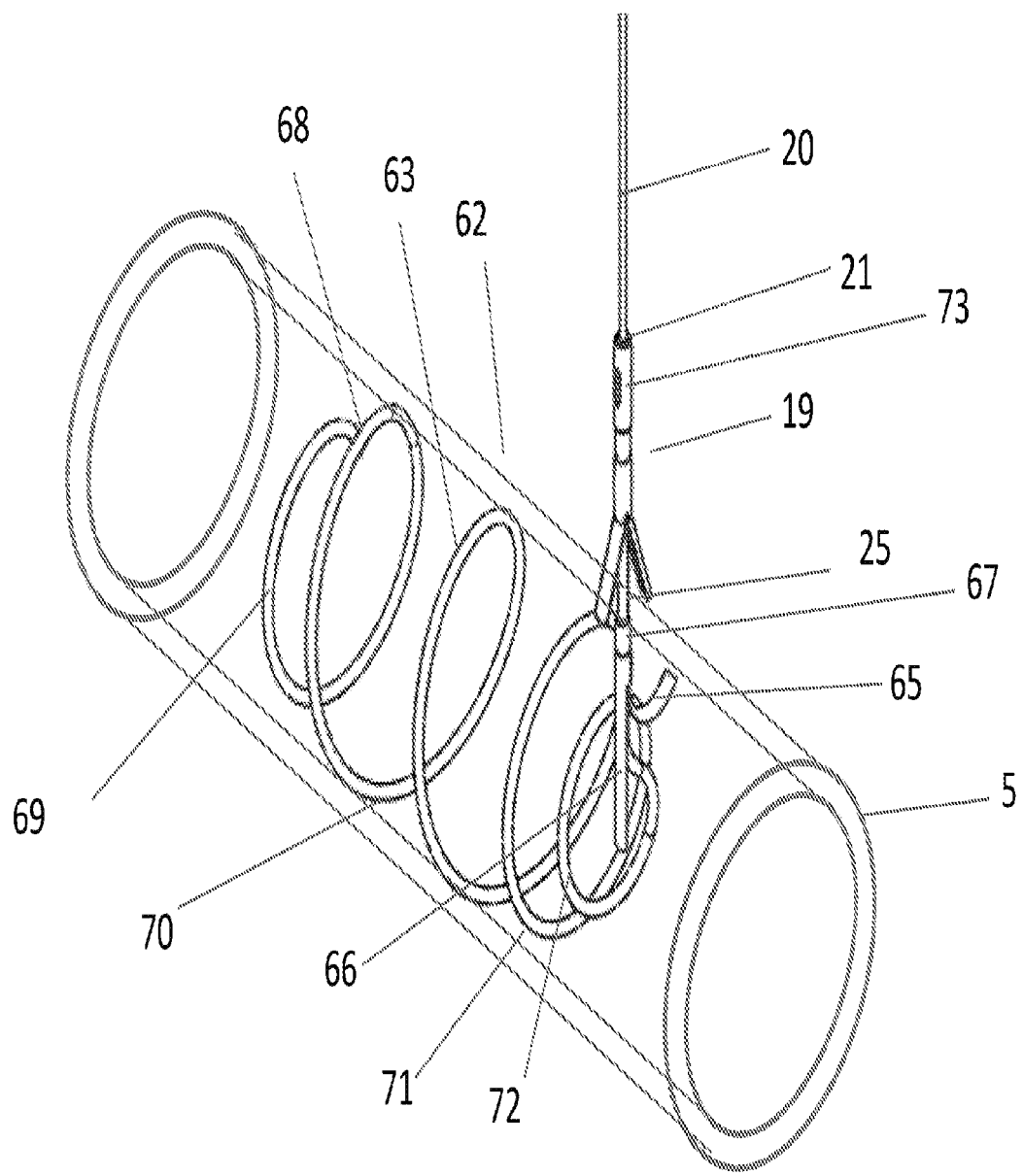
Figure 13B:
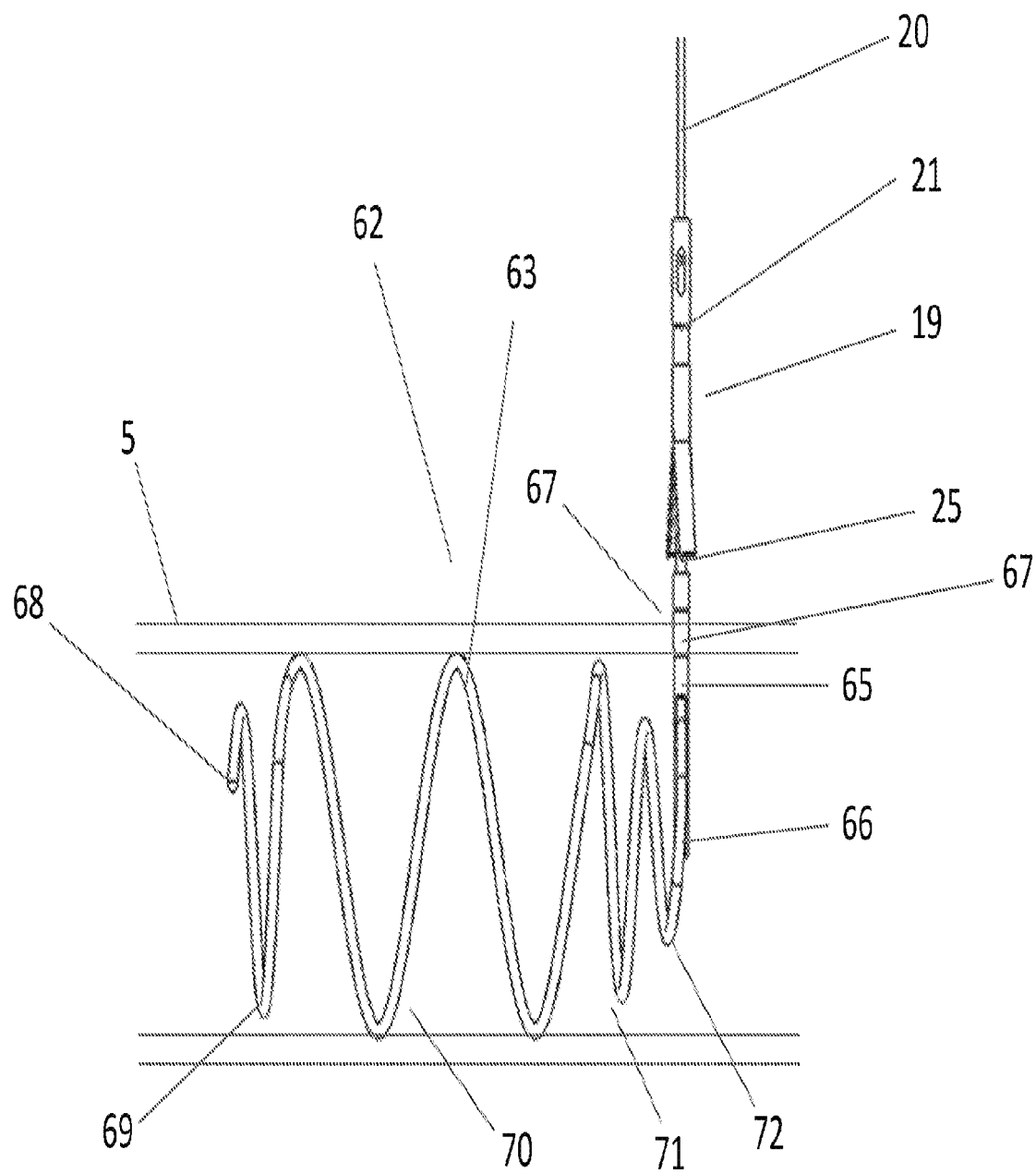
Figure 13C:
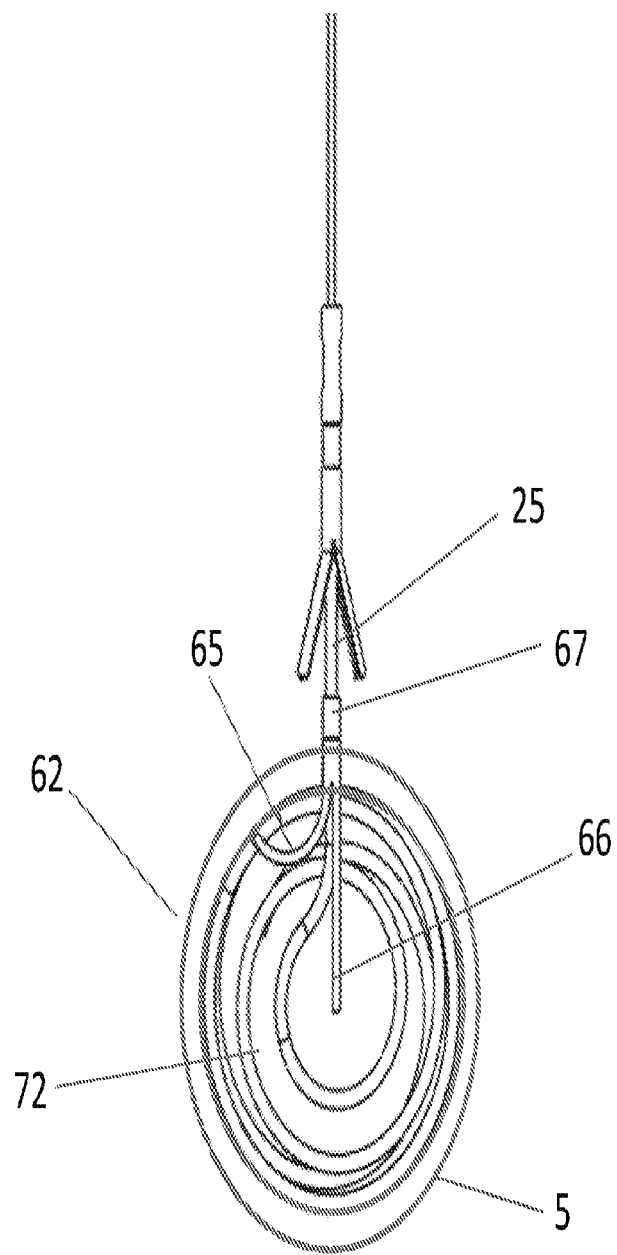

FIGS. 13A-C depict isometric, side, and front views of the deployed state of an embolic protection device including a stem and a reducing element collinear with the stem according to some embodiments.

FIGS. 14A-E depict a system and method for delivering/implanting an embolic protection device within a vessel of a patient according to some embodiments.

FIGS. 15A-H depict a system and method for delivering/implanting an embolic protection within a vessel of a patient according to some embodiments, the system may include an embolic protection device equipped with a pull wire according to some embodiments.

FIGS. 16A-H depict a system and method for providing embolic protection in a vessel of a patient, the system may include an embolic protection device which may be equipped with a pull wire, a stopper and an anchor according to some embodiments.

FIGS. 17A-H depict a system and method for implanting/delivering an embolic protection device within a vessel of a patient, the system may also include an embolic protection device which may be equipped with a pull wire, a stopper and an anchor.

FIGS. 18A-E depict a transcatheter system and method for implanting/delivering an embolic protection device within a vessel of a patient.

DETAILED DESCRIPTION OF SOME EMBODIMENTS

An embolic protection device/EPD 1 according to some embodiments of the present disclosure is depicted in FIGS. 1 and 2A-C.

Figure 1A:
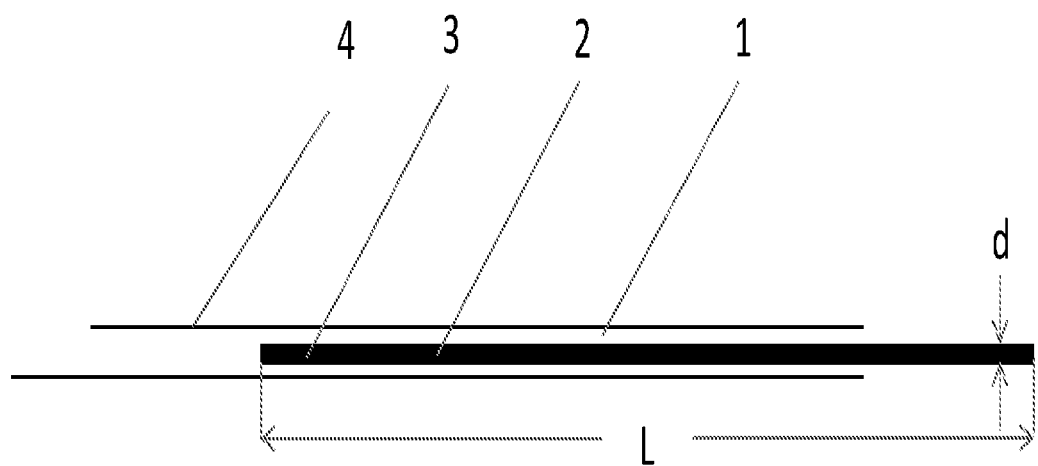
FIG. 1A depicts an un-deployed state of an embolic protection device including (e.g.) two off-axis reducing coils according to some embodiments.
Figure 1B:
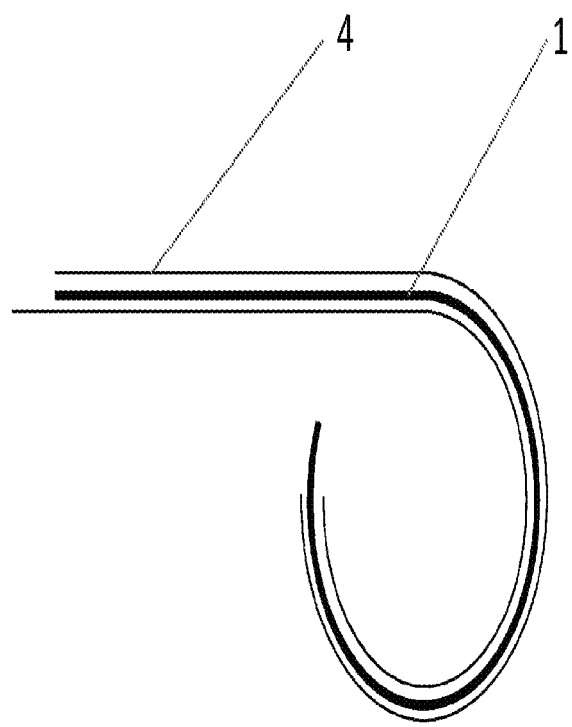
FIG. 1B depicts an un-deployed state of an embolic protection device including two off-axis reducing coils according to some embodiments.

Reference is made to FIG. 1A, which depicts an embodiment of device 1 in its un-deployed state. Device 1 may be constructed from a monofilament 2. In some embodiments, monofilament 2 may be made from a shape memory alloy such as nitinol. In some embodiments, monofilament 2 may be made from a shape memory polymer. In some embodiments, monofilament 2 may be made from a biodegradable or a bioresorbable polymer, such as polylactic acid or polyglycolitic acid. In some embodiments the length L of monofilament 2 may be between 5 cm and 25 cm. In some embodiments, monofilament 2 may have a round cross section. The diameter d of the round cross section may be between 0.05 mm and 0.3 mm. In some embodiments, the diameter may be between 1.2 and 2.8 mm. In some embodiments the cross section of monofilament 2 may not be round. For example, the shape of the cross section may be square or rectangular.

In some embodiments, the un-deployed shape of device 1 may include a portion 3 that is linear or substantially linear. Portion 3 may be configured to fit within the lumen of a cannula or a needle 4. In some embodiments, the entire device 1 may have a linear or substantially linear un-deployed shape (and in other embodiments, non-linear). In some embodiments, needle 4 may have an outer diameter in the range of 0.3 mm and 1.0 mm Reference is made to FIG. 1B, which depicts another embodiment of device 1 in its un-deployed state. In some embodiments, the un-deployed shape of device 1 may be non-linear. In some embodiments, the un-deployed shape of device 1 may include a curve. In some embodiments, device 1 or a portion thereof may be configured in its un-deployed shape to partially or totally reside within the lumen of a needle 4 whose shape may include a curve. In some embodiments, device 1 in its un-deployed state may be would or coiled entirely outside the lumen of a needle.

Reference is made to FIGS. 2A-C, which depict an embodiment of device 1 deployed in a body vessel 5. Body vessel 5 may be an artery, such as a carotid artery, or a vein, such as a superficial femoral vein or a vena cava.

In some embodiments, the deployed shape of filament 2 may be that of a wound wire comprising turns of varying sizes. In some embodiments, all turns may be wound in the same direction, for example, the clockwise direction or the counter clockwise direction. In some embodiments, the deployed shape of filament 2 may include a support portion 6 and a filter portion 7. In some embodiments, filter portion 7 may include a funnel portion 8 and a reducing member 9.

In some embodiments, support portion 6 may be shaped as a helix having a diameter D. In some embodiments, the diameter of support portion 6 may be greater than the diameter of vessel 5. In some embodiments, the diameter of support portion 6 may be equal to the diameter of vessel 5. Yet in other embodiments, the diameter of support portion 6 may be less than the diameter of vessel 5. In some embodiments support portion 6 may include coils of varying diameters. In some embodiments, the height or pitch Z (that is, the vertical distance between consecutive coils) may be constant. In other embodiments the pitch may vary. In some embodiments, the pitch near the proximal end 10 of filament 2 may be less than the pitch near the distal end 11. In some embodiments, the pitch near the distal end may be greater than the pitch near the proximal end.

In some embodiments, the coils of support portion 6 may be configured to contact the internal wall of vessel 5. In some embodiments, the coils may be configured to apply radial force to the internal walls of vessel 5, thereby promoting coverage of support portion 6 by cells growing from the vessel wall.

In some embodiments, support portion 6 may include at least one coil whose height Z may be less than the coil diameter D. In some embodiments, the height Z may be equal to the diameter D. In some embodiments, the height Z may be greater than the diameter D. In some embodiments, the height Z may be greater than 1.5 times the diameter D. In some embodiments, the height Z may be greater than 2 times the diameter D.

In some embodiments, funnel portion 8 of filter 7 may have turns that vary in diameter. In some embodiments, coil diameter may taper or decrease in diameter towards the distal end. In some embodiments, the minimal distance between consecutive coils of the funnel portion may be in the range of 0.3 and 1.5 mm. In some embodiments, the minimal distance between consecutive coils of the funnel portion may be less than about 1.5 mm, thereby preventing emboli that may cause major stroke from passing between the coils of the funnel portion.

In some embodiments, support portion 6 and funnel portion 7 may have a common helix axis 12. In some embodiments, reducing member 9 may include at least one off-axis coil whose center is not on axis 12. In some embodiments, reducing member 9 may include two off-axis coils 13 and 14 whose centers 15 and 16, respectively, are not on axis 12 and are distinct from each other. In some embodiments, a line segment connecting centers 15 and 16 may intersect axis 12, resulting in a reducing element shaped as a Venn diagram, as in FIG. 2C.

In some embodiments, inclusion of reducing member 9 in device 1 has the advantage of reducing the maximal embolus size that may pass through device 1. Note that without reducing member 9 the maximal embolus size would be much larger, roughly equal to the diameter of the smallest coil in funnel portion 7. Note also that there is a limit to how small the smallest coil of the funnel portion may be made, as the following example makes clear:

Example

Monofilament 2 is made from nitinol. The diameter d of monofilament 2 is 0.22 mm, which provides device 1 with sufficient stiffness to maintain its shape in the pulsating carotid environment, yet provides enough flexibility to allow loading into a needle. The maximal allowable strain in monofilament 2 is $\varepsilon=8\%$: otherwise, the shape memory of nitinol is lost and recovery of the desired deployed shape of device 1 is impossible. Given the specified parameters, the minimal allowable diameter of the smallest coil in funnel 7 is $d/\varepsilon=0.22/0.08=2.75$ mm. Thus, all emboli sized 2.75 mm or less will get through device 1, and major stroke may be caused by these emboli. On the contrary, the advent of reducing member 9 having two off-axis coils 13 and 14 arranged with their centers distinct from each other as in FIGS. 2A-C reduces the maximal embolus size that may get through to about 1.1 mm. This significantly improves the ability of device 1 to prevent major stroke while the diameter of monofilament 2 is maintained at 0.22 mm without plastic deformation in filament 2 upon transition between the un-deployed and deployed states.

An embolic protection device 17 according to some embodiments of the present disclosure is depicted in FIGS. 3 and 4A-C. Device 17 is similar to device 1, except that monofilament 2 is replaced with monofilament 26, and optionally each of a stopper 18, an anchor 19, and a pull wire 20 may be added. In some embodiments, stopper 18 may be attached to monofilament 26 near its proximal end 21. In some embodiments, anchor 19 may be attached to monofilament 26 near its proximal end 21 and proximally to stopper 18. In some embodiments, pull wire 20 may be attached to filament 26 at its proximal end 21 and proximally to stopper 18 and/or anchor 19. Attachment of each of stopper 18, anchor 19, and pull wire 20 may be made using any attachment method known in the art, such as welding, crimping, or gluing. Attachment of pull wire 20 may be made using a connector receiving the pull wire at its proximal end and monofilament 26 at its distal end. In some embodiments device 17 may include only monofilament 2. In some embodiments device 17 may include monofilament 2, pull wire 20, and optionally a connector connecting the monofilament and the pull wire.

In some embodiments, stopper 18 may be made from a shape memory material, such as nitinol or a shape memory polymer. In some embodiments stopper 18 may have an un-deployed shape configured to fit around or alongside monofilament 26 in the lumen of needle 4.

In some embodiments, anchor 19 may be made from a shape memory material, such as nitinol or a shape memory polymer. In some embodiments anchor 19 may have an un-deployed shape configured to fit around or alongside monofilament 26 in the lumen of needle 4.

Reference is made to FIG. 3, which depicts the un-deployed state of device 17 according to some embodiments. In some embodiments, at least a portion of monofilament 26 is configured to fit in the lumen of a needle 4. In some embodiments, device 17 in its entirety is configured to fit within the lumen of a needle.

Reference is made to FIGS. 4A-C, which depict embolic protection device 17 deployed in a body vessel. In some embodiments, the deployed shape of monofilament 26 is similar to that of monofilament 2, with the addition of stem 25. In some embodiments, stopper 18, anchor 19, and pull wire 20 may each be attached to stem 25. Support portion 6 and filter portion 7 have already been described in detail above, and therefore their detailed description is omitted.

In some embodiments, support portion 6 may include at least one coil whose height or pitch Z may be less than the coil diameter D. In some embodiments, the height Z may be equal to the diameter D. In some embodiments, the height Z may be greater than the diameter D. In some embodiments, the height Z may be greater than 1.5 times the diameter D. In some embodiments, the height Z may be greater than 2 times the diameter D. Having at least one elongated coil with Z/D>1.5 may have the advantage of resisting the axial compression of support portion 6 by vessel contraction. Axial compression may happen as filter portion 7 is pushed in the direction of stem 25 (which is fixed in the vessel wall) by vessel contraction or pulsation. Resisting support portion compression is important because it helps prevent phenomena such as distortion of the deployed shape of device 17 or even inversion of the direction of funnel portion 7 by the pivoting of the compressed device around the stem and subsequent device extension. Large Z/D ratio (elongated coil) resists support portion compression because initial compression of an elongated coil causes the coil diameter to increase significantly, which subsequently causes the coil to encounter resistance from the vessel walls, thereby making further coil compression (and resulting coil diameter growth) more difficult.

In some embodiments, stem 25 may be configured to traverse the wall of vessel 5. In some embodiments, stem 25 may be configured to breach, but not traverse, the wall of vessel 5. In some embodiments, stem 25 may be configured approximately perpendicular to the vessel wall.

In some embodiments, stopper 18 may be configured to reside in the vessel lumen. In some embodiments, at least a portion of stopper 18 may be configured to reside in the vessel wall. In some embodiments, stopper 18 may have a deployed shape having one or more protrusions 23. One or more protrusions 23 may be configured to resist the movement of monofilament 26 across the wall of vessel 5, from inside the lumen of vessel 5 towards the outside of the vessel.

In some embodiments, anchor 19 may be configured to reside outside vessel 5. In some embodiments, at least a portion of anchor 19 may be configured to reside in the vessel wall. In some embodiments, at least a portion of anchor 19 may be configured to reside outside vessel 5. In some embodiments, anchor 19 may have a deployed shape having one or more protrusions 24. One or more protrusions 24 may be configured to resist the movement of monofilament 2 across the wall of vessel 5, from the outside of vessel towards the lumen of the vessel. In some embodiments, both stopper 18 and anchor 19 are configured to prevent the migration of device 17.

In some embodiments, pull wire 20 may extend outside the skin of the patient. In some embodiments the pull wire may be used to pull device 17 out from the vessel and from the patient's body. In some embodiments, pull wire 20 may be made from metal or alloy, such as nitinol, or polymer such as nylon. In some embodiments, pull wire 20 may be made from a biodegradable or a bioresorbable polymer, such as polylactic acid or polyglycolitic acid. In some embodiments pull wire 20 may have a round cross section. In some embodiments the diameter of the pull wire cross section may be in the range of 0.025 mm to 0.25 mm.

An embolic protection device 27 according to some embodiments of the present disclosure is depicted in FIGS. 5 and 6A-D. In some embodiments, device 27 may be similar to device 17, except that monofilament 26 is replaced with monofilament 28 having proximal and distal ends 21 and 22. Note that each of stopper 18, anchor 19, and pull wire 20 is optional. Stem 25 is also optional.

Reference is made to FIG. 5, which depicts the un-deployed state of device 27 according to some embodiments. In some embodiments, the un-deployed state of device 27 is substantially similar to the un-deployed state of device 17, and therefore its detailed description is omitted.

Reference is made to FIGS. 6A-D, which depict the deployed state of device 27. The deployed state of device 27 is similar to the deployed state of device 17, except that monofilament 26 is replaced with monofilament 28.

Monofilament 28 is similar to monofilament 26 in all aspects except its deployed shape. In some embodiments, the deployed shape of monofilament 28 may be that of a wound wire comprising turns of varying sizes. In some embodiments, all turns may be wound in the same direction, for example, the clockwise direction or the counter clockwise direction. In some embodiments, the deployed shape of monofilament 28 optionally may include a distal support portion 29. In some embodiments, the deployed shape of monofilament 28 may include a filter portion 30 and a proximal support portion 31. In some embodiments, the deployed shape of monofilament 28 includes stem 25. In some embodiments, filter portion 30 may include a funnel portion 32 and a reducing member 33.

In some embodiments, distal support portion 29 may be shaped as a helix having a diameter. In some embodiments, the distal-most coil of distal support portion 29 may have a diameter less than the diameter of vessel 5. In some embodiments, the diameter of some coils distal support portion 29 may be greater than the diameter of vessel 5. In some embodiments, the diameter of some coils of distal support portion 29 may be equal to the diameter of vessel 5. Yet in other embodiments, the diameter of some coils of distal support portion 29 may be less than the diameter of vessel 5. In some embodiments distal support portion 29 may include coils of varying diameters. In some embodiments, the pitch may be constant. In other embodiments the pitch may vary.

In some embodiments, the coils of distal support portion 29 may be configured to contact the internal wall of vessel 5. In some embodiments, the coils may be configured to apply radial force to the internal walls of vessel 5, thereby promoting coverage of distal support portion 29 by cells growing from the vessel wall.

In some embodiments, proximal support portion 31 may be shaped as a helix having a diameter. In some embodiments, the diameter of some coils of proximal support portion 31 may be greater than the diameter of vessel 5. In some embodiments, the diameter of some coils of support portion 31 may be equal to the diameter of vessel 5. Yet in other embodiments, the diameter of some coils of proximal support portion 31 may be less than the diameter of vessel 5. In some embodiments proximal support portion 31 may include coils of varying diameter. In some embodiments, the pitch may be constant. In other embodiments the pitch may vary.

In some embodiments, each of support portions 29 and 31 may include at least one coil whose height or pitch Z may be less than the coil diameter D. In some embodiments, the height Z may be equal to the diameter D. In some embodiments, the height Z may be greater than the diameter D. In some embodiments, the height Z may be greater than 1.5 times the diameter D. In some embodiments, the height Z may be greater than 2 times the diameter D. Having at least one coil with Z/D>1.5 may have the advantage of resisting the axial compression of support portion 29 or 31 vessel compression or pulsation. The importance of this has already been discussed above.

In some embodiments, filter portion 30 may be distal to proximal support portion 31. In some embodiments, filter portion 30 may be interposed between distal support portion 29 and proximal support portion 31. In some embodiments, funnel portion 32 of filter portion 30 may have turns that vary in diameter. In some embodiments, coil diameter may increase towards the distal end 22 of filament 28. In some embodiments, coil diameter may decrease in diameter towards the distal end 22 of filament 28. In some embodiments, the minimal distance between consecutive coils of the funnel portion may be in the range of 0.3 and 1.5 mm. In some embodiments, the minimal distance between consecutive coils of the funnel portion may be less than about 1.5 mm, thereby preventing emboli that may cause major stroke from passing between coils of the funnel portion.

In some embodiments, proximal support portion 31 and funnel portion 32 may have a common helix axis 34. In some embodiments, reducing member 33 may include at least one off-axis coil whose center is not on axis 34. In some embodiments, reducing member 33 may include two off-axis coils 35 and 36 whose centers 37 and 38, respectively, are not on axis 34 and are distinct from each other. In some embodiments, a line segment connecting centers 37 and 38 may intersect axis 34, resulting in a reducing element shaped as a Venn diagram, as in FIG. 6D.

In some embodiments, device 27 may optionally have a stem 25. In some embodiments, stem 25 may optionally be configured with one or more of a stopper 18, an anchor 19, and a pull wire 20. In some embodiments, the stem, stopper, anchor and pull wire may be substantially the same as in device 17. Therefore their detailed description is omitted.

An embolic protection device 35 according to some embodiments of the present disclosure is depicted in 7A-C. In some embodiments, the un-deployed state of device 35 is substantially similar to the un-deployed state of device 17, and therefore its detailed description is omitted.

In some embodiments, the deployed state of device 35 is similar to the deployed state of device 17, except that monofilament 26 is replaced with monofilament 36.

In some embodiments, monofilament 36 may be similar to monofilament 28 in all respects except its deployed shape. In some embodiments, the deployed shape of monofilament 36 may be similar to the deployed shape of monofilament 26 in all respects except that filter portion 7 may be replaced with filter portion 37. Filter portion 37 may include a funnel portion 38 and a reducing member 39, which may be different from reducing member 9 of filament 26. In some embodiments, funnel portion 38 may be substantially similar to funnel portion 8 of monofilament 26.

In some embodiments, proximal support portion 6 and funnel portion 38 may have a common helix axis 40. In some embodiments, reducing member 39 may include three off-axis coils 41, 42 and 43 whose centers 44, 45 and 46, respectively, are not on axis 40 and are distinct from each other. In some embodiments, the three centers may define the shape of an equilateral triangle, resulting in a reducing element shaped as a Venn diagram, as in FIG. 7C.

In some embodiments, device 35 may optionally have a stem 25. In some embodiments, stem 25 may optionally be configured with one or more of a stopper 18, an anchor 19, and a pull wire 20. In some embodiments, the stem, stopper, anchor and pull wire are substantially the same as in device 17. Therefore their detailed description is omitted.

An embolic protection device 47 according to some embodiments of the present disclosure is depicted in FIGS. 8 and 9A-C.

Reference is made to FIG. 8, which depicts the un-deployed state of device 47 according to some embodiments. In some embodiments, device 47 may be substantially similar to device 17, except that monofilament 26 is replaced with monofilament 48 and reducing member 9 is replaced with reducing member 50. In some embodiments, monofilament 48 may be similar to monofilament 26 in all respects, except that reducing member 9, which is integral with monofilament 26, is lacking.

In some embodiments, reducing member 50 may have a tubular portion 51 and a slab portion 52. In the un-deployed state, slab portion 52 may be configured to fit side-by-side with monofilament 48 in the lumen of a needle 4. In some embodiments, reducing member 50 may be attached to the distal end 49 of monofilament 48. Tubular portion 51 of reducing member 50 may be configured to receive distal end 49 of monofilament 48. In some embodiments, attachment of reducing member 50 to monofilament 48 may be made using any means known in the art, such as welding, crimping or gluing. In some embodiments, reducing member 50 may be cut from a nitinol tube.

Reference is now made to FIGS. 9A-C, which depict the deployed state of device 47 according to some embodiments. In some embodiments, the deployed shape of monofilament 48 includes support portion 6 and filter portion 53. Monofilament 48 may also optionally include stem 25.

Optionally, one or more of stopper 18, anchor 19, and pull wire 20 may also be included. Support portion 6, stopper 18, anchor 19, and pull wire 20 have already been described and therefore their detailed description is omitted.

In some embodiments, the deployed shape of filter portion 53 may have a funnel portion 54 substantially similar to funnel portion 8 of device 17, except that distal tip 49 may be turned or twisted such that slab portion 52 of reducing member 50 may be oriented to bisect the distal-most coil 55 of funnel portion 54. Thus, slab portion 52 may reduce the size of the maximal embolus that may pass through device 47 by a factor of about 2.

Example

Monofilament 48 is made from nitinol. The diameter d of monofilament 48 is 0.22 mm, which provides device 47 with sufficient stiffness to maintain its shape in the pulsating carotid environment, yet provides enough flexibility to allow loading into a needle. The maximal allowable strain in monofilament 48 is $\varepsilon=8\%$: otherwise, the shape memory of nitinol is lost and recovery of the desired deployed shape of device 48 is impossible. Given the specified parameters, the minimal allowable diameter of the smallest coil is $d/\varepsilon=0.22/0.08=2.75$ mm. Thus, all emboli sized 2.75 mm or less will get through device 47, and major stroke may be caused by these emboli. On the contrary, the advent of reducing member 50 bisecting coil 55 reduces the maximal embolus size that may get through to about 1.4 mm. This significantly improves the ability of device 47 to prevent major stroke while the diameter of monofilament 48 is maintained at 0.22 mm.

An embolic protection device 56 according to some embodiments of the present disclosure is depicted in FIGS. 10 and 11A-C.

Reference is made to FIG. 10, which depicts the un-deployed state of device 56 according to some embodiments. In some embodiments, device 56 may be substantially similar to device 47, except that monofilament 48 is replaced with monofilament 57 and reducing member 50 is replaced with reducing member 59.

In some embodiments, reducing member 59 may be formed by making slots in a tube, such that one or more tubular portions 60 and one or more protruding portions 61 are formed. The tube may be made from a shape memory alloy, such as nitinol. In the un-deployed state, reducing member 59 may be configured to reside in the lumen of needle 4. In some embodiments, one or more protrusions 61 may be configured to be approximately collinear with monofilament 57. In some embodiments, reducing member 59 may be attached to the distal end 58 of monofilament 57. The most proximal tubular portion 60 of reducing member 59 may be configured to receive distal end 58 of monofilament 57. In some embodiments, attachment of reducing member 59 to monofilament 48 may be made using any means known in the art, such as welding, crimping or gluing.

Reference is now made to FIGS. 11A-C, which depict the deployed state of device 56 according to some embodiments. In some embodiments, monofilament 57 may be similar to monofilament 48 in all respects, except that distal-most coil 55 may be lacking. In some embodiments, reducing member 50 may be replaced with reducing member 59. In the deployed state of device 56, reducing member 59 is shaped as a coil. One or more protruding portions 61 extend towards the center of the coil thereby reducing the maximal size of an embolus that may pass through device 56.

An embolic protection device 62 according to some embodiments of the present disclosure is depicted in FIGS. 12 and 13A-C. Device 62 may be constructed from a monofilament 63. In some embodiments, monofilament 63 may be similar in terms of material, length, diameter and cross-section to monofilament 2. In some embodiments, Device 62 may include an optional stopper 65 and a reducing member 66. In some embodiments, optional stopper 65 and reducing member 66 may be integral with each other. In some embodiments, stopper 66 may be cut from a tube made from shape memory alloy, such as nitinol. In some embodiments, reducing member 66 may be cut from a tube made from a shape memory alloy, such as nitinol. In some embodiments, stopper 65 and reducing member 66 may be cut from the same tube. In some embodiments, stopper 65 and reducing member 66 may both be integral with a common tubular member 67, together forming a stopper/reducer 64. In some embodiments, device 62 may optionally include an anchor 19 and a pull wire 20. Both the anchor and the pull wire were described earlier in this disclosure, and therefore their detailed description is omitted.

Reference is made to FIG. 12, which depicts device 62 in its un-deployed state according to some embodiments. In some embodiments, in the un-deployed state device 62 or a portion thereof is configured to fit within the lumen of a needle. In some embodiments, the entire device 62 may have a linear or substantially linear un-deployed shape (and, in some embodiments, may be non-linear or substantially non-linear). In some embodiments, stopper 65 may have an un-deployed state and a deployed state. In the un-deployed state, stopper 65 may lie side-by-side with monofilament 63 in the lumen of needle 4. In some embodiments, reducing member 66 may lie side-by-side with monofilament 66 in the lumen of needle 4.

Reference is made to FIGS. 13A-C, which depict the deployed shape of device 62 according to some embodiments. In some embodiments, the deployed shape of monofilament 63 may include the shape of a wound wire comprising coils or turns of varying sizes. In some embodiments, all turns may be wound in the same direction, for example, the clockwise direction or the counter clockwise direction. In some embodiments, the deployed shape of monofilament 63 may include a lead portion 69, a support portion 70, a funnel portion 72, and a stem 25. In some embodiments, funnel portion 72 and reducing member 66 together form filter portion 71.

In some embodiments, lead portion 69 may be located near the distal end 68 of monofilament 63. In some embodiments, lead portion 69 may include one or more coils whose diameter is less than the diameter of vessel 5. In some embodiments, the function of the lead portion 69 is to orderly guide the exit of monofilament 63 as it is deployed from a needle 4 in the lumen of blood vessel 5.

In some embodiments, support portion 70 may be shaped as a helix having a diameter that, when unconstrained, may be less than, equal to or greater than the diameter of the lumen of blood vessel 5. In some embodiments, support portion 70 may be configured to at least one of: aid in proper orientation of a filter portion 71 of the device within the blood vessel 5, and secure device 62 to the vessel walls via radial pressure and/or subsequent growth of cells from the vessel wall.

In some embodiments, funnel portion 72 may be shaped as a helix that tapers down in the direction from the distal end 68 of monofilament 63 to its proximal end 21. In some embodiments, the minimal distance between consecutive coils of the funnel portion may be in the range of 0.3 and 1.5 mm. In some embodiments, the minimal distance between consecutive coils of the funnel portion may be less than about 1.5 mm, thereby preventing emboli that may cause mayor stroke from passing through the coils of the funnel portion.

In some embodiments, a stem 25 may be included, which may be approximately linear in shape, and can be configured to traverse a wall of the vessel. In some embodiments, the stem 25 is arranged perpendicular to longitudinal axis of the vessel and vessel wall. The stem may be arranged along a bisector of the cross section of the vessel (see FIG. 13C).

In some embodiments, the function of the stem is to prevent migration of device 62 from its implantation location, and/or to enable anchoring of device 62 in tissue external to the vessel wall proximate the puncture in the vessel wall through which filament 63 is deployed in the vessel lumen.

In some embodiments, in the deployed state of device 62, reducing member 66 is configured to be collinear with stem 25. In some embodiments, reducing member 66 is configured to ensure that the maximum gap in device 62 is sufficiently small so as to enable emboli of clinically relevant size to be trapped. Reducing member, in some embodiments, may be useful since in filament 63, made from a shape memory alloy, there is a maximal strain that, when exceeded, disables shape recovery following deployment from a needle. Typically, with nitinol, the maximal strain is about 8%. This maximal strain and wire diameter determine a minimal radius of curvature that the device may have. For example, the minimal radius of curvature of a 180 micron diameter nitinol wire is 1.1 mm. Therefore all particles less than about 2.2 mm in size can pass through the proximal-most turn in funnel portion 72. Accordingly, reducing member 66 bisects the proximal-most turn of funnel portion 72, thereby halving (approximately) the maximal gap and preventing all emboli larger than 1.1 mm in size from getting through. In some embodiments, in the deployed state, reducing member 66 may be a loop, hook, zig-zag, or any other structure configured to reduce the maximal gap in the proximal-most coil of funnel portion 72.

In some embodiments, in the deployed state, stopper 65 may protrude, like a wing or a petal, laterally from stem 25. In some embodiments, the stopper may be configured to resist transition from the lumen of the vessel to the exterior of the vessel. In some embodiments, the stopper may be configured to prevent filament 63 from moving out of the vessel lumen through the puncture in the vessel wall.

In some embodiments, an anchor 19 may be included. Because the anchor has been described above in detail, its detailed description is omitted here. In some embodiments, the anchor may be configured to rotate around the stem.

In some embodiments, a pull wire may be included. Because the pull wire has been described above in detail, its detailed description is omitted here.

In some embodiments, a bearing 73 may be included and may be made from metal, such as steel, or shape memory alloy, such as nitinol, and is configured to enable rotation of pull wire 20 with respect to monofilament 63, thereby preventing the build-up of torsion in pull wire 20 or monofilament 63.

In some embodiments, devices 1, 17, 27, 35, 47, 56, and 62 may include one or more of the following attributes (any combination):
a hemo-compatible structure made from a single filament whose diameter is less than about 0.3 mm;
ability to transition from the deployed to the un-deployed shape and back without plastic deformation;
sufficient structural rigidity to withstand harsh blood flow and pulsatility conditions in blood vessels, and, in particular, in the carotid artery;
resistance to migration;
a maximal opening size less than about 1.5 mm, which is required to prevent major stroke;
a support portion having at least one coil whose height or pitch is greater than its diameter, or even 1.5 times the diameter, which resists the axial compression of the support portion;
a support portion having at least a portion of one coil whose height or pitch is greater than its diameter, or even 1.5 times the diameter, which resists the axial compression of the support portion. For example, one quarter or one half of a coil whose height is greater than its diameter is possible;
stability in pulsatile flow (e.g., no flailing and/or tilting);
support portion resisting vessel spasms by virtue of its radial strength;
robustness against dynamic reduction in vessel diameter; and/or
less thrombogenicity, e.g., less metal in the blood flow, most metal located proximate the vessel wall, where it gets covered by tissue.

Some of the embodiments of devices 1, 17, 27, 35, 47, 56, and 62 may include one or more of the following features (any combination):
a filament that has a length between about 70 mm and about 300 mm;
at least one of the needle end and the distal end of the device is configured for puncturing the blood vessel in the vicinity of the implantation site;
the mono filament includes a substantially circular cross-section;
the diameter of the mono filament is less than about 0.25 mm;
the monofilament comprises a hollow lumen;
one or more of a radiopaque marker, an echogenic marker, a radioactive marker, a magnetic marker, and a magnetic resonance marker;
the anchor may comprise at least one of a loop, a roughened surface, a barb, a micro-barb, a hook, a bulge, and a material configured to enlarge upon contact with an aqueous environment;
the anchor may be rotatable around the stem,
the bearing may comprise housing and an axle, which may be configured to rotate in said housing with any degree of friction, and may be integral with the filament;
the bearing may be configured to release accumulated torsion or to prevent the build-up of torsion in the filament;
the device may further comprise two or more filaments, where each filament has a length, a diameter, a proximal filament end, and a distal filament end, as such, depending upon the embodiment, the filaments may joined at the proximal end or at the distal end of the device, and the two or more filaments each have a helical shape;
the support portion may include at least one coil or a portion thereof having a height Z that is less than, equal to, or greater than the coil diameter D;
at least one coil may have a height Z to diameter D ratio that is greater than 1;
at least one coil may have a height Z to diameter D ratio that is greater than 1.5;

at least one coil may have a height Z to diameter D ratio that is greater than 2; and/or the angle between the stem and the axis may be in the range of about 30 degrees and 150 degrees.

In some embodiments, such as, the embodiments 1, 17, 27, 35, 47, 56, and 62 of an embolic protection device, for example, a delivery device for delivering one and/or another device embodiments (for example) is provided, and may comprise a needle having a lumen, a sharp distal end, and an outer diameter less than about 1 mm, and a pusher slidable within the needle. The delivery device may also include at least one of a needle handle and a pusher handle. In some embodiments, a method for implanting an embolic protection device in a patient's vessel containing fluid flow is provided and may include one or more, and in some embodiments, several, and, in some embodiments, all of the following steps: providing a needle having a lumen and a sharp distal end, providing a pusher slidable within the lumen of the needle, providing a device having a distal end, an un-deployed state, and a deployed state where in the un-deployed state at least a portion of the device is loaded within the lumen, making a puncture in a wall of the vessel using the sharp distal end of the needle or the distal end of the device, and exteriorizing the device through said needle and said puncture by advancing the pusher, retracting the needle, or both, such that the axis of the supporting coils ends up approximately parallel to the fluid flow direction.

Some embodiments of an embolic protection system and method 73 are depicted in FIGS. 14A-E.

In some embodiments, embolic protection system 73 may include embolic protection device 1, needle 4, pusher 78, push tube 79, rack 77, spur 76, motor 75, power supply 82, controller 74, input/output device 84, and housing 85. In some embodiments, motor 75, spur 76, and rack 77 may form a driving mechanism 86. In some embodiments, device 1, or at least a portion thereof, may be positioned in its un-deployed state within the lumen of needle 4. Pusher 78, or at least a portion thereof, may also be arranged in the lumen of needle 4. In some embodiments, distal end 87 of pusher 78 may be arranged proximally to the proximal end 10 of device 1. In some embodiments, push tube 79 may be mechanically connected at its proximal end 88 to the proximal end 89 of push tube 78. In some embodiments, the proximal ends of the push tube and the pusher may be welded together. In some embodiments, push tube 79 may house on its outside rack 77. In some embodiments the teeth of rack 77 may interlock with the teeth of spur 76. In some embodiments spur 76 may be rotated in the clockwise and/or counterclockwise directions by motor 75. In some embodiments, motor 75 may receive power from power supply 82. In some embodiments power supply 82 and motor 75 may be controlled by controller 83. In some embodiments, controller 83 may receive an input and/or provide an output to input/output device 84.

In some embodiments, needle 4 may be made from a metal, such as stainless steel, or from a polymer. In some embodiments, tip 80 of needle 4 may be sharpened. In some embodiments, needle 4 may be a hypodermic needle, an epidural needle, or a biopsy needle. In some embodiments the outside diameter of needle 4 may be less than about 1 mm. In some embodiments, the diameter of needle 4 may be less than 0.7 mm. In some embodiments, the inside diameter of needle 4 may be greater than about 0.2 mm. In some embodiments, needle 4 may have a portion that is linear. In some embodiments, needle 4 may have a portion that is curved. In some embodiments, needle 4 may be wound on a drum.

In some embodiments, pusher 78 may be made from a metal, such as stainless steel, or from a polymer. In some embodiments, pusher 78 may have a circular cross section.

In some embodiments, push tube 79 may receive the proximal end of needle 4 in the distal end of the lumen of push tube 79. In some embodiments, push tube 79 may contain and constrain pusher 78 even if it buckles as it pushes device 1 out of the lumen of needle 4.

In some embodiments, rack 77 may be made from a polymer. In some embodiments, rack 77 mat be integral with push tube 79.

In some embodiments, motor 75 may be an electrical motor, such as an AC motor, a DC motor, or a stepper motor. In some embodiments, power supply 82 may be a battery, which may or may not be rechargeable.

In some embodiments, controller 83 may include a printed circuit board, a memory, and a central processing unit. In some embodiments, controller 83 may be configured with software residing in the memory.

In some embodiments, input/output device 84 may include an operating button. In some embodiments, input/output device 84 may be voice operated.

In some embodiments, housing 85 may include at least a portion of needle 4, motor 75, power supply 82, controller 83 and input/output device 84. In some embodiments, housing 85 may be made from plastic.

In some embodiments, system 73 may include a reusable part including the housing, input/output device, controller, power supply, motor, and spur. In some embodiments, the disposable part may include needle 4, device 1, and pusher 78, push tube 79 and rack 77. In some embodiments, device 73 may be provided sterile. In some embodiments, the disposable part may be provided sterile.

In some embodiments, device 1 may be provided in varying sizes. For example, the device may be provided in diameters ranging from 4 mm to 10 mm in 0.5 mm jumps.

In some methods of operation, the operator may first use an imaging modality such as ultrasound, CT, MRI, or x-ray fluoroscopy to assess the diameter of the target vessel 5 at the implantation site. In some methods, the operator may then choose a system 73 configured with an implant 1 having a diameter D between 0 and 2 mm over the diameter of the target vessel 5. In some methods, the operator may locally anesthetize the vicinity of the target implantation site using local anesthesia. Subsequently, the operator may advance system 73 towards the target implantation site, puncturing skin 81 and vessel 5. In some methods, the operator may puncture vessel 5 along a bisector of the cross section of the vessel, perpendicularly to the vessel wall (FIG. 14B). The vessel puncture may be made under imaging guidance, such as ultrasound, x-ray fluoroscopy, CT or MRI.

Figure 14A:
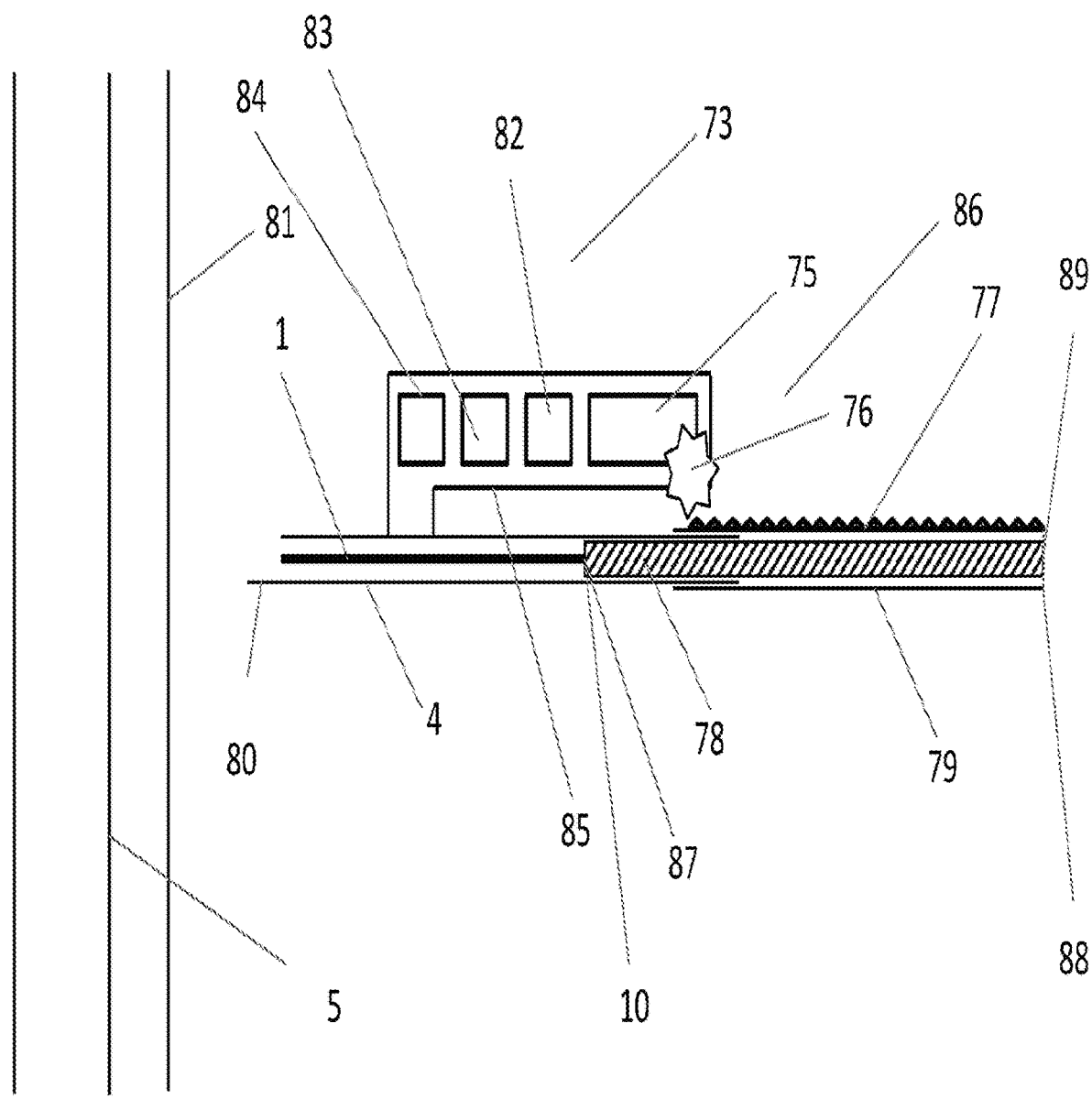
Figure 14C:
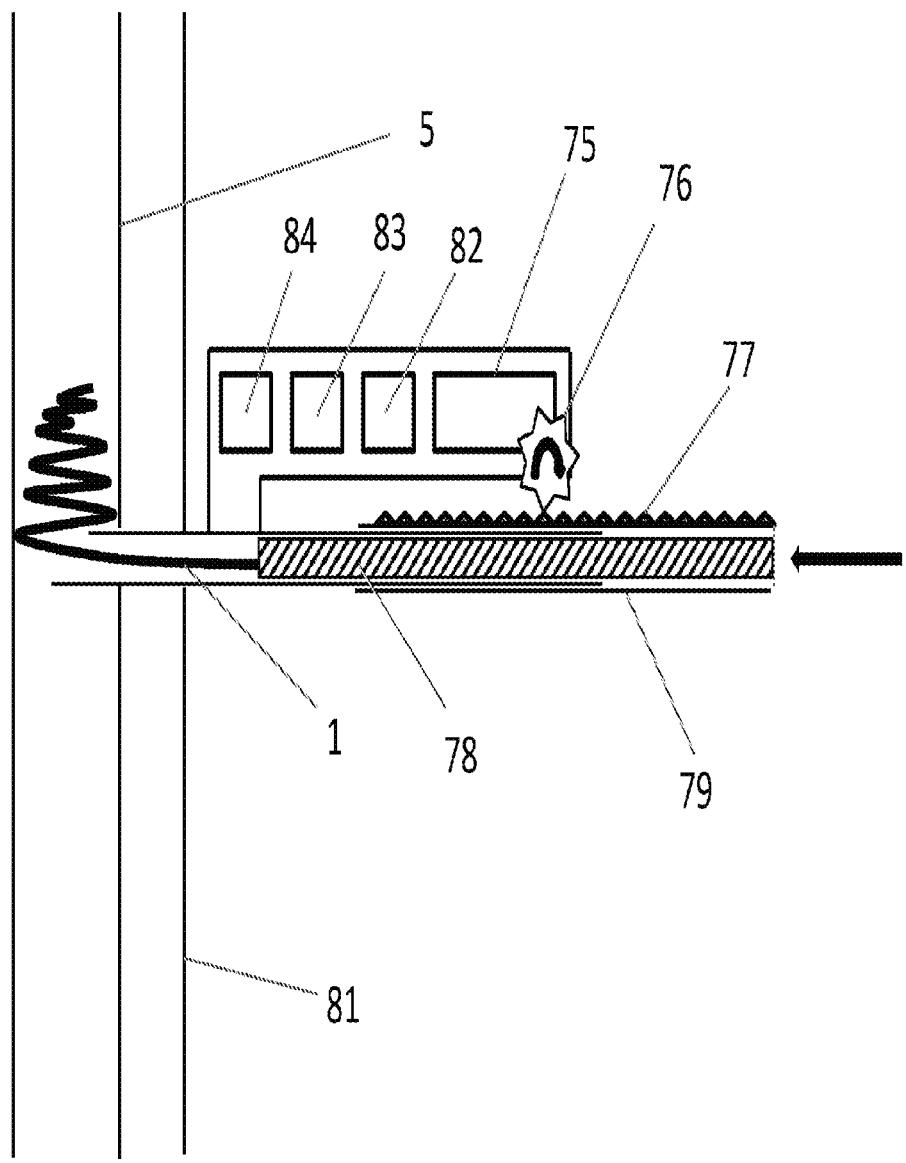

In some methods, once the distal tip 80 of needle 4 is within the vessel lumen, the operator may instruct system 73 to exteriorize device 1 from needle 4 (FIG. 14C). In some embodiments of system 73, the instruction may be given using input/output device 84. In some embodiments, the input signal may be the pressing of a button. In some embodiments, the input signal may be a voice command. In some embodiments, the input signal may cause controller 83 to provide power from power supply 82 to motor 75. In some embodiments, motor 75 may cause spur 76 to rotate in, thereby causing pusher 78 to move towards the tip 80 of needle 4. In some embodiments, the distal end of the pusher may push on the proximal end of the device 1, thereby causing it be exteriorized from needle 4. In some embodiments, as device 1 is exteriorized from needle 4 it assumes its deployed shape, with the axis of the supporting coils in contact with the inner wall of vessel 5. In some methods, the filter portion may point caudally or cranially. In some embodiments, when device 1 is fully exteriorized (FIG. 12D) input/output device 84 may beep or make a visual indication, such as the lighting of a LED.

Figure 14E:
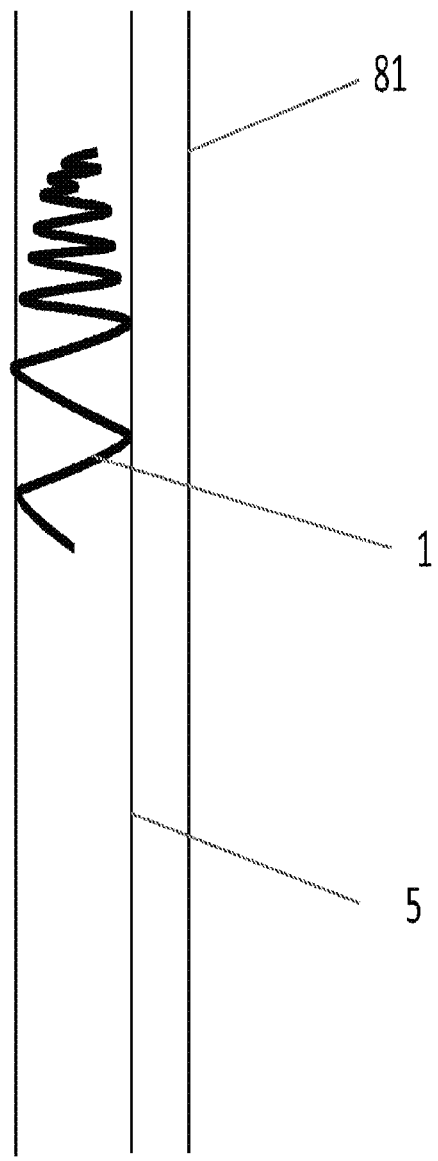

In some methods, once exteriorization is complete, system 73 may be removed from the patient's vessel, with device 1 securely implanted in vessel 5 (FIG. 14E).

Some embodiments of an embolic protection system 74 and method of use thereof are depicted in FIGS. 15A-G.

In some embodiments, system 74 is similar to system 73 except that: (1) device 1 is exchanged for a version of device 17 including monofilament 28, stem 25, and pull wire 20, but lacking an anchor and a stopper, and (2) pusher 78 is exchanged for a pusher 90 that has a hollow lumen. In some embodiments, pull wire 20 of device 17, or a portion thereof, may initially reside in the lumen of pusher 20.

In some embodiments, device 17 may be provided in varying sizes. For example, the device may be provided in diameters ranging from 4 mm to 10 mm in 0.5 mm jumps.

In some methods of operation, the operator may first uses an imaging modality such as ultrasound, CT, MRI, or x-ray fluoroscopy to assess the diameter of the target vessel 5 at the implantation site. In some methods, the operator may then choose a system 74 configured with an implant 17 having a diameter D between 0 and 2 mm over the diameter of the target vessel 5. In some methods, the operator may locally anesthetize the vicinity of the target implantation site using local anesthesia. Subsequently, the operator may advance system 74 towards the target implantation site, puncturing skin 81 and vessel 5. In some methods, the operator may puncture vessel 5 along a bisector of the cross section of the vessel, perpendicularly to the vessel wall (FIG. 15B). In some methods the vessel puncture may be made under imaging guidance, such as ultrasound, x-ray fluoroscopy, CT or MRI.

In some methods, once the distal tip 80 is within the vessel lumen (FIG. 15B), the operator may instruct system 74 to exteriorize device 17 from needle 4 (FIG. 15C). In some embodiments, the instruction may be given using input/output device 84. In some embodiments, the input signal may be the pressing of a button. In some embodiments, the input signal may be a voice command. In some embodiments, the input signal may cause controller 83 to provide power from power supply 82 to motor 75. In some embodiments, motor 75 may cause spur 76 to rotate in the clockwise direction, thereby causing pusher 78 to move towards the tip 80 of needle 4. In some embodiments, the distal end of the pusher may push on the proximal end of monofilament 28, or on the proximal end of a connector connecting monofilament 28 and pull wire 20, thereby causing monofilament 28 to be exteriorized from needle 4. In some embodiments, as monofilament 28 is exteriorized from needle 4 it assumes its deployed shape, with the supporting coils in contact with the inner wall of vessel 5. In some embodiments, the filter portion may point caudally or cranially. In some embodiments, when device 17 is fully exteriorized, except for stem 25 and pull wire 20 (FIG. 15D), the input/output device 84 may beep or make a visual indication, such as the lighting of a LED.

In some methods, once exteriorization of filament 28, except for stem 25, is complete, system 74 may retracted. Retraction of system 74 may expose stem 25, which may traverse the wall of vessel 5. Pull wire 20 may extend out from the patient's skin 81 (FIG. 15E).

Figure 15A:
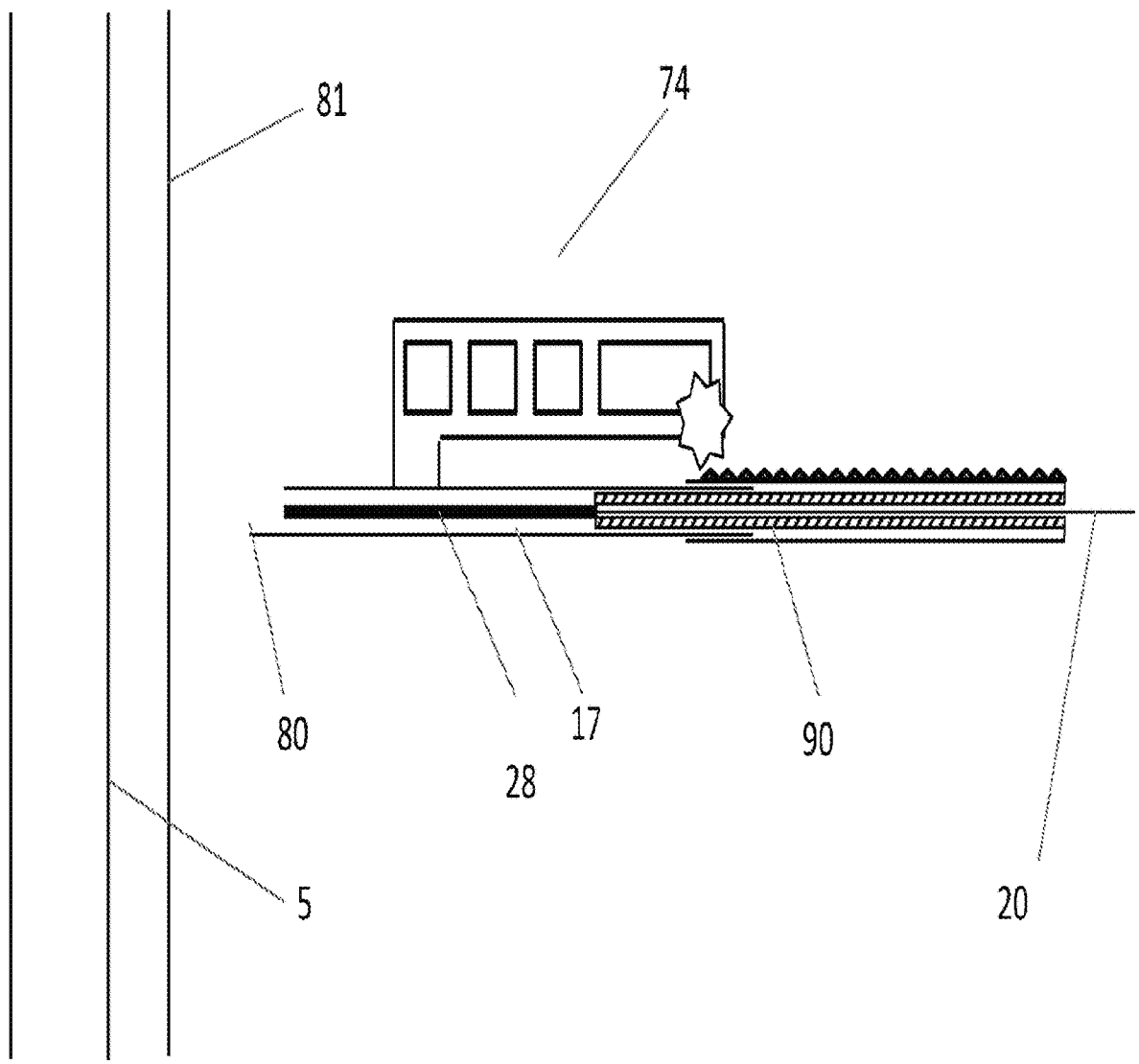
Figure 15F:
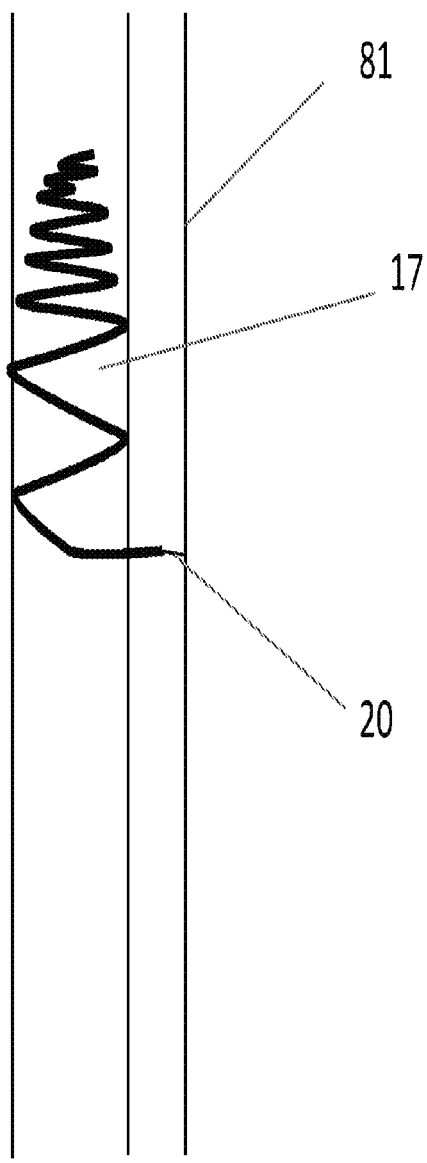
Figure 15H:
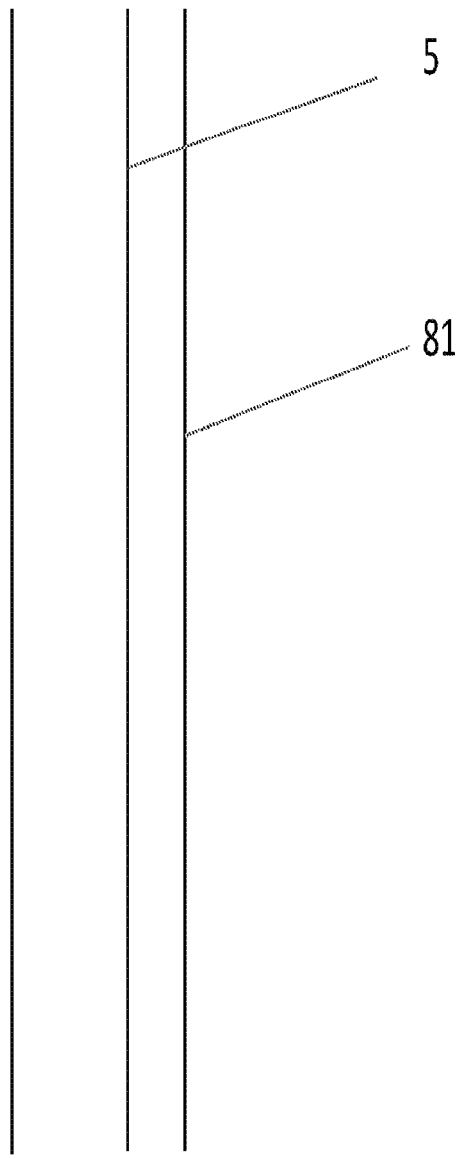

In some methods, the patient may be put under observation for an observation period ranging from several minutes to several weeks. At the end of the observation period, device 17 may be investigated using an imaging modality such as ultrasound, CT, MRI or x-ray fluoroscopy. In some methods, if the operator finds the results of the investigation satisfactory then pull wire 20 may be cut at the level of the skin. The skin may then be lifted over the proximal end of the cut pull wire 20 (FIG. 15F) and the patient may be discharged. In some methods, if the operator may conclude that device 17 should be removed, the operator may retract device 17 from vessel 5 by pulling the pull wire 20 (FIG. 15G). Device 17 may thus be completely removed from the patient's body (FIG. 15H).

Some embodiments of an embolic protection system 91 and method of use thereof are depicted in FIGS. 16A-G.

In some embodiments, system 91 is similar to system 74 except that device 17 lacking a stopper and anchor may be exchanged for any of devices 17, 27, 35, 47, 56, and 62 including at least one of a stopper 18, an anchor 19, a stem 25 and a pull wire 20. In some embodiments, pull wire 20 or a portion thereof may initially reside in the lumen of pusher 90.

In some embodiments, system 91 may include a device 17, which may be provided in varying sizes. For example, the device may be provided in diameters ranging from 4 mm to 10 mm in 0.5 mm jumps.

Figure 16A:
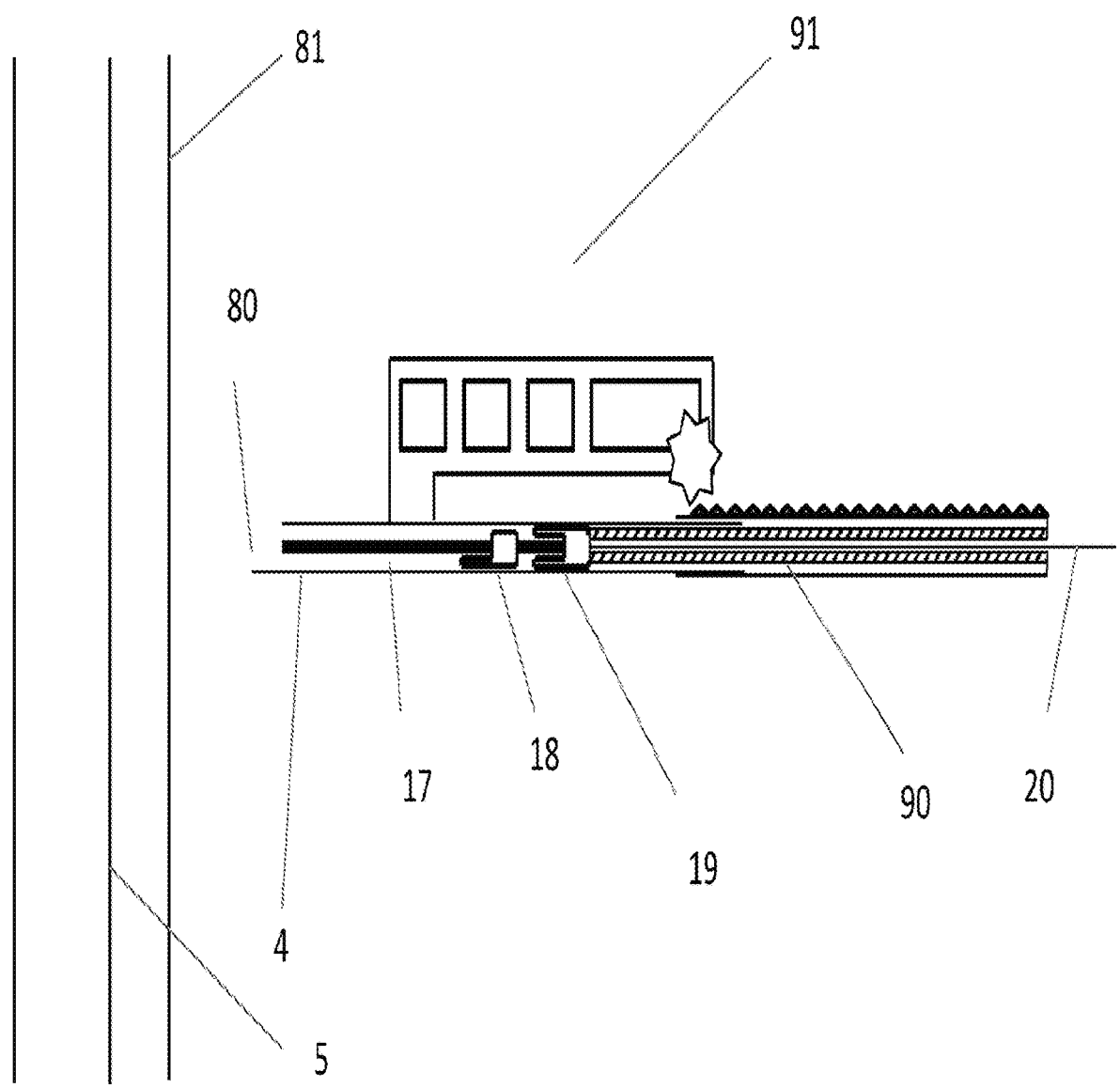
Figure 16B:
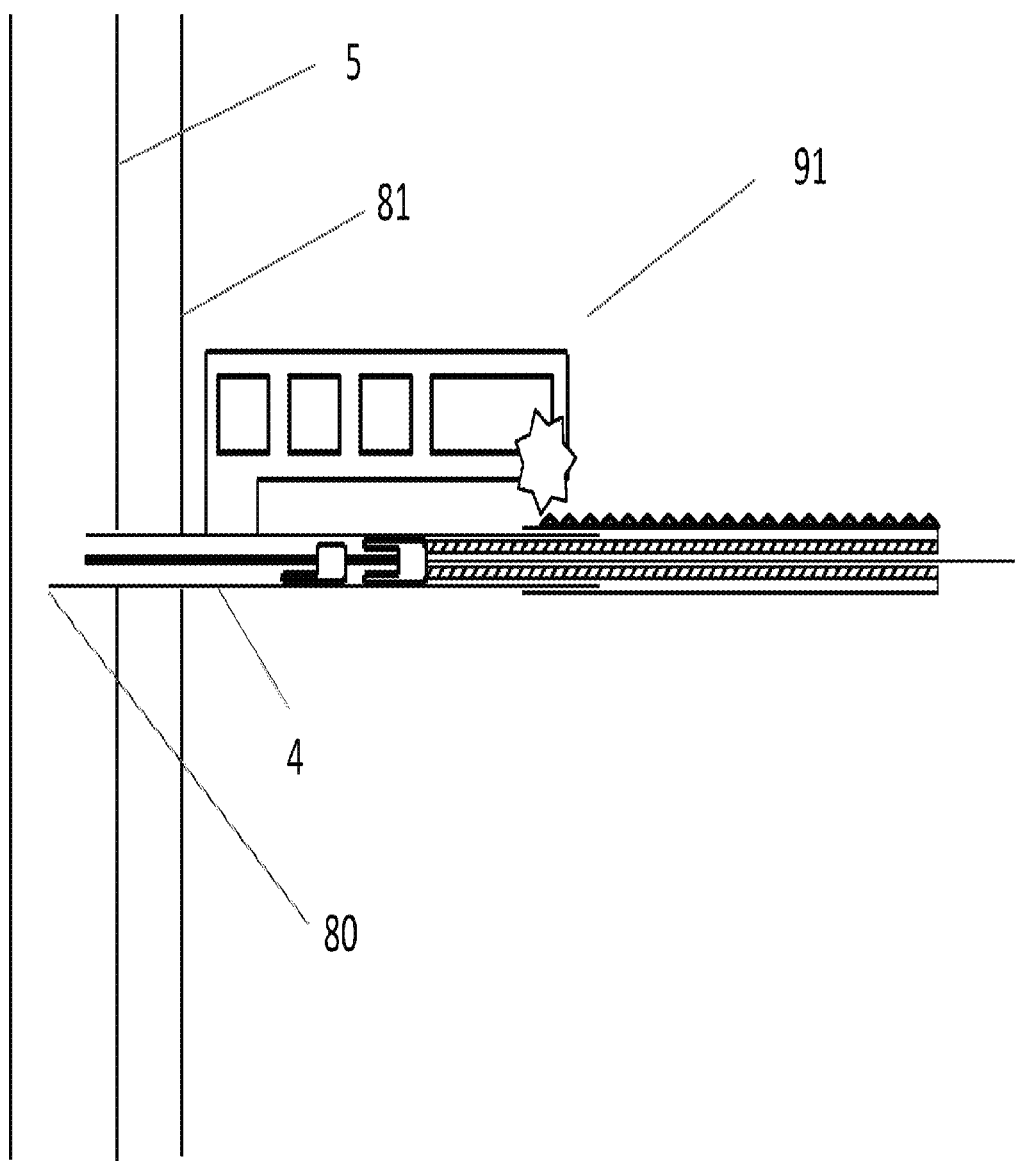
Figure 16E:
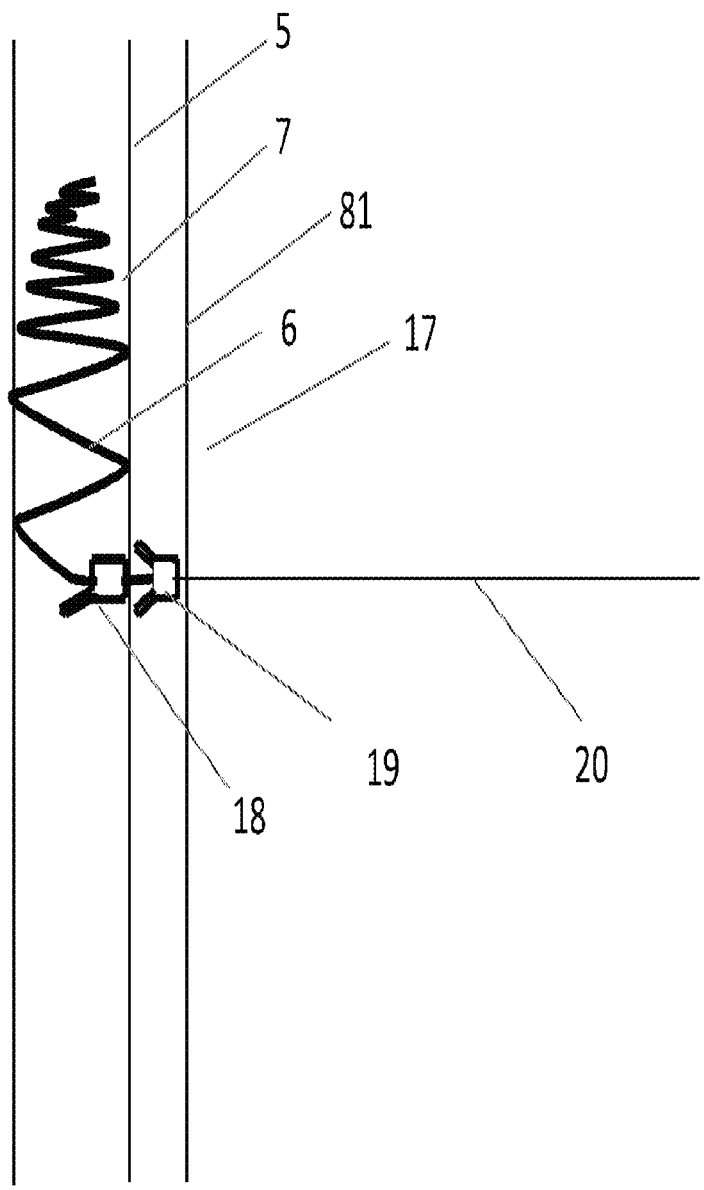
Figure 16F:
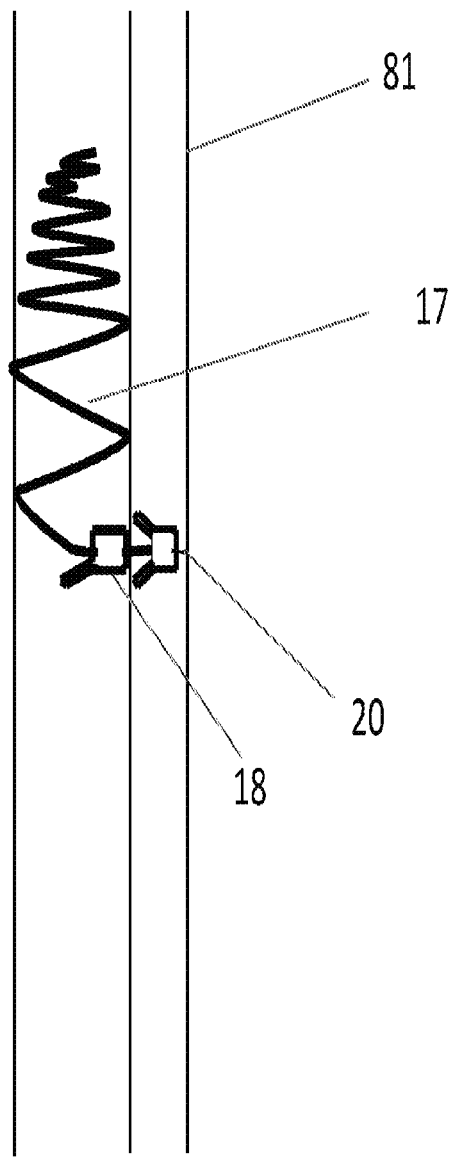
Figure 16G:
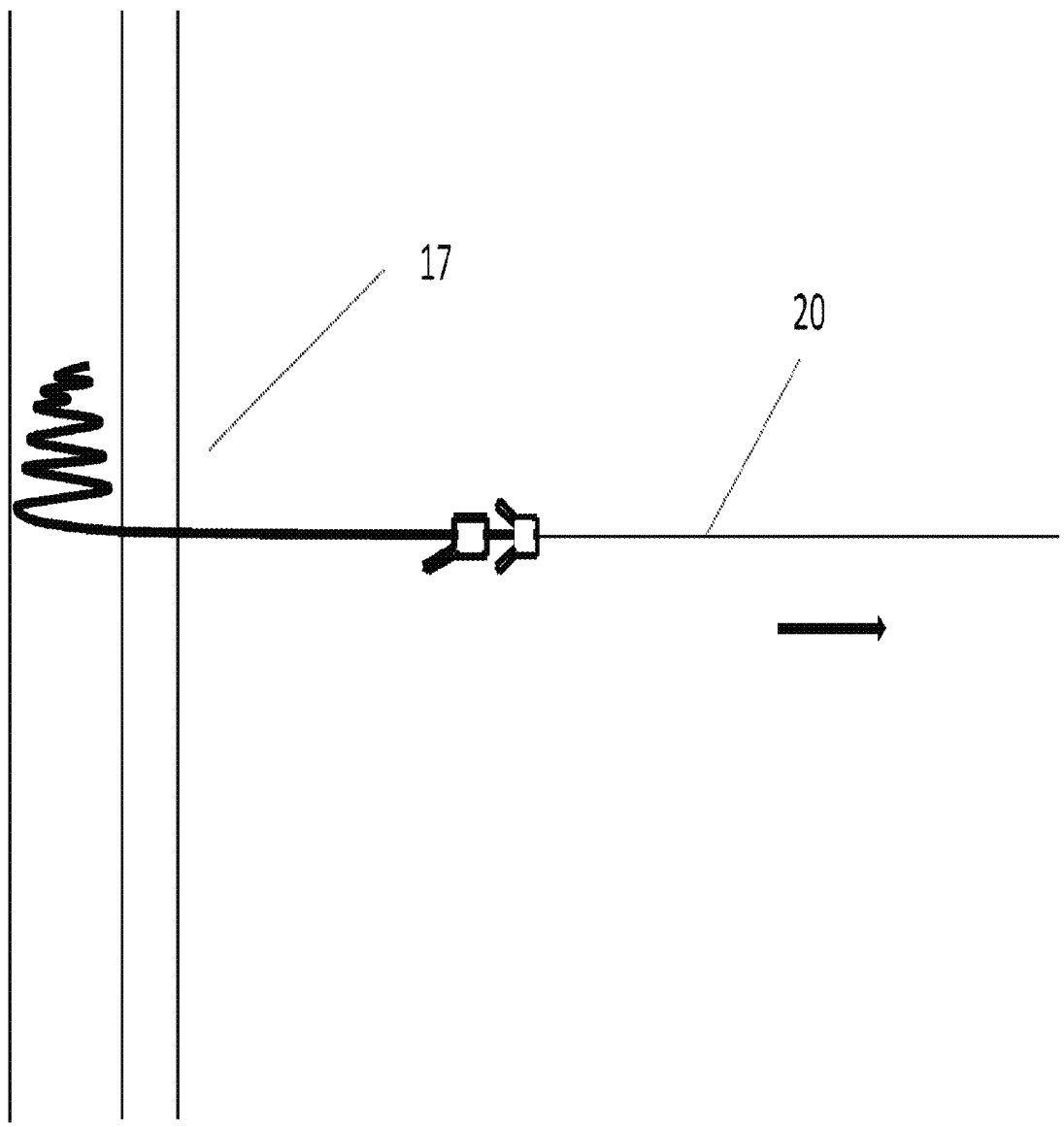
Figure 16H:
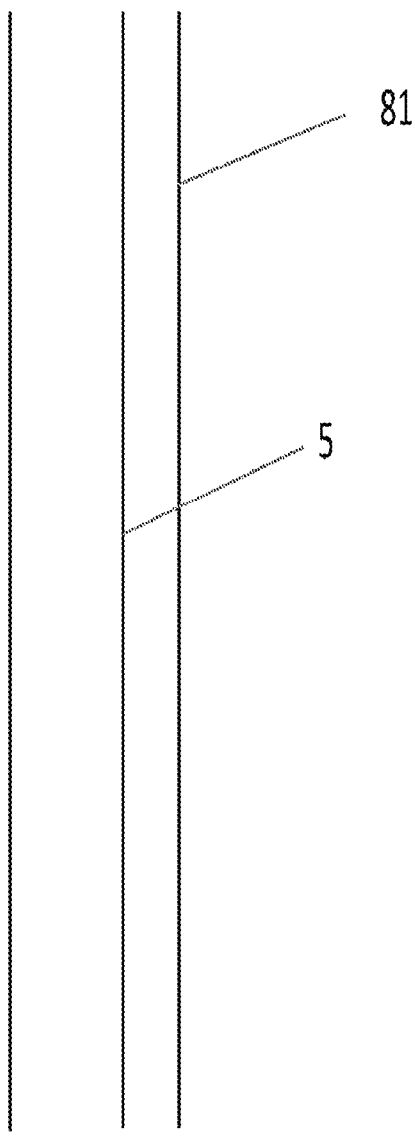

In some methods of operation, the implantation of device 17 equipped with stopper 18 and anchor 19 is substantially similar to the implantation of device 17 lacking the stopper and the anchor. In some methods, one or more of the following may be included (any combination):

stopper 18 and anchor 19 may initially reside in the lumen of needle 4 in their un-deployed state (FIG. 16A);
  skin 81 and vessel 5 may be punctured using distal tip 80 of needle 4, and tip 80 may be placed in the lumen of vessel 5 (FIG. 16B);
  system 91 may be instructed by the operator to exteriorize device 17 from the lumen of needle 4 using a command from input/output device 84 that causes controller 83 to instruct driving mechanism 86 to advance pusher 90 towards the tip 80 of needle 4 (FIG. 16C);
  the operation of motor 75 may be stopped by controller 83 when filament 28 is mostly exteriorized in the lumen of vessel 5, the stopper 18 is exteriorized in the lumen of vessel 5, but anchor 19 and pull wire 20, or a portion thereof, still reside within the lumen of needle 4 (FIG. 16D);
  system 91 may be retracted, leaving behind device 17 with filter portion 7 and supporting coils 6 within the lumen of vessel 5, stem 25 traversing the vessel wall, stopper 18 in the deployed state within the vessel lumen, anchor 19 in the deployed shape within tissue surrounding the vessel, and pull wire 20 traversing skin 81 of the patient (FIG. 16E);
  the patient may be followed up for minutes to months, and at the end of follow-up device 17 may be investigated using in imaging modality. The operator may judge the result acceptable, clip the pull wire at skin level and lift the skin over the proximal end of cut pull wire 20. The patient may be discharged (FIG. 16F); and/or
  if at the end of follow up the operator judges the result as unsatisfactory then device 17 may be retracted by pulling on pull wire 20 (FIG. 16G), until device 17 is fully retracted from the patient's body (FIG. 16H).

In some methods, the angle between the needle and the axis of the vessel during vessel puncture may be between about 30 degrees and 150 degrees.

Some embodiments of a system for implanting/delivering an embolic protection device and a corresponding method are depicted in FIGS. 17A-H.

In some embodiments, the delivery device and embolic protection device can itself form an embolic protection system 92, which may include embolic protection device 17, needle 93, pusher 94, drum 95, motor 96, pinion 101, spur 102, axle 103, power supply 97, controller 98, input/output device 99, and housing 100 (other similar embodiments may include less components). In some embodiments, motor 96, pinion 101, and spur 102 may form a driving mechanism 104. In some embodiments a planetary gear may be included, either in addition to or replacing one or more of the pinion and the spur.

In some embodiments, needle 93 may be rigidly connected to housing 100 and needle 93 may include a straight portion 105 and/or a curved portion 106. Straight portion 105 may include a portion which is arranged to reside externally to housing 100, and/or curved portion 106 may be arranged to reside within housing 100. Straight portion 105 may include a sharp distal end 107 configured to puncture skin 81 and blood vessel 5. Curved portion 106 may include one or more coils or turns. Needle 93 may be made from a metal, such as stainless steel, or from a polymer, and tip 107 may also be sharpened. In some embodiments, needle 93 may be a hypodermic needle, an epidural needle, or a biopsy needle. The outside diameter of needle 93 may be less than about 1 mm, and in some embodiments, the diameter of needle 93 may be less than 0.7 mm. The inside diameter of needle 93 may be greater than about 0.2 mm.

In some embodiments, axle 103 may be rigidly connected to housing 100, and spur 102 may be rigidly connected to drum 95. Spur 102 and drum 95 may be concentric with each other, as well as drum 95 may be configured to be rotatable around axle 103. In some embodiments, spur 102 and pinion 101 may be made from a polymer. In some embodiments, spur 102 may be integral with drum 95.

In some embodiments, device 17 may be positioned in an un-deployed state within the lumen of needle 93, and the shape of the un-deployed state of device 17 may be "inherited" from, or correspond to, the shape of needle 93. In some embodiments, device 17 may be entirely or partially within the lumen of needle 93 when un-deployed. For example, in some embodiments:
- at least a portion of device 17 may reside within the lumen of the straight portion 105 of needle 93 when un-deployed;
- at least a portion of device 17 may reside within the lumen of the curved portion 106 of needle 93 when un-deployed; and/or
- at least a portion of device 17 may reside externally to the lumen of needle 93 when un-deployed.

In some embodiments, pusher 94, or at least a portion thereof, may be arranged in the lumen of needle 93, and may also initially reside externally to the lumen of needle 93. Distal end 109 of pusher 94 may be arranged proximally to anchor 19 of device 17, and the proximal end 110 of pusher 94 may be rigidly connected to drum 95, by, for example, welding, gluing, or any mechanical or mechanical like connection known in the art. In some embodiments, pusher 94 may extend towards the proximal end of needle 93 through guides or channels.

In some embodiments, pusher 94 may be made from a metal, such as stainless steel, a super-elastic alloy such or nitinol, or from a polymer. In some embodiments, pusher 94 may have a circular cross section.

In some embodiments, pusher 94 may include a hollow lumen, such that, pull wire 20 of device 17 may be arranged within the hollow lumen, while the proximal end 111 of pull wire 20 may protrude proximally from the proximal end 110 of pusher 94.

In some embodiments, motor 96 may be configured to cause device 17 to be pushed outside of needle 93. In some embodiments, pinion 101 may be caused by motor 96 to rotate in the clockwise direction, thereby causing spur 102 and drum 95 to rotate in the counter clockwise direction, which may have the effect of driving pusher 94 in the direction of tip 107 of needle 93, thereby pushing device 17 out of the needle.

Motor 96 may receive power from power supply 97. In some embodiments power supply 97 and motor 96 may be controlled by controller 98, and controller 98 may receive an input and/or provide an output to input/output device 99.

In some embodiments, motor 96 may be an electrical motor, such as an AC motor, a DC motor, or a stepper motor, and power supply 97 may be a battery, which may or may not be rechargeable.

In some embodiments, controller 98 may include a printed circuit board, a memory, and a central processing unit. In some embodiments, controller 98 may be configured with software embedded in the memory.

In some embodiments, input/output device 99 may include an operating button. In some embodiments, input/output device 99 may be voice operated.

In some embodiments, housing 100 may include at least a portion of needle 93, motor 96, power supply 97, controller 98 and input/output device 99. In some embodiments, housing 100 may be made from plastic.

In some embodiments, device 92 may be provided sterile. For example, device 92 may comprise a reusable part and a disposable part, where the reusable part may include one or more of the housing, the input/output device, the controller, the power supply, the motor, and the pinion. The disposable part may include one or more of the needle, the embolic protection device, the drum, and the spur. The reusable and disposable parts may be reversibly connected with each other.

Figure 17A:
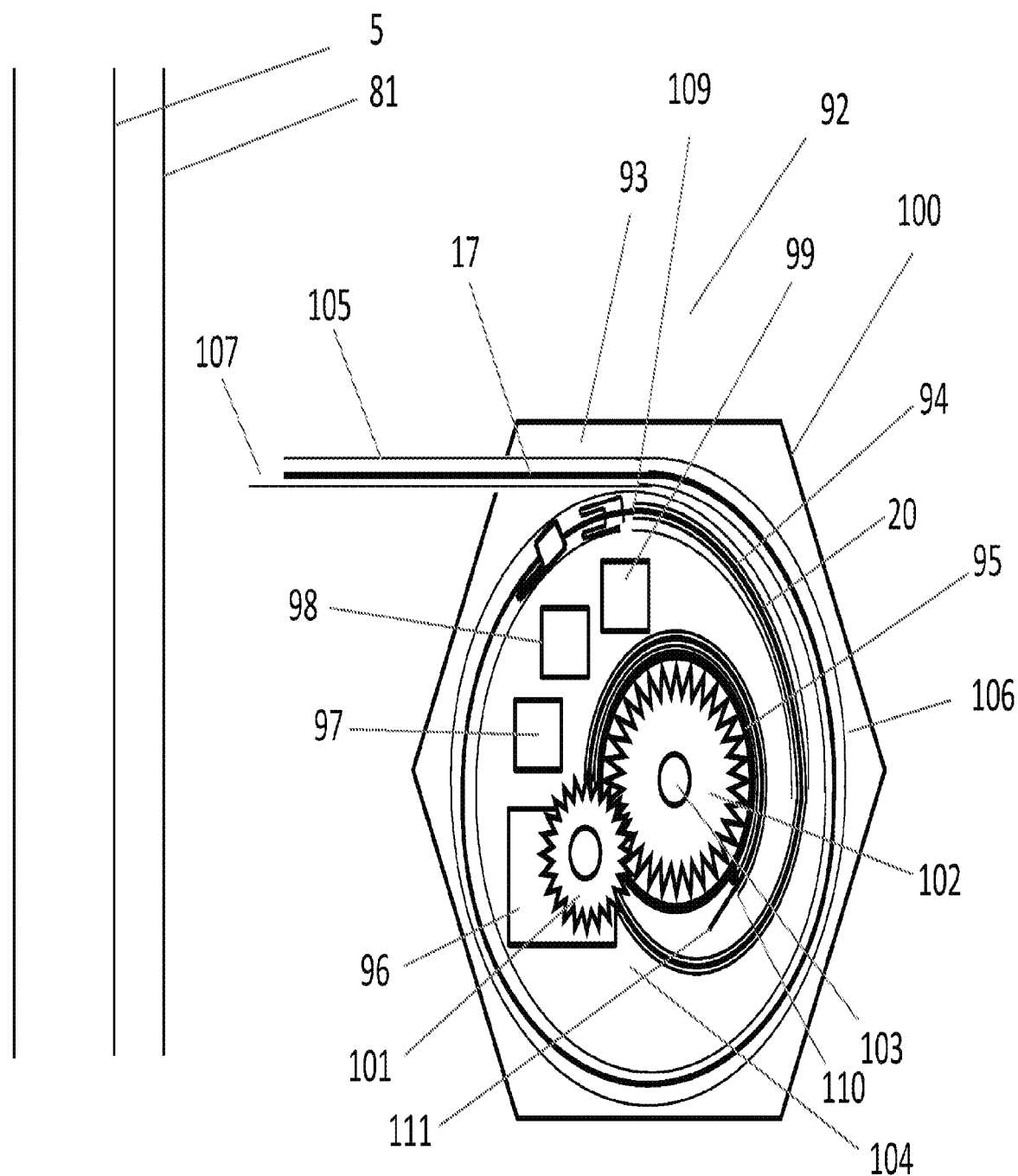
Figure 17B:
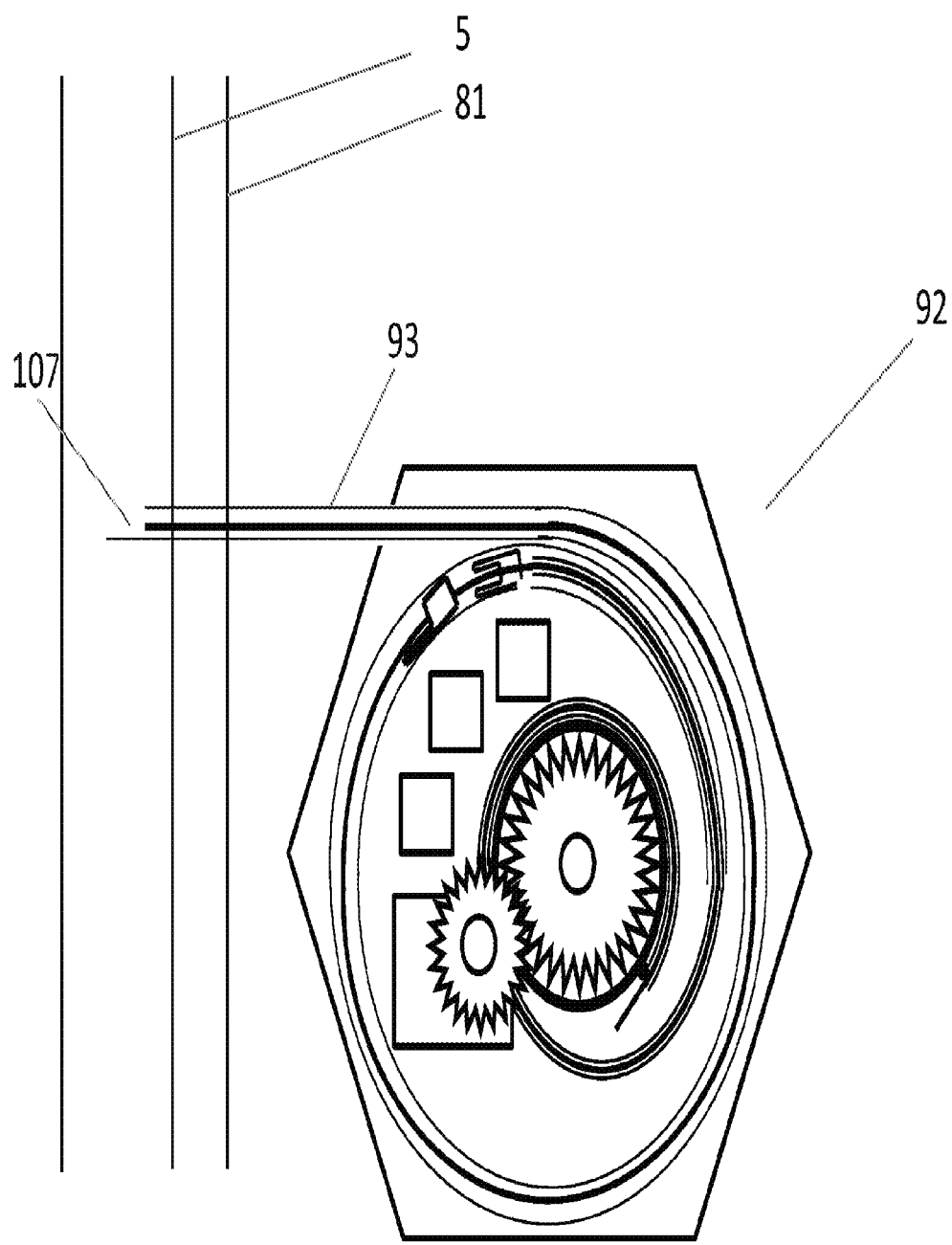

Methods of operation and provided to implant the embolic protection device using systems such as those in FIGS. 17A-H. For example, in some embodiments, an operator may first use an imaging modality such as ultrasound, CT, MRI, or x-ray fluoroscopy to assess the diameter of the target vessel 5 at the implantation site. The operator may then choose a system 92 configured with an implant 17 having a diameter D between 0 and 2 mm over the diameter of the target vessel 5. The operator may locally anesthetize the vicinity of the target implantation site using local anesthesia. Subsequently, the operator may advance system 92 towards the target implantation site, puncturing skin 81 and vessel 5. The operator may puncture vessel 5 along a bisector of the cross section of the vessel, perpendicularly to the vessel wall (FIG. 17B). The vessel puncture may be made under imaging guidance, such as ultrasound, x-ray fluoroscopy, CT or MRI.

Figure 17C:
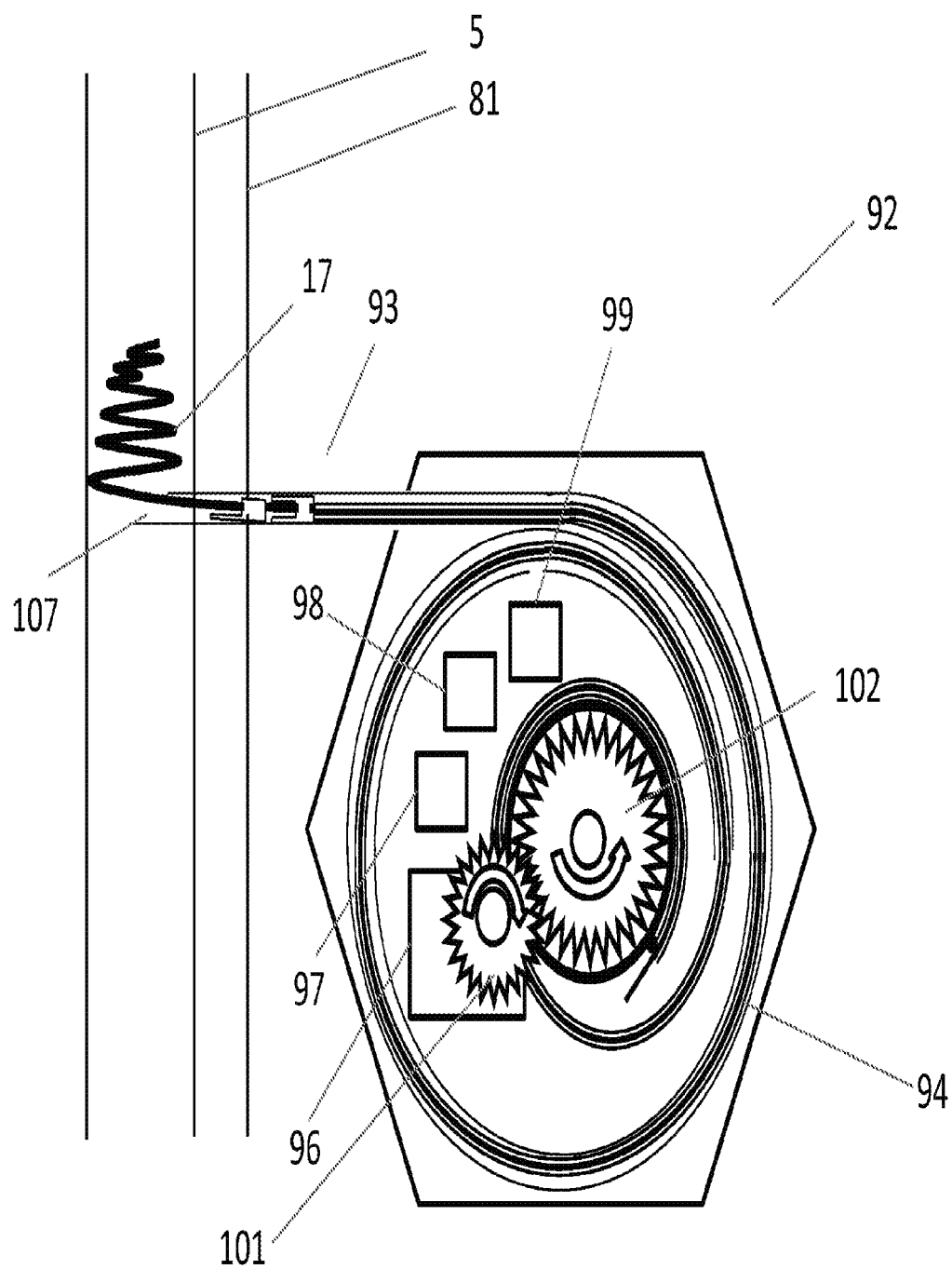
Figure 17D:
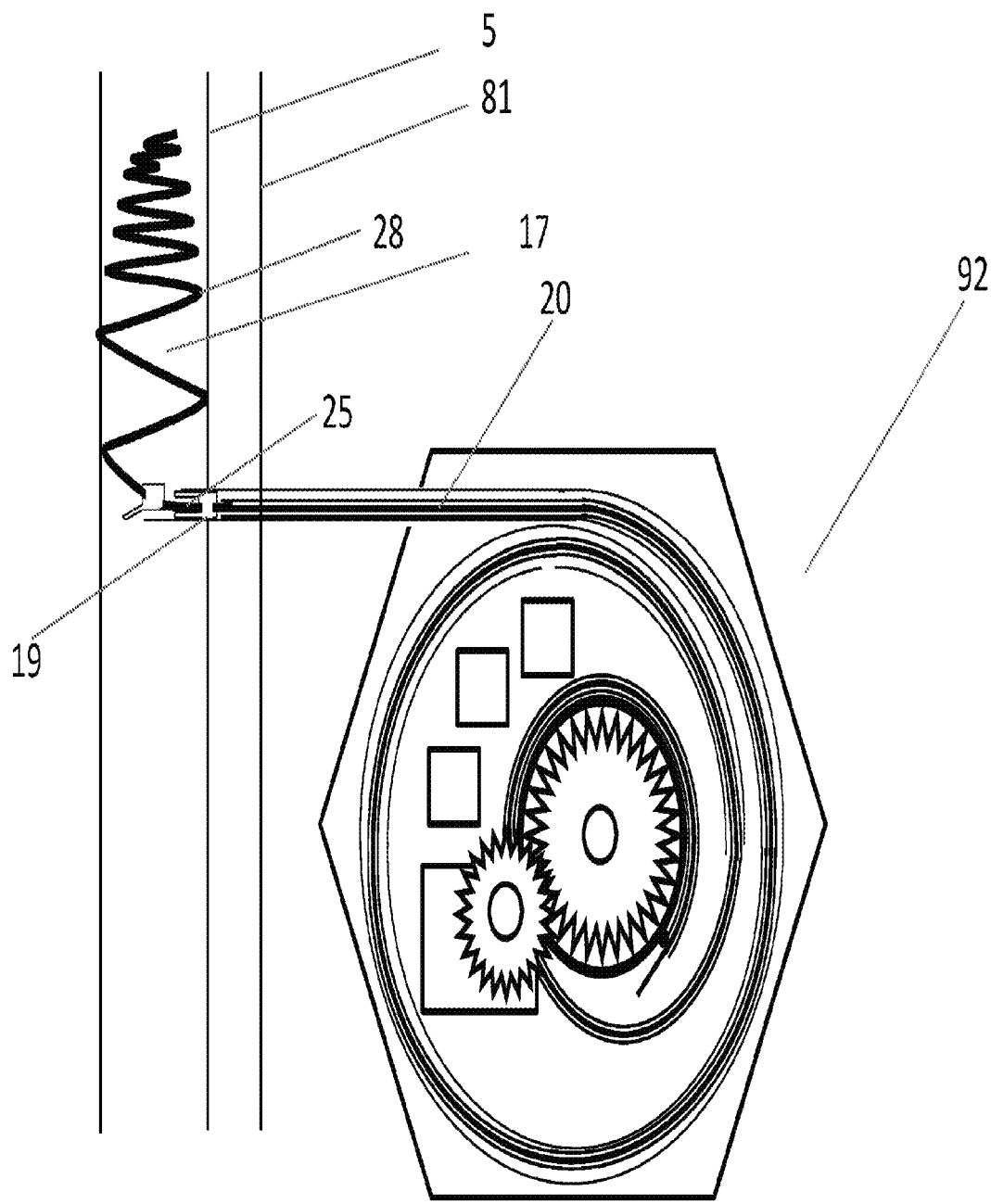
Figure 17F:
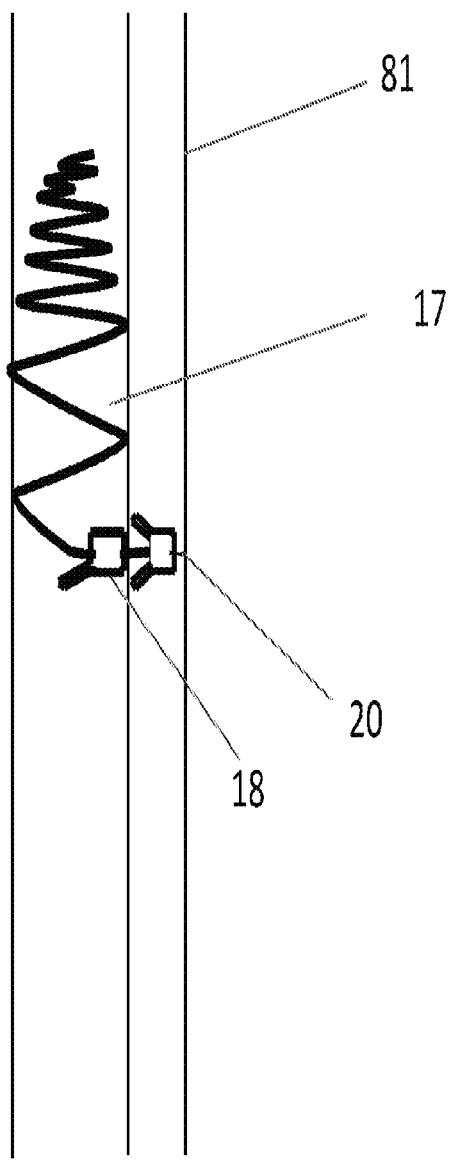

Once the distal tip 107 of needle 93 is within the vessel lumen, the operator may instruct system 92 to exteriorize device 17 from needle 93 (FIG. 17C). The instruction may then be given using input/output device 99. The input signal may be the pressing of a button and the like, but may also be a voice command, which causes controller 98 to provide power from power supply 97 to motor 96. Motor 96 may then cause pinion 101 to rotate in the clockwise direction, thereby causing spur 102 and drum 95 to rotate in the counterclockwise direction, resulting in pusher 94 advancing towards distal tip 108 of needle 93. The distal end of the pusher may push on the anchor of device 17, thereby causing it to be exteriorized from needle 93. As device 17 is exteriorized from needle 93, it assumes its deployed shape with the axis of the supporting coils arranged parallel with the inner wall of vessel 5 and the supporting coils in contact with the walls of vessel 5. In some embodiments, the filter portion may point caudally or cranially. When device 17 is fully exteriorized, except for stem 25, anchor 19, and pull wire 20 (FIG. 17D), the input/output device 99 may beep or make a visual indication, such as the lighting of a LED.

Once filament 28 is exteriorized, except for stem 25, system 92 may retracted. Retraction of system 92 may expose stem 25, which may traverse the wall of vessel 5. Pull wire 20 may extend out from the patient's skin 81 (FIG. 17E). Anchor 19 may assume its deployed state, with, for example, its wings or petals open.

Figure 17G:
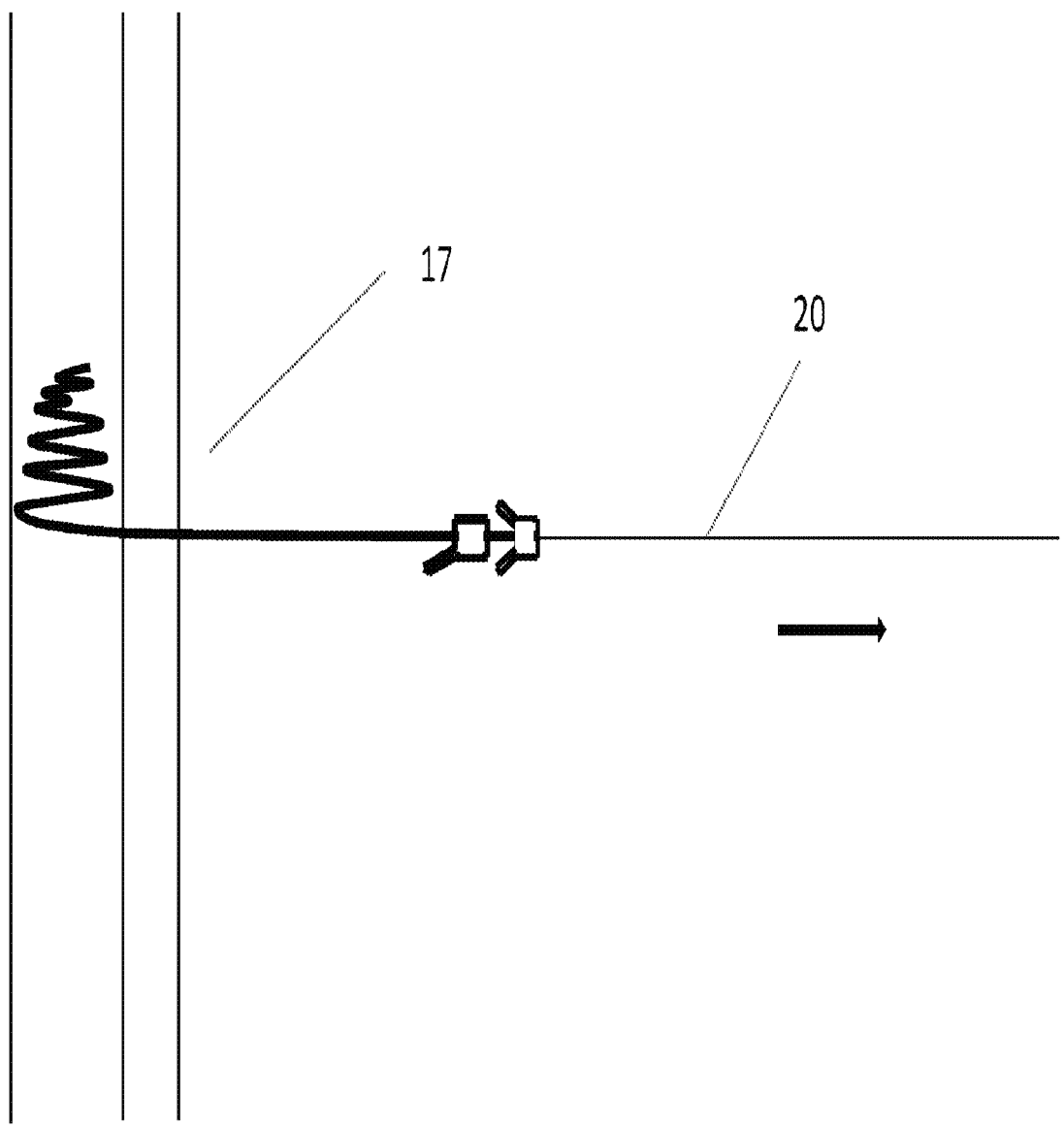
Figure 17H:
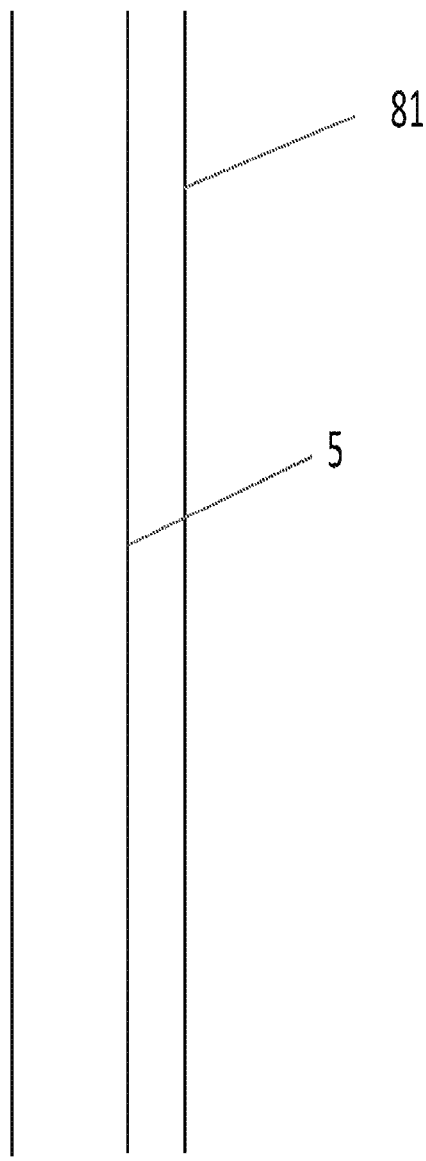

The patient may be put under observation for an observation period ranging from several minutes to several weeks. At the end of the observation period, device 17 may be investigated using an imaging modality such as ultrasound, CT, MRI x-ray, or x-ray fluoroscopy. If the operator finds the results of the investigation satisfactory, then pull wire 20 may be cut at the level of the skin. The skin may then be lifted over the proximal end of the cut pull wire 20 (FIG. 17F) and the patient may be discharged. If the operator may conclude that device 17 should be removed, the operator may retract device 17 from vessel 5 by pulling the pull wire 20 (FIG. 17G). Device 17 can thus be completely removed from the patient's body (FIG. 17H).

In some embodiments of system 92, it may be possible to replace controller, power supply, and the driving mechanism by a manual mechanism configured to cause the drum to rotate and advance the pusher towards the end of the needle, thereby exteriorizing the embolic protection device.

In some embodiments of system 92, embolic protection device 17 may be interchanged, for example, for any of devices 1, 27, 35, 47, 56, or 62.

Some embodiments of a system for implanting/delivering an embolic protection device and the associated method of delivery/implanting are depicted in FIGS. 18A-D. Embolic protection system 112 may be configured to access the implantation site of its embolic protection device in transcatheter fashion. Thus, its skin puncture site and embolic device implantation site may be remote from each other. In some embodiments, for example, the skin puncture site may be in the groin or in the arm, whereas the implantation site may be in a common carotid artery, a subclavian artery, an innominate artery, or a vertebral artery.

In some embodiments, embolic protection system 112 may be similar to system 92 except for one and/or another of the following differences (FIG. 18A), for example:
  straight portion 105 of needle 93 may be replaced with a flexible tube or catheter 113, and alternatively, needle 93 may be replaced in its entirety with a flexible tube or catheter;
  embolic protection device 17 may be replaced with embolic protection device 1; and/or
  hollow pusher 94 may be replaced with a solid pusher 114.

In some embodiments, flexible tube 113 may be made from a metal, such as nitinol, from a polymer, or from a metal-reinforced polymer. In some embodiments, the length of flexible tube 113 may be in the range of 50 and 150 cm, and the outer diameter of flexible tube 113 may be between 0.5 and 2.5 mm. In some embodiments the tip of flexible tube 113 may be soft.

In some embodiments, system 112 may be configured to access implantation site 116 via a catheter 115, which may be introduced into the patient's body as known in the art. The implantation site 116 may be remote from the entry point 118 of the catheter into the body, and implantation site 116 may be, for example, in the common carotid artery, the innominate artery, the subclavian, artery, or the vertebral artery, whereas the entry point 118 may be, for example, in the groin or in the arm.

Figure 18B:
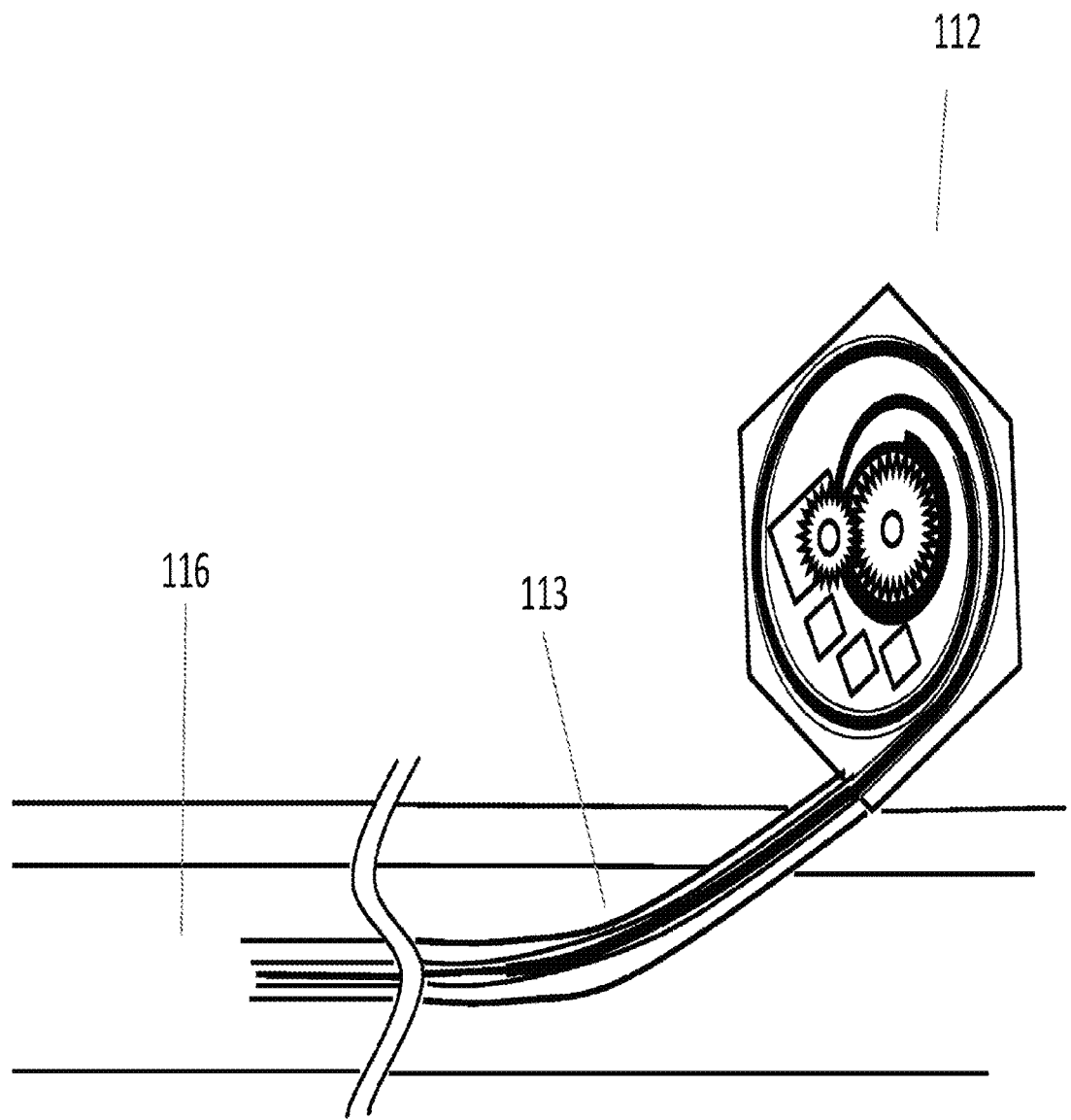
Figure 18C:
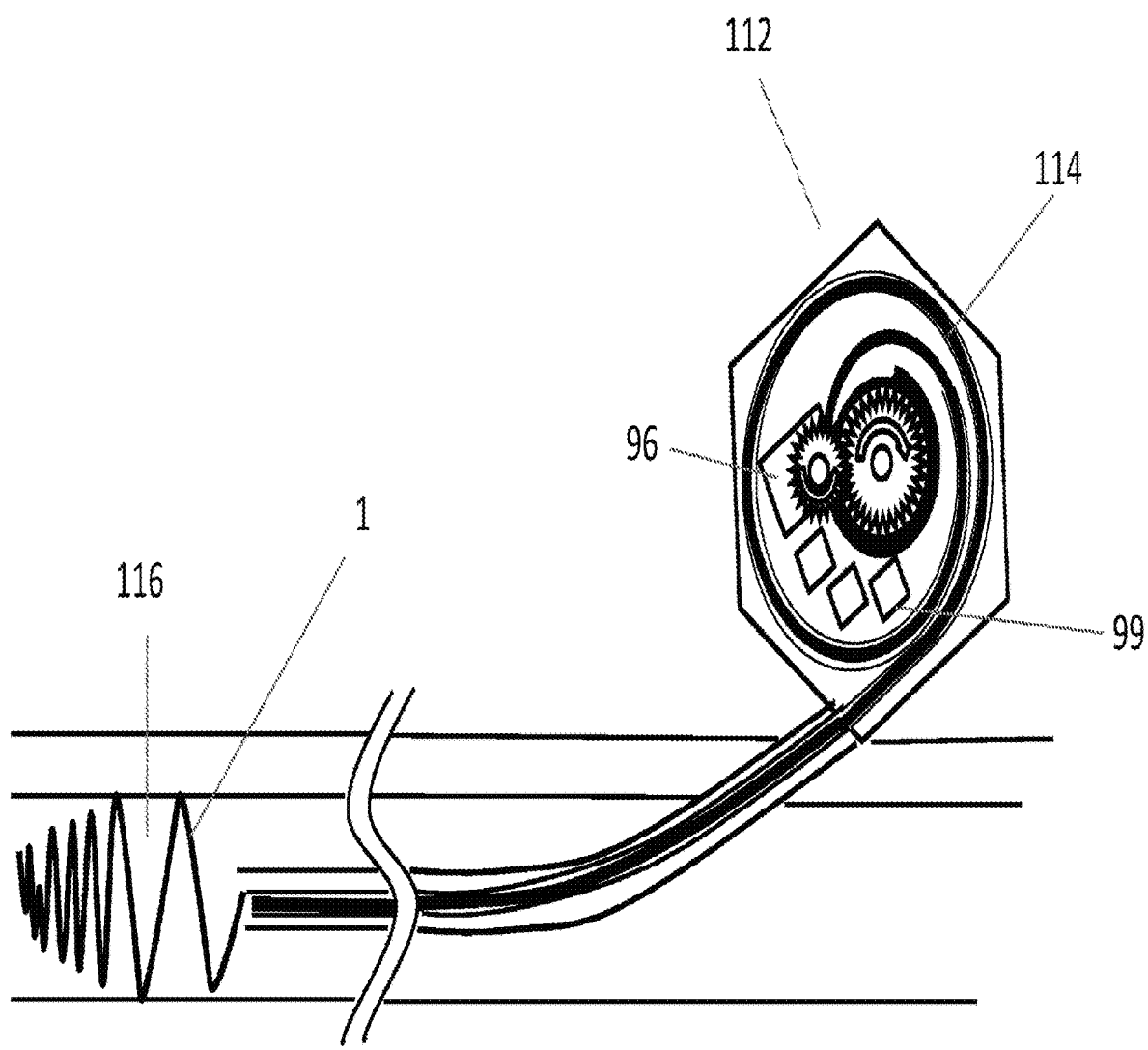
Figure 18D:
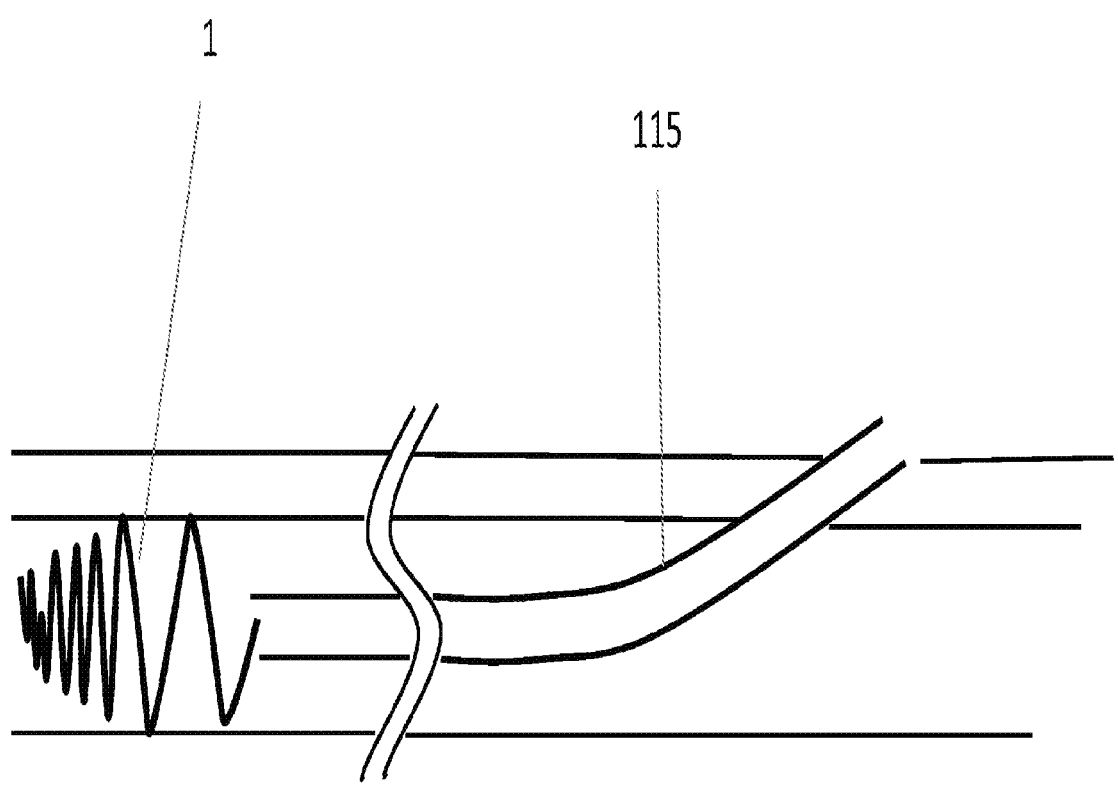
Figure 18E:
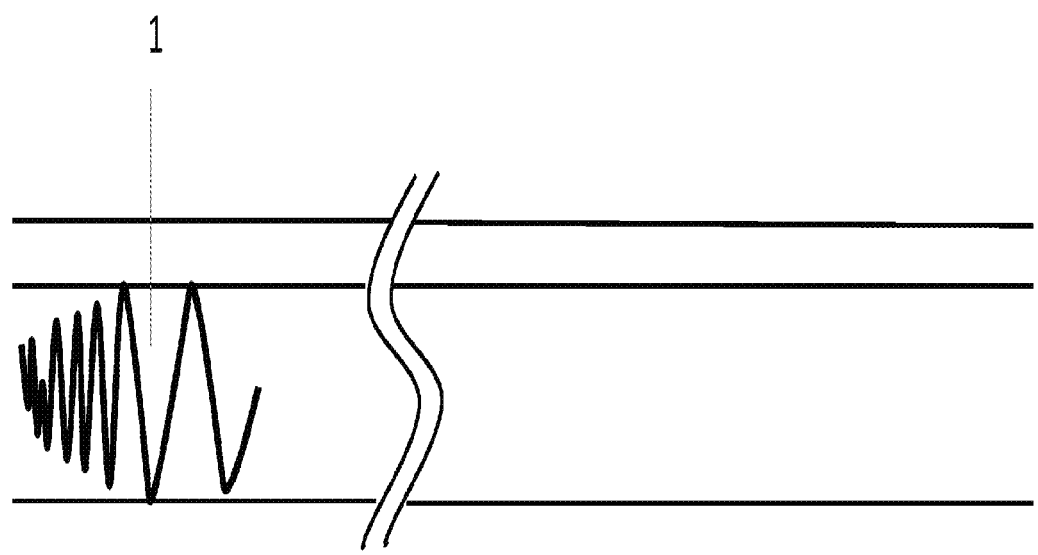

In some embodiments, embolic protection device 1 may be implanted in implantation site 116 using the following exemplary method is provided:
  catheter 115 may be placed with its distal end 117 near implantation site 116 within the lumen of vessel 5 (FIG. 18A). The proximal end 119 of catheter 115 may protrude outside the patient's skin in the vicinity of entry site 118. Insertion of catheter 115 into the patient's body may be performed as known in the art, using, for example, accessory devices such as an introducer sheath and a guiding wire;
  flexible tube 113 may be inserted into the lumen of catheter 115 through its proximal end 119 and advanced until the distal end of tube 113 is in the vicinity of implantation site 116 (FIG. 18B);
  system 112 may be instructed by input/output device 99 to cause motor 96 to advance pusher 114 thereby exteriorizing device 1 from the lumen of flexible tube 113 (FIG. 18C); and/or
  once device 1 is fully exteriorized from tube 113, system 112 may be withdrawn from the patient's body (FIG. 18D), and subsequently, catheter 115 may also be withdrawn from the patient's body (FIG. 18E).

In some embodiments of system 112, it may be possible to replace the controller, the power supply, and the driving mechanism by a manual mechanism configured to cause the drum to rotate and advance the pusher towards the end of the flexible tube, thereby exteriorizing the embolic protection device.

In some embodiments of system 112, embolic protection device 1 may be replaced by, for example, any of devices 1, 27 (without the stem, stopper, external anchor and pulling wire), 35 (without the stem, stopper, external anchor and pulling wire), 47 (without the stem, stopper, external anchor and pulling wire), 56 (without the stem, stopper, external anchor and pulling wire), or 62 (without the stem, stopper, external anchor and pulling wire). In some embodiments the protection devices may be implanted with the filter section tapering in the caudal direction. In some embodiments the protection devices may be implanted with the filter section tapering in the cranial direction.

In some embodiments of system 112, flexible tube 113 may be configured with a curved and sharp distal end, and the sharp distal end of flexible tube 113 may be configured to puncture the wall of vessel 5 from the inside of the vessel to the outside. In some embodiments, an embolic protection device, such as, for example, 27 (excluding the pulling wire) may be loaded in flexible tube 113 with the anchor pointing towards the sharp distal end of the flexible tube. In some embodiments, the anchor may be released from flexible tube 113 externally to the vessel wall, and the stem of the embolic protection device may traverse the vessel wall. In some embodiments, such "externally anchored" embolic protection device may be further exteriorized from flexible tube 113 by pulling system 112 out of the patient's body.

In some embodiments of system 112, flexible tube 113 may include a guide wire lumen, such that system 112 may be delivered to the implantation site over a guide wire (although in some embodiments, flexible tube 113 may be delivered directly to the implantation site without the need for a guide catheter or a guide wire).

In some embodiments, implant 1 may be loaded in flexible tube 113 such that upon exteriorization the supporting coils exit the distal end of the flexible tube first. The supporting coils may be configured with a diameter larger than the vessel diameter. Upon placement of the tip of flexible tube 113 at implantation site, the operator may cause the pusher to push only the supporting coils of implant 1 out of the flexible tube 113. The radial force exerted by the vessel wall on the supporting coil may be configured to keep them snugly secured against the vessel wall. The operator may then pull system 112 out of the patient's body, thereby causing the remainder of implant 1 to deploy at the implantation site.

In some embodiments, system 112 may include the implant (embolic protection device), the flexible tube and the pusher. The proximal end of the pusher may extend proximally from the proximal end of the flexible tube. The other components, such as the drum, the driving mechanism, the power supply, the controller, the input output device, and the housing are all optional. The operator may cause the pusher to push the implant or portions thereof out of the flexible tube by moving the pusher manually. The operator may push the pusher in order to exteriorize the implant entirely. In some embodiments, the implant may be loaded with the supporting coils configured to exit the distal end of the flexible tube first. The operator may push the pusher in order to exteriorize only the supporting coils, and then pull flexible tube back in order to exteriorize the remainder of the implant at the implantation site.

It is understood that monofilament filtering devices according to some embodiments of the present disclosure are possible in which, in a deployed state, the proximal end of the monofilament or the pull wire extends exteriorly from the patient's skin, or is implanted subcutaneously immediately below the patient's skin. Such devices are particularly suited for temporary usage, in which it is desired to retrieve the device shortly after a temporary embolus-enticing cause, such as surgery or minimally-invasive procedure.

In order to prevent stroke, filtering devices according to some embodiments of the present disclosure may be implanted in an artery supplying blood to the brain, such an aorta, a common carotid artery, an internal carotid artery, a subclavian artery, a brachiocephalic artery, or a vertebral artery.

In order to prevent pulmonary embolism, filtering devices according to some embodiments of the present disclosure may be implanted in a vein such as a superficial femoral vein, a deep femoral vein, a popliteal vein, an iliac vein, an inferior vena cava, or a superior vena cava.

The pusher in implantation systems according to the present disclosure need not be solid: exteriorization of embolic protection devices according to the present disclosure using pressurized fluid, liquid, or gas is possible.

In some embodiments of the embolic protection systems described above, such as, for example, systems 73, 74 and 91, the speed with which the monofilament is exteriorized from the needle may be limited. In some embodiments, the exteriorization speed limit may be less than 4 cm/sec. In some embodiments, the exteriorization speed may be less than 2 cm/sec. In some embodiments, the exteriorization speed may be less than 1 cm/sec. In some embodiments, the exteriorization speed may be less than 0.5 cm/sec. limiting the monofilament exteriorization speed may increase the probability of proper deployment, avoiding the entanglement of device coils.

In some embodiments, the devices pre-assembled in the embolic protection systems described above, may be any monofilament implants having an un-deployed shape wherein a portion of the monofilament is configured to fit within the lumen of the needle, and a functional, deployed shape in which the monofilament may be, for example, curved, bent, or twisted.

Any and all references to publications or other documents, including but not limited to, patents, patent applications, articles, webpages, books, etc., presented in the present application, are herein incorporated by reference in their entirety.

Accordingly, exemplary embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements. In other words, elements from one or another disclosed embodiment may be interchangeable with elements from other disclosed embodiments, thereby supporting yet other embodiments. Still other embodiments are possible with embodiments disclosed herein (or features thereof) combined with embodiments disclosed in the related applications incorporated by reference, or combined with elements/features/functionality of the embodiments from the incorporated by reference related applications. In addition, one or more features/elements of disclosed embodiments may be removed and still result in patentable subject matter (and thus, resulting in yet more embodiments of the subject disclosure). Certain embodiments may be patentable over the prior art for specifically lacking one or more elements, features, and/or functionality of that disclosed in the prior art. Accordingly, claims directed to such distinguishing embodiments (among the many embodiments disclosed herein) may include one or more negative limitations.

What is currently claimed is:

1. An embolic protection device (EPD) configured for arrangement within a blood vessel, the EPD comprising:
   a filament configured to include:
      an un-deployed state including at least a portion configured to fit within a lumen of a needle or a tube; and
      a deployed state wherein the filament automatically forms a helix comprising a support portion, and a filter portion,
   wherein:
      the support portion comprises a first portion of the helix which includes an axis, comprising an elongated coil having a height which exceeds a diameter thereof and is configured to at least one of orientate the filter portion within the blood vessel and secure the EPD relative to the blood vessel, the filter portion includes a funnel configured to taper in a first direction, the funnel also including at least one reducing coil having a center which is off the axis, at least a portion of the elongated coil is configured to resist axial compression of the support portion, the reducing coil is configured to capture emboli greater than a predetermined size;

and wherein the EPD further comprises:

a stem, as part of the deployed shape, configured to traverse a wall of the blood vessel, a pull wire configured to traverse a patient's skin and enable retraction of the device by pulling the device out of the blood vessel, a stopper configured to prevent the filament from moving from within the blood vessel outwards through a puncture in the blood vessel, an anchor configured to engage tissue of the blood vessel externally to the blood vessel, a second support portion, such that the filter portion is interposed between the support portion and the second support portion, and a second reducing coil whose center is off the axis.

2. The EPD of claim 1, further comprising a line segment connecting the centers of the reducing coil and the second reducing coil and which is configured to intersect the axis.

3. The EPD of claim 1, wherein the filament is made from nitinol.

4. The EPD of claim 1, wherein the filament cross section is round, and the diameter of the cross section is in the range of 0.05 and 0.3 mm.

5. An embolic protection device (EPD) configured for arrangement within a blood vessel, the EPD comprising:

a substantially straight, non-coiled filament configured to include:

an un-deployed state comprising at least a portion configured to fit within a lumen of a needle or a tube; and a deployed state comprising a support portion and a filter portion, wherein the support portion is shaped as a helix having an axis, the helix including at least a portion of a coil of the helix whose height exceeds its diameter, at least one coil of the helix includes a diameter which exceeds the diameter of the blood vessel for which the EPD is placed, the filter portion comprises a plurality of tapering coils including diameters decreasing in the direction towards the proximal or the distal end of the EPD, a reducing element comprising at least one reducing coil, the reducing coil being part of the helix whose center is off the helix axis, and the diameters of the plurality of tapering coils and the at least one reducing coil are smaller than the diameter of the blood vessel into which the EPD is implanted.

6. An embolic protection device (EPD) configured for arrangement within a blood vessel, the EPD comprising:

a substantially straight, non-coiled filament configured to include:

an un-deployed state including at least a portion configured to fit within a lumen of a needle or a tube; and a deployed state wherein the filament automatically forms a helix comprising a support portion, and a filter portion, wherein:

the support portion comprises a first portion of the helix which includes an axis, comprising an elongated coil having a height which exceeds a diameter thereof and is configured to at least one of orientate the filter portion within the blood vessel and secure the EPD relative to the blood vessel, the filter portion includes a funnel configured to taper in a first direction, the funnel also including at least one reducing coil having a center which is off the axis, at least a portion of the elongated coil is configured to resist axial compression of the support portion, the reducing coil is configured to capture emboli greater than a predetermined size, and the EPD further comprises a pull wire configured to traverse a patient's skin and enable retraction of the device by pulling the device out of the blood vessel.

7. The EPD of claim 6, wherein the EPD further comprises an anchor configured to engage tissue of the blood vessel externally to the blood vessel.

8. The EPD of claim 6, wherein the EPD further comprises a second support portion, such that the filter portion is interposed between the support portion and the second support portion.

9. The EPD of claim 6, wherein the EPD further comprises a second reducing coil whose center is off the axis.

10. An embolic protection device (EPD) configured for arrangement within a blood vessel, the EPD comprising:

a substantially straight, non-coiled filament configured to include:

an un-deployed state including at least a portion configured to fit within a lumen of a needle or a tube; and a deployed state wherein the filament automatically forms a helix comprising a support portion, and a filter portion, wherein:

the support portion comprises a first portion of the helix which includes an axis, comprising an elongated coil having a height which exceeds a diameter thereof and is configured to at least one of orientate the filter portion within the blood vessel and secure the EPD relative to the blood vessel, the filter portion includes a funnel configured to taper in a first direction, the funnel also including at least one reducing coil having a center which is off the axis, at least a portion of the elongated coil is configured to resist axial compression of the support portion, the reducing coil is configured to capture emboli greater than a predetermined size;

and wherein the EPD further comprises a stem, as part of the deployed shape, configured to traverse a wall of the blood vessel.

11. The EPD of claim 10, wherein the EPD further comprises a pull wire configured to traverse a patient's skin and enable retraction of the device by pulling the device out of the blood vessel.

12. The EPD of claim 10, wherein the EPD further comprises a stopper configured to prevent the filament from moving from within the blood vessel outwards through a puncture in the blood vessel.

13. The EPD of claim 10, wherein the EPD further comprises an anchor configured to engage tissue of the blood vessel externally to the blood vessel.

14. The EPD of claim 10, wherein the EPD further comprises a second support portion, such that the filter portion is interposed between the support portion and the second support portion.

15. The EPD of claim 10, wherein the EPD further comprises a second reducing coil whose center is off the axis.

16. An embolic protection device (EPD) configured for arrangement within a blood vessel, the EPD comprising:
- a monofilament configured to include:
  - an un-deployed state including at least a portion configured to fit within a lumen of a needle or a tube; and
  - a deployed state wherein the monofilament automatically forms a helix comprising a support portion, and a filter portion, wherein:
- the support portion comprises a first portion of the helix which includes an axis, comprising an elongated coil having a height which exceeds a diameter thereof and is configured to at least one of orientate the filter portion within the blood vessel and secure the EPD relative to the blood vessel,
- the filter portion includes a funnel configured to taper in a first direction, the funnel also including at least one reducing coil having a center which is off the axis,
- at least a portion of the elongated coil is configured to resist axial compression of the support portion,
- the reducing coil is configured to capture emboli greater than a predetermined size, and
- the EPD further comprises a stopper configured to prevent the monofilament from moving from within the blood vessel outwards through a puncture in the blood vessel.

17. An embolic protection device (EPD) configured for arrangement within a blood vessel, the EPD comprising:
- a monofilament configured to include:
  - an un-deployed state including at least a portion configured to fit within a lumen of a needle or a tube; and
  - a deployed state wherein the filament automatically forms a helix comprising a support portion, and a filter portion, wherein:
- the support portion comprises a first portion of the helix which includes an axis, comprising an elongated coil having a height which exceeds a diameter thereof and is configured to at least one of orientate the filter portion within the blood vessel and secure the EPD relative to the blood vessel,
- the filter portion includes a funnel configured to taper in a first direction, the funnel also including at least one reducing coil having a center which is off the axis,
- at least a portion of the elongated coil is configured to resist axial compression of the support portion,
- the reducing coil is configured to capture emboli greater than a predetermined size and
- the EPD further comprises a stem, as part of the deployed shape, configured to traverse a wall of the blood vessel.

* * * * *

UNITED STATES PATENT AND TRADEMARK OFFICE
CERTIFICATE OF CORRECTION

| | | |
|---|---|---|
| PATENT NO. | : 11,202,699 B2 | Page 1 of 1 |
| APPLICATION NO. | : 16/066860 | |
| DATED | : December 21, 2021 | |
| INVENTOR(S) | : Yair et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 34 days.

Signed and Sealed this
Thirteenth Day of December, 2022

*Katherine Kelly Vidal*

Katherine Kelly Vidal
*Director of the United States Patent and Trademark Office*